US009487839B2

(12) United States Patent
Arts et al.

(10) Patent No.: US 9,487,839 B2
(45) Date of Patent: Nov. 8, 2016

(54) METHOD FOR DETECTING SINGLE NUCLEOTIDE POLYMORPHISMS

(75) Inventors: Eric J. Arts, Cleveland Heights, OH (US); Matthew LaLonde, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 596 days.

(21) Appl. No.: 12/569,648

(22) Filed: Sep. 29, 2009

(65) Prior Publication Data

US 2011/0076677 A1   Mar. 31, 2011

(51) Int. Cl.
  C12Q 1/68      (2006.01)
  C12P 19/34     (2006.01)
  C07H 21/02     (2006.01)
  C12Q 1/70      (2006.01)

(52) U.S. Cl.
  CPC .............. C12Q 1/703 (2013.01); C12Q 1/6827 (2013.01)

(58) Field of Classification Search
  CPC .......... C12Q 1/6827; C12Q 2561/125; C12Q 2525/161; C12Q 2565/519; C12Q 2537/1373; C12Q 1/703; C12Q 2565/501
  See application file for complete search history.

(56) References Cited

U.S. PATENT DOCUMENTS

| | | | |
|---|---|---|---|
| 5,837,464 A | 11/1998 | Capon et al. | |
| 6,027,889 A | 2/2000 | Barany et al. | |
| 6,110,676 A * | 8/2000 | Coull et al. | 435/6.18 |
| 6,242,187 B1 | 6/2001 | Capon et al. | |
| 6,351,690 B1 | 2/2002 | Lenz | |
| 6,355,431 B1 | 3/2002 | Chee et al. | |
| 6,375,925 B1 | 4/2002 | Tsimikas et al. | |
| 6,406,911 B1 | 6/2002 | Dong | |
| 6,410,013 B1 | 6/2002 | Dong | |
| 6,489,098 B1 | 12/2002 | Petropoulos et al. | |
| 6,653,081 B2 | 11/2003 | Whitcomb | |
| 6,869,759 B1 | 3/2005 | Parkin et al. | |
| 6,942,969 B2 | 9/2005 | Capon et al. | |
| 6,967,076 B2 | 11/2005 | Dong | |
| 2002/0182609 A1 | 12/2002 | Arcot | |
| 2003/0003490 A1 | 1/2003 | Fan et al. | |

FOREIGN PATENT DOCUMENTS

WO      96/15271 A1    5/1996

OTHER PUBLICATIONS

Kellar K.L. et al. Experimental Hematology 30 (2002) 1227-1237.*
Alves K. et al. AIDS Research and Human Retroviruses. vol. 18, No. 2, 2002, pp. 161-165.*
Kozlowski P. et al. BioTechniques (2007) vol. 42 No. 5, pp. 584-588.*
Lalonde, M.A. 'HIV Drug Resistance Polymorphism Analysis Using Ligase Discrimination' Dissertation from Dept of Biochemistry, Case Wester Reserve University (2009), 325 printed pages.*
Bruse, S.E. ' Candidate Gene and MicroRNA Expression Studies of Schizophrenia' Disseration from Rutgers, The State University of New Jersey (2008), 123 printed pages.*
New England Biolabs (NEB) catalog (1998/1999), pp. 121 and 284.*
Rothstein et al. (1994) PNAS USA 91: 4155-4159.*
Riley L.K. et al DNA (1986) vol. 5, No. 4. p. 333-337.*
Search Report and Written Opinion, International Application No. PCT/US2010/050717, Jun. 23, 2011, 11 pages.
Noskov, et al., A general cloning system to selectively isolate any eukaryotic or prokaryotic genomic region in yeast. BMC Genomics. 2003, 4:16.
Jansson, et al., Biomarkers for monitoring efficacy of bioremediation by microbial inoculants. Environmental Pollution 107 (2000) 217 223.
Gao, et al., A Comprehensive Panel of Near-Full-Length Clones and Reference Sequences for Non-Subtype B Isolates of Human Immunodeficiency Virus Type 1, J. Virol. 1998; 72(2); 5680-5698.
Hwang, et al., Novel Retroviral Vector Transferring a Suicide Gene and a Selectable Marker Gene with Enhanced Gene Expression by Using a Tetracycline-Responsive Expression System. J. Virol. 1996; 70(11): 8138-8141.
Armstrong et al., Suspension Arrays for High Throughput, Multiplexed Single Nucleotide Polymorphism Genotyping, Cytometry, vol. 40, pp. 102-108, Jan. 20, 2000.
Barany, Genetic disease detection and DNA amplification using cloned thermostable ligase, Proc. Natl. Acad. Sci. USA, vol. 88, pp. 189-193, Jan. 1991.
Bjorndal et al., Coreceptor Usage of Primary Human Immunodeficiency Virus Type 1 Isolates Varies According to Biological Phenotype, Journal of Virology, vol. 71, No. 10, pp. 7478-7487, Oct. 1997.

(Continued)

*Primary Examiner* — Stephen Kapushoc
(74) *Attorney, Agent, or Firm* — Hahn Loeser & Parks LLP

(57) ABSTRACT

A method of detecting a single nucleotide polymorphism includes providing a first template polynucleotide, a second polynucleotide comprising a first and second sequence (complementary to a first portion of the first polynucleotide), and a third polynucleotide (complementary to a second portion of the first polynucleotide). The first, second and third polynucleotides are annealed, ligated and optionally, these steps are repeated. A fourth polynucleotide, which is essentially complementary to at least a portion of the first sequence, coupled to a first indicator is then provided. A fifth and/or sixth polynucleotide is provided. The fifth polynucleotide is essentially identical to at least a portion of the second sequence of the second polynucleotide and/or to at least a portion of the third polynucleotide. The sixth polynucleotide is essentially complementary to a portion of the second sequence of the second polynucleotide. The third or fifth polynucleotides may be coupled to a second indicator.

22 Claims, 15 Drawing Sheets

(56) References Cited

OTHER PUBLICATIONS

Bortolin et al., Analytical Validation of the Tag-It High-Throughput Microphere-Based Universal Array Genotyping Platform: Application to the Multiplex Detection of a Panel of Thrombophilia-Associated Single-Nucleotide Polymorphisms, Clinical Chemistry, vol. 50, No. 11, pp. 2028-2036, 2004.

Bruse et al., Improvements to bead-based oligonucleotide ligation SNP genotyping assays, BioTechniques, vol. 45, No. 5, pp. 559-571, Nov. 2008.

Cai et al., Detection of minor drug-resistance populations by parallel allele-specific sequencing, Nature Methods, vol. 4, No. 2, pp. 123-125, 187, Feb. 2007.

Cardozo et al., Structural Basis for Coreceptor Selectivity by the HIV Type 1 V3 Loop, Aids Research and Human Retroviruses, vol. 23, No. 3, pp. 415-426, 2007.

Carnevale, et al., A Multiplex Ligase Detection Reaction-Fluorescent Microsphere Assay for Simultaneous Detection of Single Nucleotide Polymorphisms Associated with Plasmodium falciparum Drug Resistance, Journal of Clinical Microbiology, pp. 752-761, Mar. 2007.

Connor et al., Change in Coreceptor Use Correlates with Disease Progression in HIV-1-Infected Individuals, J. Exp. Med., The Rockefeller University Press, vol. 185, No. 4, pp. 621-628, Feb. 17, 1997.

Da Re et al., Differentiating Plasmodium falciparum alleles by transforming Cartesian X,Y data to polar coordinates, BMC Genetics, 11:57, pp. 1-13, 2010.

Dejong, et al., Minimal Requirements for the Human Immunodeficiency Virus Type 1 V3 Domain to Support the Syncytium-Inducing Phenotype: Analysis by Single Amino Acid Substitution, Journal of Virology, pp. 6777-6780, Nov. 1992.

Deng et al., Identification of a major co-receptor for primary isolates of HIV-1, Nature, vol. 381, pp. 661-666, Jun. 20, 1996.

Dent, et al., A Polymerase Chain Reaction/Ligase Detection Reaction-Fluorescent Microsphere Assay to Determine Plasmodium falciparum NSP-1(sub)19 Haplotypes, The American Journal of Tropical Medicine and Hygiene, pp. 250-255, 2007.

Dorr et al., Maraviroc (UK-427,857), a Potent, Orally Bioavailable, and Selective Small-Molecule Inhibitor of Chemokine Receptor CCR5 with Broad-Spectrum Anti-Human Immunodeficiency Virus Type 1 Activity, Antimicrobial Agents and Chemotherapy, pp. 4721-4732, Nov. 2005.

Dragic et al., HIV-1 entry into CD4+ cells is mediated by the chemokine receptor CC-CKR-5, Nature, vol. 381, pp. 667-673, Jun. 20, 1996.

Dudley et al., Selection of a Simian-Human Immunodeficiency Virus Strain Resistant to a Vaginal Microbicide in Macaques, Journal of Virology, vol. 83, No. 10, pp. 5067-5076, May 2009.

Dunbar, Applications of Luminex® xMAPT™ technology for rapid, high-throughput multiplexed nucleic acid detection, Clinica Chimica Acta, 363, pp. 71-82, 2006.

Einstein et al., Genetic Variants in TAP Are Associated with High-Grade Cervical Neoplasia, Clin. Cancer Res. 2009;15(3), pp. 1019-1023, Feb. 1, 2009.

Hammer et al., Antiretroviral Treatment of Adult HIV Infection 2008 Recommendations of the International Aids Society—USA Panel, Journal of the American Medical Association, vol. 300, No. 5, pp. 555-570, reprinted Aug. 6, 2008.

Hartley et al., V3: HIV's Switch-Hitter, AIDS Research and Human Retroviruses, vol. 21, No. 2, pp. 171-189, 2005.

Hirsch, et al., Antiretroviral Drug Resistance Testing in Adult HIV-1 Infection: 2008 Recommendations of an International AIDS Society—USA Panel, HIV/AIDS Review Article, Clinical Infectious Diseases, vol. 47, pp. 266-285, Jul. 15, 2008.

Hunt, et al., Prevalence of CXCR4 Tropism among Antiretroviral-Treated HIV-1—Infected Patients with Detectable Viremia, Brief Report, The Journal of Infectious Diseases, vol. 194, pp. 926-930, Oct. 1, 2006.

Iannone et al., Multiplexed Single Nucleotide Polymorphism Genotyping by Oligonucleotide Ligation and Flow Cytometry, Cytometry, vol. 39, pp. 131-140, 2000.

King et al., Performance of Commercial Platforms for Rapid Genotyping of Polymorphisms Affecting Warfarin Dose, American Journal of Clinical Pathology, vol. 129, pp. 876-883, 2008.

Kondru et al., Molecular Interactions of CCR5 with Major Classes of Small-Molecule Anti-HIV CCR5 Antagonists, Molecular Pharmacology, vol. 73, No. 3, pp. 789-800, 2008.

Labrosse et al., Cooperation of the V1/V2 and V3 Domains of Human Immunodeficiency Virus Type 1 gp120 for Interaction with the CXCR4 Receptor, Journal of Virology, pp. 5457-5464, Jun. 2001.

Lalonde et al., Sensitive Oligonucleotide Ligation Assay for Low-Level Detection of Nevirapine Resistance Mutations in Human Immunodeficiency Virus Type 1 Quasispecies, Journal of Clinical Microbiology, pp. 2604-2615, Aug. 2007.

Lalonde et al., DNA Suspension Arrays: Silencing Discrete Artifacts for High-Sensitivity Applications, PLoS One, vol. 5, Issue 11, e15476, pp. 1-9, Nov. 2010.

Li et al., Persistent CCR5 Utilization and Enhanced Macrophage Tropism by Primary Blood Human Immunodeficiency Virus Type 1 Isolates from Advanced Stages of Disease and Comparison to Tissue-Derived Isolates, Journal of Virology, vol. 73, No. 12, pp. 9741-9755, Dec. 1999.

Markham et al., DINAMelt web server for nucleic acid melting prediction, Nucleic Acids Research, vol. 33, Web Server issue, pp. W577-W581, 2005.

McGovern et al., Population-based V3 genotypic tropism assay: a retrospective analysis using screening samples from the A4001029 and MOTIVATE studies, AIDS, vol. 24, pp. 2517-2525, 2010.

McNamara et al., Diagnosing Infection Levels of Four Human Malaria Parasite Species by a Polymerase Chain Reaction/Ligase Detection Reaction Fluorescent Microsphere-Based Assay, American Journal of Tropical Medicine and Hygiene, vol. 74(3), pp. 413-421, 2006.

Mefford et al., Bioinformatic Prediction Programs Underestimate the Frequency of CXCR4 Usage by R5X4 HIV Type 1 in Brain and Other Tissues, AIDS Research and Human Retroviruses, vol. 24, No. 9, pp. 1215-1220, Nov. 9, 2008.

Melby et al., HIV-1 Coreceptor Use in Triple-Class Treatment—Experienced Patients: Baseline Prevalence, Correlates, and Relationship to Enfuvirtide Response, The Journal of Infectious Diseases, vol. 194, pp. 238-246, Jul. 15, 2006.

Moore et al., The CCR5 and CXCR4 Coreceptors—Central to Understanding the Transmission and Pathogenesis of Human Immunodeficiency Virus Type 1 Infection, AIDS Research and Human Retroviruses, vol. 20, No. 1, pp. 111-126, 2004.

Mueller et al., High sensitivity detection of Plasmodium species reveals positive correlations between infections of different species, shifts in age distribution and reduced local variation in Papua New Guinea, Malaria Journal, vol. 8, pp. 1-14, Mar. 11, 2009.

Prosperi et al., Comparative determination of HIV-1 co-receptor tropism by Enhanced Sensitivity Trofile, gp120 V3-loop RNA and DNA genotyping, BioMed Central Ltd., Retrovirology, vol. 7:56, pp. 1-11, 2010.

Rahimian et al., Influence of DNA Structure on Adjacent Site Cooperative Binding, J. Phys. Chem. B, vol. 112, No. 29, pp. 8770-8778, Jun. 27, 2008.

Saracino et al., HIV-1 biological phenotype and predicted coreceptor usage based on V3 loop sequence in paired PBMC and plasma samples, Virus Research, vol. 130, pp. 34-42, 2007.

Seclén et al., High sensitivity of specific genotypic tools for detection of X4 variants in antiretroviral-experienced patients suitable to be treated with CCR5 antagonists, J. Antimicrob. Chemother., vol. 65, pp. 1486-1492, 2010.

Shafer et al., HIV-1 Drug Resistance Mutations: an Updated Framework for the Second Decade of HAART, AIDS Reviews, vol. 10, pp. 67-84, 2008.

Skrabal et al., Determining Human Immunodeficiency Virus Coreceptor Use in a Clinical Setting: Degree of Correlation between Two Phenotypic Assays and a Bioinformatic Model, Journal of Clinical Microbiology, vol. 45, No. 2, pp. 279-284, Feb. 2007.

(56) References Cited

OTHER PUBLICATIONS

Taylor et al., Flow Cytometric Platform for High-Throughput Single Nucleotide Polymorphism Analysis, Drug Discovery and Genomic Technologies, BioTechniques, vol. 30, No. 3, pp. 661-669, Mar. 2001.

Trouplin et al., Determination of Coreceptor Usage of Human Immunodeficiency Virus Type 1 from Patient Plasma Samples by Using a Recombinant Phenotypic Assay, Journal of Virology, vol. 75, No. 1, pp. 251-259, Jan. 2001.

Troyer et al., A Radiolabeled Oligonucleotide Ligation Assay Demonstrates the High Frequency of Nevirapine Resistance Mutations in HIV Type 1 Quasispecies of NVP-Treated and Untreated Mother-Infant Pairs from Uganda, AIDS Research and Human Retroviruses, vol. 24, No. 2, pp. 235-250, 2008.

Tuttle et al., Increased Replication of Non-Syncytium-Inducing HIV Type 1 Isolates in Monocyte-Derived Macrophages Is Linked to Advanced Disease in Infected Children, AIDS Research and Human Retroviruses, vol. 18, No. 5, pp. 353-362, 2002.

Van't Wout et al., Macrophage-tropic Variants Initiate Human Immunodeficiency Virus Type 1 Infection after Sexual, Parenteral, and Vertical Transmission, Journal of Clinical Investigation, Inc., vol. 94, pp. 2060-2067, Nov. 1994.

Wagner et al., Detection of HIV-1 Drug Resistance in Women Following Administration of a Single Dose of Nevirapine: Comparison of Plasma RNA to Cellular Dna by Consensus Sequencing and by Oligonucleotide Ligation Assay, Journal of Clinical Microbiology, pp. 1555-1561, May 2010.

Weiser et al., HIV-1 coreceptor usage and CXCR4-specific viral load predict clinical disease progression during combination antiretroviral therapy, AIDS, vol. 22, pp. 469-479, 2008.

Westby et al., Emergence of CXCR4-Using Human Immunodeficiency Virus Type 1 (HIV-1) Variants in a Minority of HIV-1 Infected Patients following Treatment with the CCR5 Antagonist Maraviroc Is from a Pretreatment CXCR4-Using Virus Reservoir, Journal of Virology, vol. 80, No. 10, pp. 5909-5930, May 2006.

Whitcomb et al., Development and Characterization of a Novel Single-Cycle Recombinant-Virus Assay to Determine Human Immunodeficiency Virus Type 1 Coreceptor Tropism, Antimicrobial Agents and Chemotherapy, vol. 51, No. 2, pp. 566-575, Feb. 2007.

Xiao et al., CCR5 Coreceptor Usage of Non-Syncytium-Inducing Primary HIV-1 Is Independent of Phylogenetically Distinct Global HIV-1 Isolates: Delineation of Consensus Motif in the V3 Domain That Predicts CCR-5 Usage, Virology, vol. 240, pp. 83-92, 1998.

Ye et al., Fluorescent Microsphere-Based Readout Technology for Multiplexed Human Single Nucleotide Polymorphism Analysis and Bacterial Identification, Human Mutation, vol. 17, pp. 305-316, 2001.

Iwakuma et al., Self-Inactivating Lentiviral Vectors with U3 and U5 Modifications, Virology vol. 261, pp. 120-132, 1999.

Marozsan et al., Development of a yeast-based recombination cloning/system for the analysis of gene products from diverse human immunodeficiency virus type 1 isolates, Journal of Virological Methods 111, pp. 111-120, 2003.

Marozsan et al., Differences in the Fitness of Two Diverse Wild-Type Human Immunodeficiency Virus Type 1 Isolates Are Related to the Efficiency of Cell Binding and Entry, Journal of Virology, vol. 79, No. 11, pp. 7121-7134, Jun. 2005.

Moore et al., A Yeast Recombination-Based Cloning System to Produce Chimeric HIV-1 Viruses and Express HIV-1 Genes, Methods in Molecular Biology, vol. 304, Human Retrovirus Protocols: Virology and Molecular Biology, pp. 369-385, 2005.

Neumann et al., T20-insensitive HIV-1 from naïve patients exhibits high viral fitness in a novel dual-color competition assay on primary cells, Virology, pp. 251-262, 2005.

Rodenburg et al., Near Full-Length Clones and Reference Sequences for Subtype C Isolates of HIV Type 1 from Three Different Continents, AIDS Research and Human Retroviruses, vol. 17, No. 2, pp. 161-168, 2001.

\* cited by examiner

A.

B.

C.

| | | | # Interrogators Necessary[a] | # RCOs Necessary[a] | # Separate Rxns Necessary[a] |
|---|---|---|---|---|---|
| A | Interrogator<br>RCO[b] | GTACT<br>AAATGGAG | 1 | 64 | 64 |
| B | Interrogator<br>RCO[b] | GTACTA<br>AATGGAG | 4 | 16 | 16 |
| C | Interrogator<br>RCO[b] | GTACTAA<br>ATGGAG | 16 | 4 | 4 |
| D | Interrogator<br>RCO[b] | GTACTAAA<br>TGGAG | 64 | 1 | 1 |

| | | |
|---|---|---|
| | 70<br>GTACTAAATGGAG | HIV-1 Reverse Transcriptase<br>Codon 70 and flanking sequence |

Ligase Fidelity Window

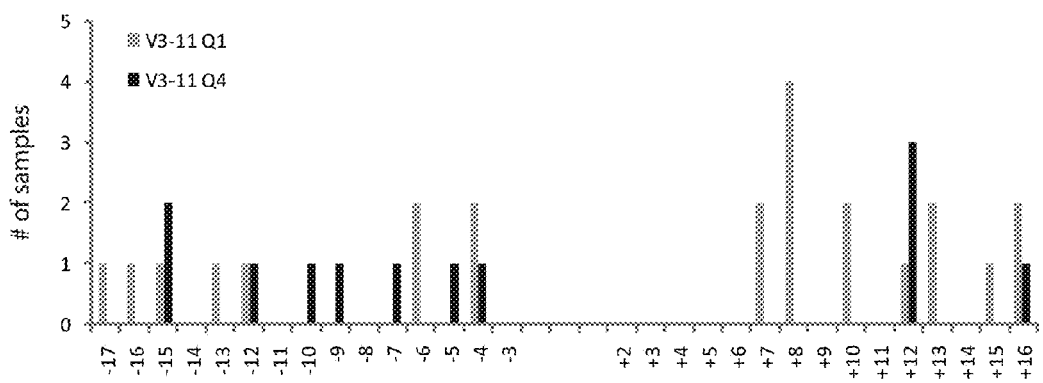

B

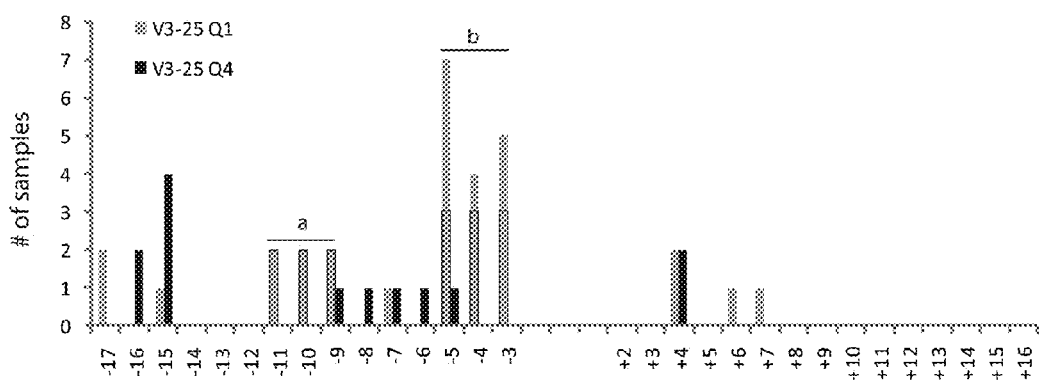

C

V3-25 (1st Quartile)

| Probe Sequence | TTTTUTICAACAGGA RBAATAGGARATATA |
|---|---|
| 04 | TTTTAT---ACAAGAAAAATAATAGGAAATATA |
| 07 | ATTTATGCAACA---AAAATTATAGGAGATATA |
| 08 | TTTTAT---ACAAGAAAAATAATAGGAAATATA |
| 18 | TTTTATGCAACAGGAAGCATAATAGGAGATATA |
| 26 | ATTTATGCAACA---AAAATTATAGGAGATATA |
| 29 | TTTTATACAACAAAAAACATAAATGGRGATATA |
| 39 | TTCTATACAACAGGAGACATAATAGGAAATATA |
| 54 | TTTTATGCAAGAAGAAACATAATAGGAGATATA |
| 56 | TTTTATGCAACAGGGGAGATAATAGGAGATATA |
| 58 | TTTTATGCAACAGGGAGAATAATAGGAGATATA |
| 69 | TTTTATGCAACA---GACATAATAGGAGATATA |

Fig. 15

METHOD FOR DETECTING SINGLE NUCLEOTIDE POLYMORPHISMS

STATEMENT REGARDING FEDERALLY SPONSORED RESEARCH OR DEVELOPMENT

This invention was made with government support under cooperative agreements awarded by NIAID, NIH Contract No. AI49170. The U.S. government may have certain rights to the invention.

INCORPORATION BY REFERENCE OF MATERIAL SUBMITTED ELECTRONICALLY

The material contained in the Sequence Listing provide herewith in ASCII compliant format in the text file entitled "200512-74_ST25.txt" created on Aug. 5, 2009 and containing 43333 bytes, is hereby incorporated by reference herein.

BACKGROUND OF THE INVENTION

Screening of genetic variations has become a matter of increasing importance in all types of genetic analysis, including medical analysis. Screening techniques have become common for detecting gross genetic variations, such as restriction fragment length polymorphisms. However, genetic variation can also be cause by subtler changes in the genetic code, including changes in a single nucleotide in a particular sequence, referred to as single nucleotide polymorphisms (SNPs).

Among the areas where such genetic variations can be of critical importance is the treatment of Acquired Immunodeficiency Syndrome (AIDS). AIDS is caused by Human Immunodeficiency Virus type-1 (HIV-1) which can be subdivided into three highly divergent groups that include: M (main), O (outlier), and N (non-M or O). HIV-1 group M strains are responsible for over 95% of infections worldwide and are further separated into at least nine discreet subtypes or clades (A, B, C, D, F, G, H, J, and K), based on the sequence of complete genomes. Additionally, 13 recombinant forms (CRF) have been characterized that further increase the growing HIV-1 diversity. Overall HIV-1 displays 15-40% nucleotide diversity between subtypes and up to 30% nucleotide diversity within a subtype. Additionally, it has been estimated that there can be between 5 and 10% sequence diversity within an infected individual. In the past few years, HIV-1 research on pathogenesis, replication and host-virus interaction has shifted focus from subtype B laboratory strains to primary HIV-1 isolates of all subtypes. Thus, the heterogeneity of HIV-1 has introduced new challenges for cloning and subsequent functional studies.

HIV-1 carries a genome consisting of ribonucleic acid (RNA) rather than deoxyribonucleic acid (DNA). In addition to the same core gene structure shared among all retroviruses (i.e. the gag, pol, and env genes), the HIV-1 genome also harbors several genes found in multiply and singly spliced RNA transcripts (i.e. vif, vpr, tat, rev, vpu, and nef) that encode for several accessory proteins. Standard molecular biological techniques for manipulation of HIV-1 genetic elements are difficult to apply due to poor sequence conservation between different isolates. Unique restriction endonuclease sites are not conveniently distributed across the HIV-1 genome for selective introduction or mutation of various regions or genes. Additionally, the insertion of new restriction sites for cloning is problematic due to the likely disruption of one or more of the multiple open reading frames found in the virus. As a result, current research on HIV-1 replication relies upon a few closely related molecular clones that have matching restriction endonuclease sites. Alternatively, other methods for studying HIV-1 genes involve trans gene expression with respective deletion in a molecular clone to create pseudotyped viruses. However, these pseudotyped viruses are limited to a single round of replication since the full length functional genome is not packaged in the virus particle.

Treatment of individuals infected with HIV-1 with anti-retroviral drugs (ARVs) has changed the face of the AIDS epidemic. Previously, all infection with HIV-1 led to AIDS and mortality in an average of two to seven years. The first anti-HIV-1 ARV, 3'-azido-3'-deoxythymidine (AZT, zidovudine, Retrovir®) was approved in 1987 for therapy but was largely unsuccessful in prolonged treatment due to resistance. Until the advent of triple drug combination therapy (Highly Active AntiRetroviral Therapy or HAART), drug resistance was common in all treated patients and remained the primary reason for the failure of ARVs to control HIV viremia. Due to the issues of adherence, the need for lifelong therapy, drug tolerance, and incomplete viral suppression, resistance to ARV still emerges in patients undergoing HAART. Unfortunately, ARV resistance triggers a resumption of disease progression unless new ARVs can be administered in a HAART regimen. Pharmaceutical companies have been successful in continually developing new ARV and in different drug classes.

There are now FDA-approved drugs sub grouped into three classes of anti-HIV ARVs, which target different steps in the HIV lifecycle: reverse transcriptase inhibitors (RTIs) (nonnucleoside (NNRTI), and nucleoside (NRTI)), protease inhibitors (PRIs), and entry inhibitors (EI) (enfutride, fuseon or T20). Several new HIV-1 entry inhibitors that occlude a viral receptor on the host cells have been effective in pre-clinical development and are now in advanced clinical trials. Additionally, Integrase, another catalytic enzyme of HIV-1 has also been recognized as a rational therapeutic target for the treatment of infection. Integration of the HIV-1 proviral DNA genome into the host genome is essential for viral mRNA transcription but also establishes a stable viral episome in the host genome. Integrase inhibitors and various derivatives could be on the cusp for phase III clinical trials and FDA approval for use in HAART regimens. The continual need for new HIV-1 inhibitors targeting new enzymes or viral processes is due to the emergence of primary resistance to the current PRI and RTIs licensed for therapy. Many of the drug resistant HIV-1 strains selected under a previous regimen also confer cross-resistant to other ARVs in the current FDA-approved arsenal. Cross-resistance limits the use of other drugs in salvage therapy (i.e. following resistance to the first line regimen). Thus, monitoring drug resistance has become a key clinical tool in the management of HIV infected patients by their physicians.

HIV infection of CD4+ cells is facilitated by and dependent upon viral envelope (env) glycoprotein gp120 interaction with cellular receptor CCR5 or CXCR4. After CD4 binding, the gp120 bridging sheet subdomain makes important contacts with the chemokine receptor N-terminal domain. A second subdomain in gp120, the variable subdomain 3 (V3), is the main determinant of coreceptor usage, making contacts with the second extracellular loop (ECL2) of either CCR5 or CXCR4. An HIV-1 virion may use CD4 and either CCR5 (in which case the virus is denoted as an R5-tropic virus) or CXCR4 (denoted an X4-tropic virus) for entry, but may have capability to use both. Most new patient infections involve R5-tropic variants, even when the dominant variant in the infecting partner has dual/mixed tropic variants, but X4-tropic variants emerge in over 50% of patients who progress to AIDS. Since X4 capability is associated with disease progression, it is thought to represent a more aggressive phase in the course of natural HIV-1 infection, corroborated by in-vivo models demonstrating the more pronounced cytopathic effects of X4-tropic strains. While the factors which influence coreceptor switching during the natural course of clinical HIV-1 infection are not well understood, tropism measurements remain a useful tool in management of HIV+ patients, providing valuable information about both clinical disease progression and treatment options.

Characterization of the HIV-1 entry process has led to development of entry inhibitors, including Maraviroc (MVC), a CCR5 antagonist, a small molecule which binds the CCR5 coreceptor in such a way that CCR5 interaction with gp120 is precluded. Maraviroc was approved for use in treating HIV in 2006. In the MVC-bound form, CCR5 ECL2 is unable to make the necessary contacts with gp120 V3 subdomain. In the two years since MVC approval, viral tropism has gained more attention than ever before because MVC use is contraindicated for individuals harboring X4-tropic viruses and, in fact, might select for more pathogenic X4-tropic variants. Maraviroc therapy decisions, particularly for patients failing a front-line medication, must then be guided in part by measurement of the X4-tropic component of the patient infection.

Amino acids 11 and 25 in the HIV-1 surface glycoprotein gp120 V3 subdomain are thought to be the primary determinants of HIV-1 coreceptor usage. If the identity of either amino acid 11 or 25 is one bearing a positive charge, it is highly probable that the isolate is capable of using CXCR4 for entry into cells. Therefore, there is a need for an assay method for determining the identity of amino acids 11 and/or 25 of the HIV-1 surface glycoprotein gp120 V3 subdomain.

Available assays for functional tropism assessment using tissue culture methods are available, but they are slow and expensive. Commercially available genetic tests are either insensitive or unreliable. Thus, new methods are needed for detecting a number of single nucleotide polymorphisms particularly those that have been recognized as conferring drug resistance.

Monogram Biosciences is one company which provides tropism measurement, marketed as the Trofile assay. Bacterial recombination is used to insert PCR-amplified patient gp160-encoding sequences into an envelope expression vector. The resulting construct is co-expressed with a packaging construct, a plasmid which contains a packaging signal and expresses the remaining HIV proteins and luciferase, in an eukaryotic cell line. Expression of both plasmids creates virus-like particles (VLPs) coated with patient-derived gp120/gp41 trimers. Supernatants from the co-expression cultures, enriched in VLPs, are used to infect target cells expressing heterologous human CD4 and CXCR4. VLPs with envelope glycoproteins derived from X4-tropic patient viruses can enter the target cells and integrate the luciferase ORF. X4-tropism is assessed quantitatively by luminometry after incubation of the target cell lysates with a pro-luminescent luciferase substrate. Other assays have also been reported using similar methods for generating recombinant virus constructs and coreceptor determination yielding results comparable to the Monogram test. Although this functional assay has been instrumental in determining which patients are not candidates for maraviroc therapy, it is expensive and the nature of the test dictates a present turnaround time of at least 14 days. As with functional HIV drug resistance assays, this has fueled a demand for faster and less expensive predictive testing.

Genotyping and prediction using bioinformatic algorithms may be more convenient and accessible than tropism phenotyping, but the methods for doing so have a common caveat in that all rely on DNA sequencing data. Treatment-experienced patients often have mixed populations of some X4 and some R5-tropic viruses which are missed by bulk sequencing. While bioinformatics approaches might be faster and less expensive than functional tropism assignment, the insensitivity of DNA sequencing for minor variants is a significant handicap to their predictive value. One technique circumvents the DNA sequencing problem intrinsic to bioinformatic algorithms by detecting differential electrophoretic migration of patient-derived sequences hybridized to a standard probe sequence in a native polyacrylamide gel. Patient V3 loop sequences are PCR amplified, denatured and annealed to a short radiolabeled PCR product from a standard X4-tropic variant. Heteroduplexes are resolved by electrophoresis and differ in electrophoretic mobility depending on their complementarity to the probe sequence. In one recent study, an X4-positive result by the commercial assay (SensiTrop) had high predictive value (most X4 calls were correct), but was unable to call X4 phenotypes for over 50% of samples shown to be dual/mixed or X4-tropic by a functional assay. It seems that sensitivity issues resolved by circumventing bulk DNA sequencing have been replaced by sensitivity issues of another sort for this application.

The use of an oligonucleotide ligation assay (OLA) to detect single nucleotide polymorphisms has been previously described. Typically, a fragment of nucleic acid of interest is amplified by polymerase chain reaction (PCR). The PCR product is then denatured and one polynucleotide (or primer) is selected from each of two sets of adjacent single-stranded polynucleotides, which are complementary to the PCR product. The first set of polynucleotides are essentially identical except for the last two nucleotides on the 3' end of the polynucleotide. The second set of polynucleotide are essentially identical except for the first nucleotide on the 5' end. In this way, a nucleotide sequence pertaining to a predicted and specific amino acid can be inferred through specific annealing and ligation of these two oligonucleotides over a codon. Each of the polynucleotides in the second set of polynucleotides are also typically labeled in some way, such as radioactive labeling or by covalent attachment of a molecule which will permit capture and identification of the presence of the polynucleotide, such as biotin. Once annealed to the PCR product, a ligase enzyme is used to join adjacent single-stranded polynucleotides. The ligase will only join polynucleotides where there are no mismatches between the PCR product and the last two nucleotides of the first single-stranded polynucleotide and the first nucleotide of the second single-stranded polynucleotide. In other words, the polynucleotides will only be ligated where the combined single-stranded polynucleotides are completely complementary to the PCR product, particularly in the region of the junction of the two polynucleotides. Various combinations of the first and second polynucleotides are used in an OLA in a well of a streptavidin-coated 96-well plate. Thermostable ligase may be used and the ligation reaction may be followed by denaturation of the product, and further followed by additional ligation reactions. OLA product may then be analyzed and quantitated by colorimetric analysis of the plate well.

Suspension arrays are a new technology by which multiple analytes in a mixture can be measured independently.

The Luminex flow fluorimeter (or suspension array analyzer) is functionally equivalent to a three-color flow cytometer with dedicated gating specifically designed for analysis of microscopic beads. It measures the bead-associated fluorescence intensity of two classifier fluorophores in the bead as well as a reporter fluorophore. In this new methodology described below, oligonucleotide ligation assay (OLA) ligation products may be quantified on Luminex beads if one oligonucleotide (the downstream or reporter capture oligonucleotide; RCO) is labeled with the reporter fluorophore and the other (the upstream or interrogator oligonucleotide) specifically associates with suspension array bead. A physical link (a template sequence) between two oligonucleotides then couples ligase recognition of the allele to bead enrichment with the reporter fluorophore. In an assay for minority single nucleotide polymorphisms (SNPs), however, the oligonucleotide reagents must be significantly consumed during ligase discrimination to elicit a detectable response on the suspension array. Additionally, assay sensitivity was previously insufficient for the detection of SNPs of low frequency in a population.

A need exists for suspension array-based single nucleotide polymorphism (SNP) screening system that may be used for a variety purposes, including the detection and quantitation of minority SNPs in a population, such as in HIV treatment.

SUMMARY OF THE INVENTION

It is, therefore, an aspect of the present invention to provide a suspension-based screening method for single nucleotide polymorphisms.

It is another aspect of the present invention to provide a method for screening viral isolates for coreceptor tropisms.

In general, the present invention provides a method of detecting at least one single nucleotide polymorphism. The method comprises providing a first polynucleotide to be analyzed for the presence of at least one single nucleotide polymorphism (SNP), providing a second polynucleotide comprising a first sequence and a second sequence, and providing a third polynucleotide comprising a sequence that is essentially complementary to a second portion of the first polynucleotide immediately adjacent the first portion of the first polynucleotide. The second sequence of the second polynucleotide is essentially complementary to a first portion of the first polynucleotide.

The method also comprises subjecting the first, second and third polynucleotides to conditions under which complementary regions of the polynucleotides will anneal, ligating the second and third polynucleotides at a junction between the second and third polynucleotides when no mismatches between occur between the first polynucleotide and either of the last two nucleotides of the second polynucleotide or the first nucleotide of the third polynucleotide. Optionally, the annealed polynucleotides may additionally be denatured and the steps of subjecting the polynucleotides to conditions under which complementary regions of the polynucleotides will anneal and ligating the second and third polynucleotides may be repeated a predetermined number of times.

A fourth polynucleotide, which may be coupled to a first indicator is then provided. The fourth polynucleotide includes a sequence that is essentially complementary to at least a portion of the first sequence of the second polynucleotide. At least one of a fifth polynucleotide and a sixth polynucleotide is also provided. The fifth polynucleotide comprises a sequence that is essentially identical to at least a portion of the second sequence of the second polynucleotide or to at least a portion of the third polynucleotide, or both, or the fifth polynucleotide is essentially complementary to at least a portion of the third polynucleotide. The fifth polynucleotide may be devoid of a sequence of about 15 or more nucleotides that are complementary to the second sequence of the second polynucleotide. The sixth polynucleotide comprises a sequence that is essentially complementary to at least a portion of the second sequence of the third polynucleotide and is devoid of a sequence of about 15 or more nucleotides that are complementary to the third polynucleotide. As used herein, the term "essentially complementary" should be understood as indicating that any mismatches between the polynucleotides in question would not interfere with hybridization of the polynucleotides under conditions of high stringency as understood in the art. "Essentially identical" should be understood as indicating that the polynucleotides in question will hybridize to identical targets under conditions of high stringency.

In the method, at least one of the third polynucleotide and the fifth polynucleotide comprising a sequence that is essentially complementary to at least a portion of the third polynucleotide may be coupled to a second indicator when the fifth polynucleotide comprises a sequence that is essentially complementary to at least a portion of the third polynucleotide. The sixth polynucleotide is not coupled to an indicator identical to the second indicator.

The method also comprises subjecting the polynucleotides to conditions under which complementary regions of the polynucleotides will anneal, and detecting the presence of the first ands second indicators. Only those species that result from ligation of the second and third polynucleotides and annealing of the resulting polynucleotide to the fourth polynucleotide will result in a signal from the presence of both the first and second indicators. In other words, when no mismatches occur between the first polynucleotide and the second and third polynucleotides at the positions surrounding the junction, specifically the last (i.e., most 3') two nucleotides of the second polynucleotide and the first nucleotide (i.e., most 5') of the third polynucleotide, ligation between the second and third polynucleotides can occur.

In one embodiment, the invention further comprises providing both a fifth and a sixth polynucleotide after ligating the second and third polynucleotides. The sixth polynucleotide does not have sufficient complementarity to anneal to the fifth polynucleotide, thereby allowing the fifth polynucleotide to anneal to the first polynucleotide. In one particular example, the fifth and sixth polynucleotides have no more than about 15 consecutive nucleotides that are complementary.

In addition or in the alternative, the first or second indicator may be a polymer bead such as a polystyrene bead, having a diameter of less than 10 micrometers and containing at least one fluorophore. One example of such an indicator is a Luminex® bead. The first or second indicator may be a biotin molecule or other labeling molecule. Where the an indicator is biotin, the presence of the indicator can be detected by subsequent attachment of a fluorophore such as strepavadin-R-phycoerythrin. It is envisioned that a wide variety of fluorescent molecules may be used. These include, for example, cyanine dyes such as Cy3 and Cy5, Alexa Fluor dyes such as Alexa 532 and Alexa 546, BODIPY dyes, such as BODIPY TMR-X, and CryptoFluor dyes such as CryptoFluor Orange and CryptoFluor Tangerine. In other examples, the first or second indicator may be a magnetic bead. The invention should not be considered to be limited by the nature of the indicators used.

The method may be used to determine the genotype of a virus, particularly a retrovirus such as Human immunodeficiency virus 1 (HIV-1). The method may be described as using an oligonucleotide ligation assay (OLA) to determine the tropism of a particular viral strain or group of strains, and may be abbreviated "TropOLA." In such an application, the first polynucleotide is a polymerase chain reaction product of a viral polynucleotide sequence. In one particular example, at least a portion of the envelope glycoprotein 120 (gp120) coding region is amplified by PCR and used as the first polynucleotide. In another particular example, the portion of the gp120 coding region used includes variable subdomain 3 (V3), and in still another particular embodiment, the first polynucleotide encodes at least one of amino acid 11 and amino acid 25 V3.

The present invention also provides a kit for performing the methods described herein. A kit for detecting at least one single nucleotide polymorphism in a first polynucleotide sequence may comprise:

at least one second polynucleotide comprising a first sequence and a second sequence, where the second sequence is essentially complementary to a first portion of the first polynucleotide, at least one third polynucleotide comprising a sequence that is essentially complementary to a second portion of the first polynucleotide immediately adjacent the first portion of the first polynucleotide at a junction, at least one fourth polynucleotide coupled to a first indicator, wherein the fourth polynucleotide is essentially complementary to the first portion of the second polynucleotide, and at least one of at least one fifth polynucleotide and at least one sixth polynucleotide, wherein the fifth polynucleotide comprises a sequence that is essentially identical to at least a portion of the second sequence of the second polynucleotide or to at least a portion of the third polynucleotide or both or wherein the fifth polynucleotide is essentially complementary to at least a portion of the third polynucleotide, and wherein the at least one sixth polynucleotide comprises a sequence that is essentially complementary to at least a portion of the second sequence of the second polynucleotide.

At least one of the third and the fifth polynucleotide comprising a sequence that is essentially complementary to at least a portion of the third polynucleotide is coupled to a second indicator. The sixth polynucleotide is not coupled to the second indicator.

In another example, the kit comprises both at least one fifth and at least one sixth polynucleotide. In such an example, the sixth polynucleotide has no more than about 15 consecutive nucleotides that are complementary to an approximately equal number of consecutive nucleotides of the fifth polynucleotide.

In any of these examples, as in the method described above, the first or second indicator may be a polymer bead, such as a polystyrene bead for example, having a diameter of less than 10 micrometers and containing at least one fluorophore. The remaining indicator may be biotin. In any of these examples, the kit may additionally comprise a ligase, such as a thermostable ligase.

In one example, the kit may be used to detecting at least one single nucleotide polymorphism in a viral sample. In such an application, the second sequence of the at least one second polynucleotide may be essentially complementary to a first portion of a viral polynucleotide sequence and the at least one third polynucleotide may be essentially complementary to a second portion of the viral polynucleotide sequence immediately adjacent the first portion of the viral polynucleotide sequence. The kit may therefore be used to detect at least one single nucleotide polymorphism (SNP) in a human immunodeficiency virus 1 (HIV-1) sample, such as a SNP in a viral polynucleotide sequence that encodes at least a portion of envelope glycoprotein 120 (gp120). In one particular example, the kit may be used to detect at least SNP in a portion of the variable subdomain 3 (V3) of gp120. In particular, the kit may be used to detect a SNP at least one of amino acid 11 and amino acid 25 of V3.

BRIEF DESCRIPTION OF THE DRAWINGS

FIG. 4 is a table showing potential ligation site position schemes and the number of interrogator oligonucleotides and Reporter Capture Oligonucleotides (RCOs) necessary under each scheme. Footnotes: [a]Number reflects oligonucleotides or reactions necessary for full codon coverage of one site. [b]Reporter Capture Oligonucleotide.

Figure 10:
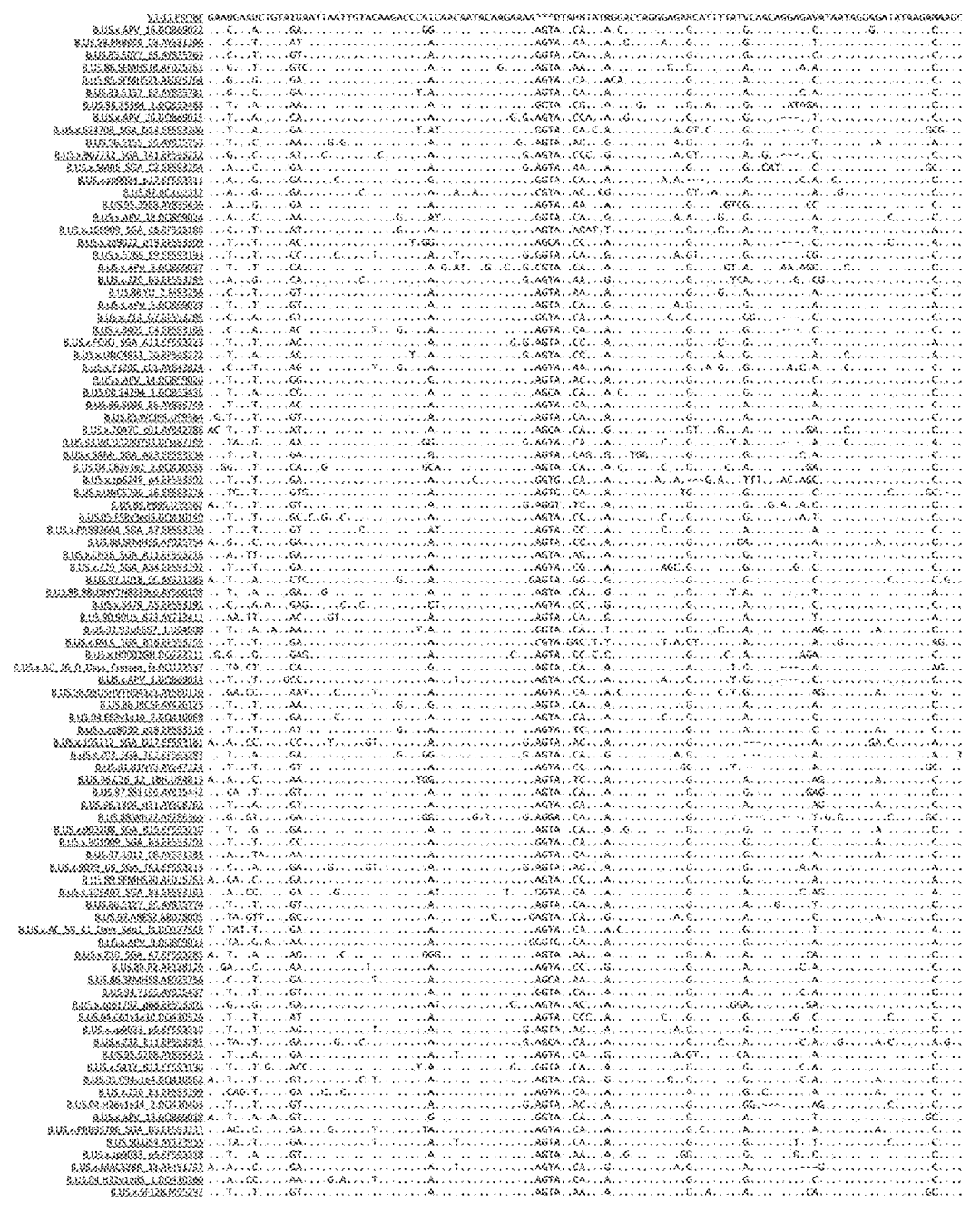

FIG. 10 shows the alignment of the V3 Codon 11 sequence (SEQ ID NOS: 86-91 and 101-112) with the individual patient sequences tested.

Figure 11:
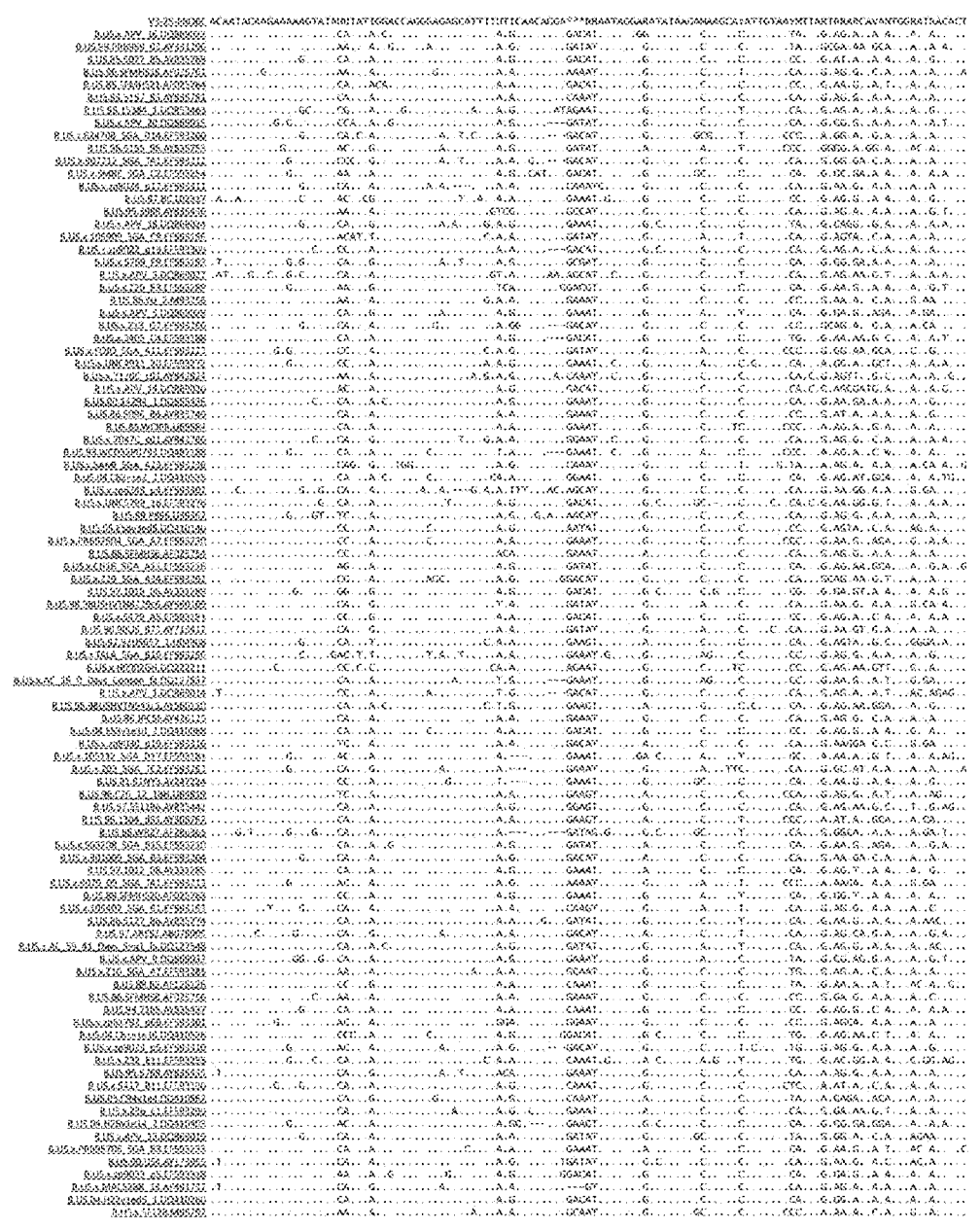

FIG. 11 provides the alignment of the V3 Codon 25 sequence (SEQ ID NOS: 92-100 and 113-120) with the individual patient sequences tested.

FIG. 15 is a position-specific base frequency analysis of Samples in the Upper vs. Lower Quartile (Overall Performance) as a Function of Probe Mismatch. X-axes indicate the number of bases from the ligation site. Negative numbers are mismatches in the interrogator and positive numbers are those in the RCO. Positions −2, −1 and +1 are the positions of the interrogated codon. Y-axes reflect number of samples harboring a mismatch at the position indicated on the X-axis. Legends indicate quartile 1 (Q1; low overall signal) or quartile 4 (Q4; high overall signal). Panel A provides mismatches within 15 bases of codon 11. Panel B provides mismatches within 15 bases of codon 25. Panel C provides codon 25 mismatches in the first quartile. Mismatches are highlighted. Shaded region indicates codon 25. Sample numbers are indicated on the left. The top sequence is the sequence present in all interrogators (to the left of codon 25, SEQ ID NOS: 92-100) and first design RCOs (to the right of codon 25, SEQ ID NOS: 113-120). Bases specifying codon 25 have been omitted since these are not common sequences among interrogators and among RCOs.

PREFERRED EMBODIMENT FOR CARRYING OUT THE INVENTION

The present invention provides improvements to oligonucleotide ligase assays (OLAs) that permit an OLA to be used in suspension arrays. Previously, it was not recognized that template-dependent hybridization species can confound assay sensitivity in OLAs, making previous OLAs impractical for use in suspension arrays. It has been discovered that the addition of competing polynucleotides can eliminate interrogator secondary structure, RCO secondary structure and template tethering, thereby improving OLA assay sensitivity.

Figure 1:
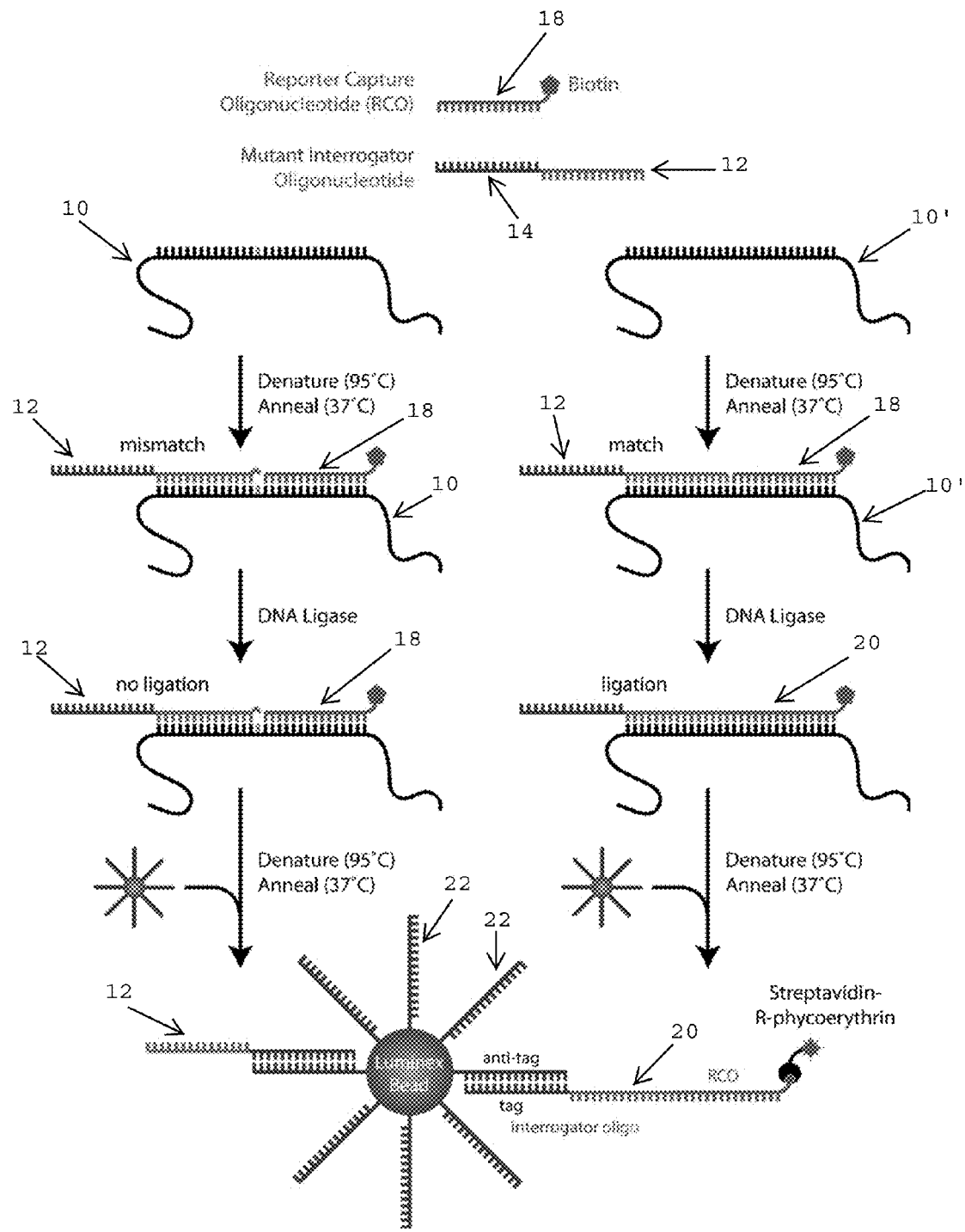
FIG. 1 is a schematic representation of a Ligation Detection Reaction for a matched and mismatched templates and oligonucleotides and subsequent annealing to a Luminex bead.

As stated above, the present invention provides a method of detecting at least one single nucleotide polymorphism. The method, which may be described with reference to FIG. 1, includes providing a first polynucleotide (or template) that is to be analyzed for the presence of one or more single nucleotide polymorphisms (SNPs). In FIG. 1, a wild type template 10 is provided on the left while a polymorphic sequence 10' is represented on the right. A second polynucleotide 12 is also provided. The second polynucleotide 12, also referred to as an interrogator oligonucleotide, has two portions: a first sequence or "tag" sequence 14, and a second sequence 16 adjoining the first sequence 14. The second sequence 16 is essentially complementary to a first portion of the template 10, 10' and therefore may also be referred to as an allele-specific sequence. Allele-specific sequence 16 of interrogator oligonucleotide 12 ends with the nucleotide position to be tested for the presence of a SNP on its 3' end.

A third polynucleotide 18, also referred to as a reporter capture oligonucleotide, is also provided. Reporter capture oligonucleotide 18 comprises a sequence that is essentially complementary to a second portion of the template immediately adjacent the first portion of the template. When annealed to the template 10, 10', reporter capture oligonucleotide 18 adjoins interrogator oligonucleotide 12 at a junction at the 5' end of the reporter capture oligonucleotide. Reporter capture oligonucleotide 18 is coupled on the 3' end to a first indicator, for example, biotin. It should be noted that variations in sequences outside of the codon of interest may be accounted for by the use of non-standard bases in either the interrogator oligonucleotide, the reporter capture oligonucleotide, or both. Deoxyinosine may be substituted into an oligonucleotide sequence to complement a purine transition (A↔G) polymorphism and deoxyuracil may be substituted into an oligonucleotide sequence to complement a pyrimidine transition (T↔C) polymorphism. Deoxyuracil may also be used to complement transversion polymorphisms (A or G↔T or C). Additionally or in the alternative, RCO (but not interrogator) sequences may also be designed to contain degenerate positions to accommodate sequence heterogeneity near the codon of interest. In the sequences described herein, nucleotides should be understood to be represented by their standard one letter abbreviations: A for adenine, G for guanine, C for cytosine, T for thymine and U for uracil. The presence of a mixture of nucleotides may also be indicated with an abbreviation as recognized in the art: N for any base (A, C, G or T/U), R for purine (G or A), Y for pyrimidine (T/U or C), M for amino (A or C), K for keto (G or T/U), S for G or C, W for A or T/U, V for nucleotides other than T (A, C, or G), D for nucleotides other than C (A, G, or T), B for nucleotides other than A (C, G, or T), and H for nucleotides other than G (A, C, or T).

The method also includes subjecting the first, second and third polynucleotides to conditions under which complementary regions of the polynucleotides will anneal. For example, the polynucleotides may be denatured at 95° C. and then allowed to anneal at 37° C. The second and third polynucleotides are ligated, such as by treatment with a ligase, when no mismatches between occur between the third polynucleotide (interrogator oligonucleotide) 12 and the template 10' at the nucleotide immediately adjacent the junction, providing a ligated oligonucleotide 20. On the other hand, when allele-specific sequence 16 of interrogator oligonucleotide 12 and the template 10 are mismatched at the 3' nucleotide adjoining the junction, ligase does not join interrogator oligonucleotide 12 and reporter capture oligonucleotide 18. The polynucleotides may then be denatured, for example, by heating to about 95° C. The steps of subjecting the polynucleotides to conditions under which complementary regions of the polynucleotides will anneal and joining the third and fourth polynucleotides may be repeated a predetermined number of times. In such a case, the use of a thermostable ligase may be advantageous.

A fourth polynucleotide (having a sequence complementary to the tag sequence, i.e., an anti-tag sequence) 22 coupled to a second indicator, such as a Luminex® bead, is also provided. A plurality of fourth polynucleotides 22 may be coupled to a single Luminex bead as illustrated in FIG. 1. When annealed to the fourth polynucleotide 22, ligated oligonucleotide 20 will result in a species that will possess both the first and second indicators.

Figure 2:
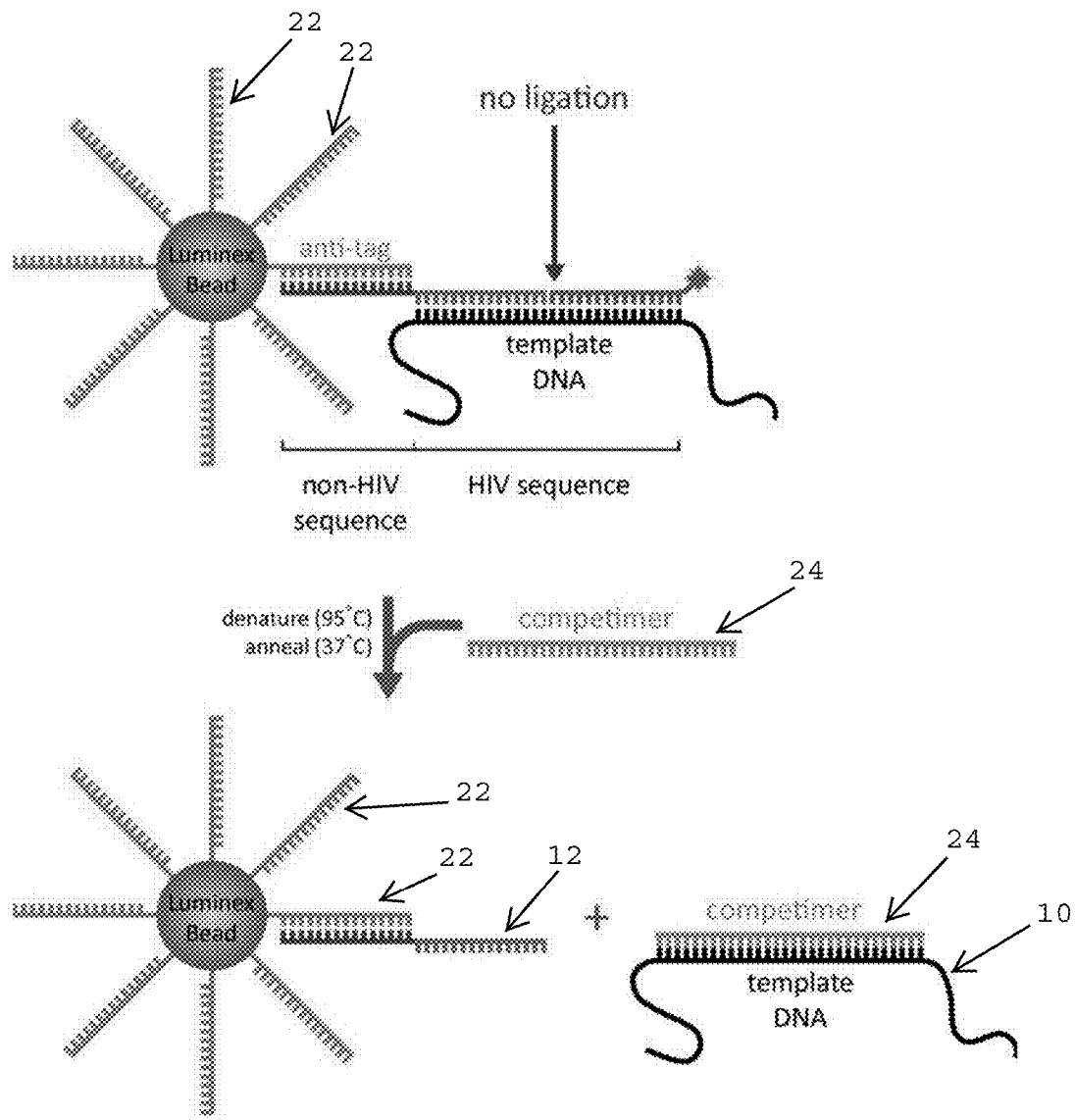
FIG. 2 is a schematic representation of the function of a competimer oligonucleotide in the claimed method.

A fifth polynucleotide may also provided in the method. In one example, the fifth polynucleotide functions as a competimer, as illustrated in FIG. 2. In a certain subset of cases where no ligation has occurred between interrogator oligonucleotide 12 and reporter capture oligonucleotide (RCO) 18, a dual signal from both the first and second indicators may nevertheless be present, due to the template 10 acting as a tether between interrogator oligonucleotide 12 and RCO 18. The competimer 24 comprises a sequence that is essentially identical to at least a portion of the allele-specific sequence 16 of the interrogator oligonucleotide 12 or to at least a portion of the reporter capture oligonucleotide 18 or both. Stated differently, competimer 24 is essentially complementary to at least a portion of template 10. The competimer may be devoid of the first and/or second indicator. Competimer 24 binds template 10 at a certain frequency, competing with allele-specific sequence 16 and RCO 18, and thereby decreasing the frequency at which template 10 acts as a tether between an unligated interrogator oligonucleotide 12 and RCO 18. In the method, the presence of the first and second indicators is then detected.

Figure 3:
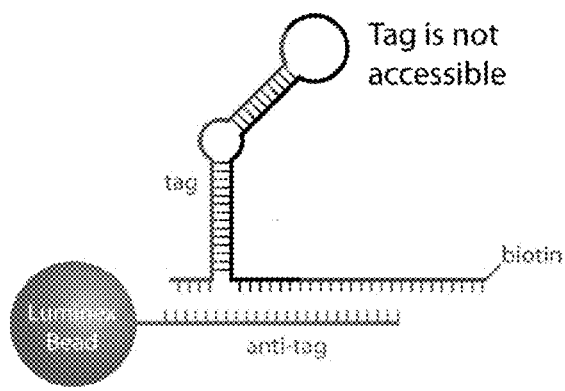
FIG. 3 is a series of schematic representations of the interaction or lack of interaction between a ligated oligonucleotide and an anti-tag sequence. In Panel A, a hairpin structure prevents annealing of the tag and anti-tag sequences. In Panel B, the presence of a duplex nucleator oligonucleotide permits annealing of the tag and anti-tag sequences. In Panel C, both a duplex nucleator and competimer oligonucleotide are present.
Figure 3:
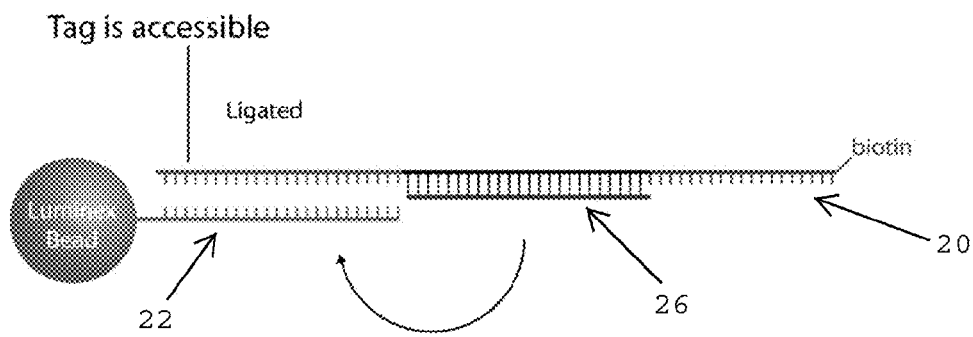
Figure 3:
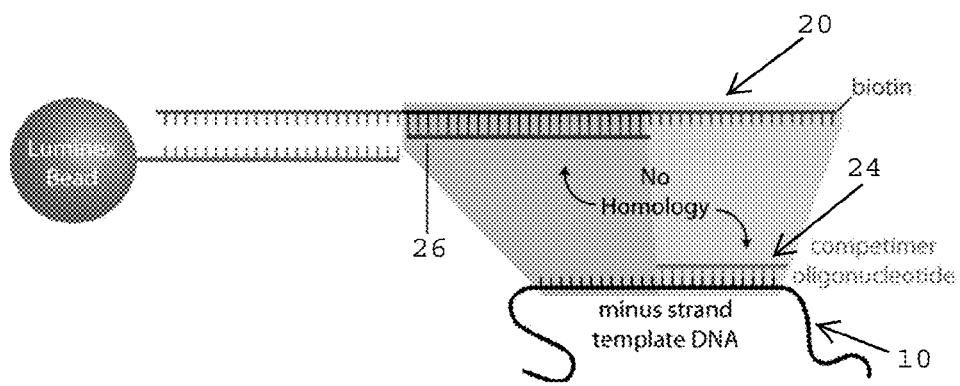

The method may include providing at least one sixth polynucleotide in addition to, or in replacement of, the fifth polynucleotide following ligating of the second and third polynucleotides. In one example, the at least one sixth polynucleotide is a duplex nucleator oligonucleotide, which is thought to increase the signal from interrogator oligonucleotides by the mechanism illustrated in FIG. 3. Without the duplex nucleator oligonucleotide, as shown in panel A, ligated oligonucleotide 20 may form hairpin structures which occupy the tag sequence of interrogator oligonucleotide 12 at some sequence-dependent frequency. This prevents the tag sequence from binding to the fourth polynucleotide 22, decreasing the total signal. The duplex nucleator polynucleotide 26 contains a sequence that is essentially complementary to at least a portion of the second sequence of the second polynucleotide. When both the fifth and sixth polynucleotides are provided, the at least one sixth polynucleotide does not have sufficient homology to anneal to the fifth polynucleotide. In one example, the sixth polynucleotide has no more than about 15 consecutive nucleotides that are complementary to an equal number of consecutive nucleotides of the competimer oligonucleotide (or fifth polynucleotide).

Additionally or in the alternative, the at least one sixth polynucleotide may comprise a duplex nucleator oligonucleotide, which is essentially complementary to the allele-specific sequence of the interrogator oligonucleotide, and also includes a separate oligonucleotide which has a sequence which is essentially complementary to the sequence of the RCO. Although not wishing to depend on any particular mechanism for patentability, it is thought that this RCO complement will promote binding of a duplex nucleator oligonucleotide, which in turn will promote binding of an anti-tag sequence to a tag sequence.

Example 1

Materials and Methods

Oligonucleotide Design

Oligonucleotides specific for subtype C were based on a curated alignment of 181 HIV-1 RT coding sequences of African origin obtained from Los Alamos HIV database in February of 2006. Subtype B oligonucleotides were based on a similar alignment of 174 HIV Pol coding sequences from the same source, accessed in April 2008. Sequence manipulation and analysis was performed in BioEdit program. Base frequency tables were processed manually and assign non-standard bases at the remaining polymorphic positions. Subtype B oligonucleotides were matched to anneal at 60-61° C. under the appropriate conditions. Annealing calculations omitted contributions from tag sequences. Secondary structure thermodynamics were predicted using the DNAMelt interface provided by Markham and Zuker (2005. DNAMelt web server for nucleic acid melting prediction. Nucleic Acids Res. 33:W577-W581). Interrogator oligonucleotides are shown in Table 1, reporter capture oligonucleotides in Table 2 and competimer oligonucleotides in Table 3. In the following Tables and the accompanying descriptions of the various oligonucleotides, the letter "I" should be understood to represent deoxyinosine and the letter "U" should be understood to represent deoxyuracil.

TABLE 1

Interrogator Oligonucleotides

| Seq. ID No. | Oligonucleotide Name | Oligonucleotide Sequence | Bead Association |
|---|---|---|---|
| 1 | 103StdUFM1 | TATACTATCAACTCAACAACATATTTAGGAATACCACACCCTGCAGGGTTAAAAAGAAT | LUA-089 |
| 2 | 103StdUFM2 | CTACAAACAAACAAACATTATCAATTAGGAATACCACACCCTGCAGGGTTAAAAAGAAC | LUA-028 |
| 3 | 103StdUFW1 | ATACTACATCATAATCAAACATCATTAGGAATACCACACCCTGCAGGGTTAAAAAGAAA | LUA-085 |
| 4 | 103StdUFW2 | CAATTCAAATCACAATAATCAATCTTAGGAATACCACACCCTGCAGGGTTAAAAAGAAG | LUA-005 |
| 5 | 103VM1 | TATACTATCAACTCAACAACATATTTAGGAATACCACAUCCUGCAGGITTAAAAUAGAAT | LUA-089 |
| 6 | 103VM2 | CTACAAACAAACAAACATTATCAATTAGGAATACCACAUCCUGCAGGITTAAAAUAGAAC | LUA-028 |
| 7 | 103VW1 | ATACTACATCATAATCAAACATCATTAGGAATACCACAUCCUGCAGGITTAAAAUAGAAA | LUA-085 |
| 8 | 103VW2 | CAATTCAAATCACAATAATCAATCTTAGGAATACCACAUCCUGCAGGITTAAAAUAGAAG | LUA-005 |
| 9 | 181VM2 | AATCCTTTTACATTCATTACTTACGACAAAAATCUTAGAGCCUTTTAGIIUAUAAAAUCCAGAUATAGTUATCTGT | LUA-008 |
| 10 | 181VM3 | AAACAAACTTCACATCTCAATAATGACAAAAATCUTAGAGCCUTTTAGIIUAUAAAAUCCAGAUATAGTUATCTGC | LUA-048 |
| 11 | 181VW2 | AATCAATCTTCATTCAAATCATCAGACAAAAATCUTAGAGCCUTTTAGIIUAUAAAAUCCAGAUATAGTUATCTAT | LUA-016 |
| 12 | 181VW3 | ATTATTCACTTCAAACTAATCTACGACAAAAATCUTAGAGCCUTTTAGIIUAUAAAAUCCAGAUATAGTUATCTAC | LUA-032 |
| 13 | STBPR-030-AAX | TACACTTTATCAAATCTTACAATCGGGCAICTAAAGGAAGCTCTATTAGATACAGGAGCAGATAA | LUA-003 |
| 14 | STBPR-030-GAX | CTTTATCAATACATACTACAATCAGGGCAICTAAAGGAAGCTCTATTAGATACAGGAGCAGATGA | LUA-002 |
| 15 | STBPR-054-ATX | CAATTCAAATCACAATAATCAATCGAAIATGGAACCAAAAATGATAGGGGGAATTGGAGGTTTTAT | LUA-005 |
| 16 | STBPR-054-GTX | TCAACAATCTTTTACAATCAAATCGAAIATGGAACCAAAAATGATAGGGGGAATTGGAGGTTTTGT | LUA-006 |
| 17 | STBPR-082-GCX | TAATCTTCTATATCAACATCTTACGAAATUTGUGGACAUAAAGCTATAGGTACAGTITTAITAGGACCTACACCTGC | LUA-009 |
| 18 | STBPR-082-GTX | AATCCTTTTACATTCATTACTTACGAAATUTGUGGACAUAAAGCTATAGGTACAGTITTAITAGGACCTACACCTGT | LUA-008 |
| 19 | STBPR-084-ATX | TACAAATCATCAATCACTTTAATCGACATAAAGCTATAGGTACAGTATTAITAGGACCTACACCTGTCAACAT | LUA-011 |
| 20 | STBPR-084-TGX | TACACTTTCTTTCTTTCTTTCTTTGACATAAAGCTATAGGTACAGTATTAITAGGACCTACACCTGTCAACTG | LUA-012 |
| 21 | STBPR-088-AAX | CTACTATACATCTTACTATACTTTAGCTATAGGTACAGTITTAITAGGACCTACACCTGTCAACATAATTGGAAGAAA | LUA-014 |

TABLE 1-continued

Interrogator Oligonucleotides

| Seq. ID No. | Oligonucleotide Name | Oligonucleotide Sequence | Bead Association |
|---|---|---|---|
| 22 | STBPR-088-AGX | ATACTTCATTCATTCATCAATTCAAGCTATAGG TACAGTITTAITAGGACCTACACCTGTCAACAT AATTGGAAGAAG | LUA-015 |
| 23 | STBRT-065-AAX | CTTTAATCTCAATCAATACAAATCGGCCTGAAA ATCCATAUAATACTCCAGTATTTGCUATAAAGA A | LUA-001 |
| 24 | STBRT-065-AGX | TACATTACCAATAATCTTCAAATCGGCCTGAAA ATCCATAUAATACTCCAGTATTTGCUATAAAGA G | LUA-004 |
| 25 | STBRT-074-GXX | ATCATACATACATACAAATCTACACAGTATTTG CCATAAAGAAAAAGACAGTACTAAATGGAGAA AAG | LUA-010 |
| 26 | STBRT-074-TXX | CAATTCATTTACCAATTTACCAATCAGTATTTG CCATAAAGAAAAAGACAGTACTAAATGGAGAA AAT | LUA-007 |
| 27 | STBRT-075-ACX | AATCAATCTTCATTCAAATCATCAAGTATTTGC CATAAAGAAAAAGACAGTACTAAATGGAGAAA ATTAAC | LUA-016 |
| 28 | STBRT-075-GTX | CAATAAACTATACTTCTTCACTAAAGTATTTGC CATAAAGAAAAAGACAGTACTAAATGGAGAAA ATTAGT | LUA-013 |
| 29 | STBRT-103-AAA | TCAATCAATTACTTACTCAAATACGGAATACCA CATCCUGCAGGGTTAAAAAGAAA | LUA-019 |
| 30 | STBRT-103-AAC | AATCCTTTTTACTCAATTCAATCAGGAATACCA CATCCUGCAGGGTTAAAAAGAAC | LUA-022 |
| 31 | STBRT-103b-AAA | TCAATCAATTACTTACTCAAATACCACATCCUG CAGGGTTAAAAAGAAA | LUA-019 |
| 32 | STBRT-103b-AAC | AATCCTTTTTACTCAATTCAATCACACATCCUG CAGGGTTAAAAAGAAC | LUA-022 |
| 33 | STBRT-151-ATX | CTACAAACAAACAAACATTATCAAGAGACACCA GGIATTAGATATCAGTACAATGTGCTTCCAAT | LUA-028 |
| 34 | STBRT-151-CAX | CTTTTCAATTACTTCAAATCTTCAGAGACACCA GGIATTAGATATCAGTACAATGTGCTTCCACA | LUA-025 |
| 35 | STBRT-181-TAX | TTCACTTTTCAATCAACTTTAATCGACAAAAAT CTTAGAGCCTTTTAGAAAACAAAATCCAGAUAT AGTTATCTA | LUA-031 |
| 36 | STBRT-181-TGX | TCATTCATATACATACCAATTCATGACAAAAAT CTTAGAGCCTTTTAGAAAACAAAATCCAGAUAT AGTTATCTG | LUA-034 |
| 37 | STBRT-184-AXX | CTTTTCATCTTTTCATCTTTCAATAGAGCCTTT TAGAAAACAAAATCCAGAUATAGTTATCTATCA ATACA | LUA-037 |
| 38 | STBRT-184-GXX | CTTTCTACATTATTCACAACATTAAGAGCCTTT TAGAAAACAAAATCCAGAUATAGTTATCTATCA ATACG | LUA-040 |
| 39 | STBRT-188-TAT | TACATCAACAATTCATTCAATACACTTTTAGAA AACAAAATCCAGAUATAGTTATCTATCAATACA TGGATGATTTGTAT | LUA-046 |
| 40 | STBRT-188-TTA | CTTTCAATTACAATACTCATTACACTTTTAGAA AACAAAATCCAGAUATAGTTATCTATCAATACA TGGATGATTTGTTA | LUA-043 |
| 41 | STBRT-190-GCX | TCAATCATCTTTATACTTCACAATAAATCCAGA UATAGTTATCTATCAATACATGGATGAUTTGTA TGTAGC | LUA-052 |

TABLE 1-continued

Interrogator Oligonucleotides

| Seq. ID No. | Oligonucleotide Name | Oligonucleotide Sequence | Bead Association |
|---|---|---|---|
| 42 | STBRT-190-GGX | TCATCAATCTTTCAATTTACTTACAAATCCAGA UATAGTTATCTATCAATACATGGATGAUTTGTA TGTAGG | LUA-049 |
| 43 | STBRT-215-ACX | TATATACACTTCTCAATAACTAACCATAGAACA AAAATAGAGGAACTGAGACAACATCTGTTGAIG TGGGGITTTAC | LUA-055 |
| 44 | STBRT-215-TAX | CTACTAATTCATTAACATTACTACCATAGAACA AAAATAGAGGAACTGAGACAACATCTGTTGAIG TGGGGITTTTA | LUA-058 |
| 45 | STBIN-148-AAX | TTCAATCATTCAAATCTCAACTTTGGCATTCCC TACAATCCCCAAAGTAA | LUA-023 |
| 46 | STBIN-148-CAX | CTTTTACAATACTTCAATACAATCGGCATTCCC TACAATCCCCAAAGTCA | LUA-020 |
| 47 | STBIN-148-CGX | AATCCTTTCTTTAATCTCAAATCAGGCATTCCC TACAATCCCCAAAGTCG | LUA-021 |
| 48 | STBIN-155-AAX | CTTTAATCCTTTATCACTTTATCAATTCCCTAC AATCCCCAAAGTCAAGGAGTAITAGAATCTATG AA | LUA-017 |
| 49 | STBIN-155-CAX | TCAAAATCTCAAATACTCAAATCAATTCCCTAC AATCCCCAAAGTCAAGGAGTAITAGAATCTATG CA | LUA-018 |

TABLE 2

Reporter Capture Oligonucleotides (RCOs)

| Seq. ID No. | Oligonucleotide Name | Oligonucleotide Sequence |
|---|---|---|
| 50 | STBRT-74-XTA | TAGTAGATTTCAGAGAACTTAATAAIAGAACTCAAGA CTTCTGGGAAGTTC |
| 51 | STBRT-184-XTG | TGGATGATTTGTATGTAGGATCTGACTTAGAAATAGGI CAGCATAGA |
| 52 | STBIN-148-XXA | AGGAGTAGTAGAATCTATGAATAAAGAATTAAAGAA AATTATAGGACAIGTAAGAGATCAGG |
| 53 | STBPR-84-XXA | AATTGGAAGAAATCTGTTGACTCAGUTTGGUTGUAC |
| 54 | STBRT-I90-XXA | ATCTGACTTAGAAATAGGICAGCATAGAACAAAAATA GAGGAACTGAGAC |
| 55 | STBRT-65-XXA | AAAAGACAGTACTAAATGGAGAAAATTAGTAGATTTC AGAGAACTTAATAAIAGAACTCAAG |
| 56 | STBRT-75-XXA | AGATTTCAGAGAACTTAATAAIAGAACTCAAGACTTCT GGGAAGTTCAATTAG |
| 57 | STBIN-148-XXC | CGGAGTAGTAGAATCTATGAATAAAGAATTAAAGAA AATTATAGGACAIGTAAGAGATCAGG |
| 58 | STBPR-54-XXC | CAAAGTAAGACAGTATGATCAGATACUUITAGAAATU TGTGGACATAAAGC |
| 59 | STBPR.-82-XXC | CAACATAATTGGAAGAAATCTGTTGACTCAGUTTGG |
| 60 | STBRT-215-XXC | CACACCAGAUAAAAAACATCAGAAAGAACCUCCATT |
| 61 | STBRT-151-XXG | GGGATGGAAAGGATCACCAGCAATATTCC |
| 62 | STBIN-148-XXT | TGGAGTAGTAGAATCTATGAATAAAGAATTAAAGAAAATT ATAGGACAIGTAAGAGATCAGG |

TABLE 2-continued

Reporter Capture Oligonucleotides (RCOs)

| Seq. ID No. | Oligonucleotide Name | Oligonucleotide Sequence |
|---|---|---|
| 63 | STBIN-155-XXT | TAAAGAATTAAAGAAAATTATAGGACAIGTAAGAGATCAG GCTGAACATCTTAAIACAGCAG |
| 64 | STBPR-30-XXT | TACAGTATTAGAAGAUATGAATTTGCCAGGAAIATGGAAA CCAAAAATGATAG |
| 65 | STBPR-84-XXT | TATTGGAAGAAATCTGTTGACTCAGUTTGGUTGUAC |
| 66 | STBPR-88-XXT | TCTGTTGACTCAGUTTGGUTGCACTTTAAATTTT |
| 67 | STBRT-181-XXT | TCAATACATGGATGAUTTGTATGTAGGATCTGACTTA GAAATAG |
| 68 | STBRT-103-XXX | AAATCAGTAACAGTACTGGATGTGGGTGATG |
| 69 | STBRT-188-XXX | GTAGGATCTGACTTAGAAATAGGICAGCATAGAACAAAA ATAGAGGAAC |
| 70 | 103 C 1 | AAATCAGTIACAGTIUTIGATGTGGG |
| 71 | 181 C2 | TCAATAUATGGATGAUTTGTATGTAG |
| 72 | 181 C3 | CAATAUATGGATGAUTTGTATGTAGGATCUGACTTAG AGATAGG |

TABLE 3

Competimer Oligonucleotides

| Seq. ID No. | Oligonucleotide Name | Oligonucleotide Sequence |
|---|---|---|
| 73 | IN-148-Cmer | CCCCAAAGTCAAGGAGTARTAGAATCTATGAATAAAGAATT AAAGAAAATTATAGGACARGTAAGAGATCAGGCTGAACATC TTAARACAGCAG |
| 74 | PR-30-Cmer | GGAGCAGATGATACAGTATTAGAAGAMATRRRTTTRCCAGG AARATGGAAACCAAAAATGATAGGGGGAATTGG |
| 75 | PR-54-Cmer | GGAGGTTTTATCAAAGTAAGACAGTATGATCAGRTACYYRT AGAAATYTGYGGACAYAAAGCTATAGGTACA |
| 76 | PR-82-Cmer | CCTACACCTGTCAACATAATTGGAAGAAATCTGTTGACTCAG MTTGGYTGYACTTTAAATTTT |
| 77 | RT-103-Cmer | GGGTTAAAAAGAAAAAATCAGTAACAGTACTGGATGTGGG TGATGCATAYTTYTCAGTTCCC |
| 78 | RT-151-Cmer | GGATGGAAAGGATCACCAGCAATATTCCAAWGTAGCATGA CAAAAATCTTAGAGCC |
| 79 | RT-181-Cmer | GTTATCTATCAATACATGGATGAYTTGTATGTAGGATCTGAC TTAGAAATAGRRCAGCATAGARYAAAAATAGAGG |
| 80 | RT-215-Cmer | GTGGGGRTTTACCACACCAGAYAAAAAACATCAGAAAGAAC CYCCATTYCTTTGGATGGGT |
| 81 | RT-65-Cmer | CYATAAAGAAAAARGACAGTACTAAATGGAGAAAATTAGT AGATTTYAGAGAACTTAATAARARAACTCAAGACTTYTGGG A |
| 82 | RT-74-Cmer | TGGAGAAAATTAGTAGATTTYAGAGAACTTAATAARARAAC TCAAGACTTYTGGGAAGTTCAATTAGGAAT |
| 83 | 103LC | GGARGTTCAATTAGGAATACCACAYCCWGCAGGRTTAAAA MAGAANAAATCAGTRACAGTRYTRGATGTGGGSGATGCATA T |
| 84 | V3-11-COMP | VHAATTAATTGTAYAAGACCCARCAACAATACAAGAARARG TATAMMTATRGGACCAGGGARAGCAKTWTWTDCWACARSA |

TABLE 3-continued

Competimer Oligonucleotides

| Seq. ID No. | Oligonucleotide Name | Oligonucleotide Sequence |
|---|---|---|
| 85 | V3-25-COMP | TAMMTATRGGACCAGGGARAGCAKTWTWTDCWACARSAVRHATAATAGGARATATAAGAMAAGCAYATTGTAAYMTTARTR |

Positive Controls

Patient peripheral blood mononuclear cell extract (from Steve Meshnick, University of North Carolina at Chapel Hill) was Polymerase Chain Reaction (PCR) amplified using primers RTS1 (TAAACAATGGCCATTGACAGAAGA; SEQ. ID. NO. 121) and RTA9 (TAAATTTAGGAGTCTTTCCCCATA; SEQ. ID. NO. 124). Second round PCR was performed using 5 µl first round PCR product and primers RTS2 (TCAAAAATTGGGCCTGAAAATCCAT; SEQ. ID. NO. 122) and RTA8 (GCTATTAAGTCTTTTGATGGGTCAT; SEQ. ID. NO. 123). All PCRs were carried out under the following conditions: 95° C. for 2 minutes, 35 cycles of 95° C. for 30 seconds, 55° C. for 30 seconds and 72° C. for 1 minute and a final extension at 72° C. for 10 minutes with Platinum Taq DNA Polymerase (Invitrogen). A subtype B positive control was for plasmid pNL4.3 was amplified with primers ML-gag-F3 (GGACAYCAAATGAAAGATTGYACTGARAGAC AGGC; SEQ ID. NO. 128) and ML-int-R2 (CCCCCCTTTTCTTTTAAAATTGTGRA TGAATACTGCC; SEQ ID. NO. 129) using otherwise identical conditions.

All cloning and site-directed mutagenesis performed with the subtype C patient isolate followed manufacturer instructions: The RTS2-RTA8 amplicon was cloned into pCR.TOPO 2.1 from Invitrogen and grown in liquid culture overnight. Plasmids were isolated using Qiagen's Plasmid Isolation kit. Site-directed mutagenesis was performed with Stratagene QuickChange Multi Site-directed Mutagenesis kit and primers Mut103stC, Mut181 stC1, and Mut181stC2 (SEQ. ID. NOS. 125-127, respectively).

```
Mut103stC:
TTAGGAATACCACACCCTGCAGGGTTAAAAAAGAANAAATCAGT

Mut181stC1:
GTTAGAGCCCTTTAGAACAAAAAATCCAGAAATAGTCATCTRCCA

Mut181stC2:
GTTAGAGCCCTTTAGAACAAAAAATCCAGAAATAGTCATCTRTC
```

Mutations were verified by DNA sequencing (Davis Sequencing, Davis, Calif.) and inserts were amplified by PCR using the above conditions with RTS2 and RTA8. Amplicons were purified using the Qiagen PCR Cleanup Kit, verified by electrophoretic separation in agarose and quantitated using by the PicoGreen fluorescence assay (Invitrogen) on a fluorescent plate reader.

Ligase Detection Reactions (LDRs)

Except where indicated otherwise, all ligase detection reactions used 5 units of Ampligase DNA ligase (Epicentre Biotechnologies, Madison, Wis.) as estimated by the manufacturer in a 12 µl reaction with 1.2 µl 10× buffer supplied with each enzyme and 7.5 nM each oligonucleotide, with the exception of those using Ampligase. Ampligase reactions contained 7.5 nM each oligonucleotide, 15 mM Tris-HCl pH 8.3, 0.06% triton-X100, 1 mM dithiothreitol, 40 mM KCl, 7.5 mM $MgCl_2$, 0.3 mM NAD+ sodium salt and 0.08% PEG 6000. All reagents were reagent grade, obtained from Sigma (St. Louis, Mo.).

Radioactive Assays

One hundred pmol of the up-stream oligonucleotide was incubated at 37° C. for 10 minutes with 40 U T4 Polynucleotide Kinase (Invitrogen), 100 pmol of 3000 Ci/mmol $\gamma$-$^{32}$P-ATP (Perkin-Elmer), 20 µl 5× T4 PNK Forward Buffer (Invitrogen) in a 100 µl reaction. Labeling reactions were then incubated at 65° C. for 10 minutes and transferred to ice. Reactions were extracted with 25:24:1 vol/vol/vol Phenol/Chloroform/Isoamyl Alcohol (Roche, Basel, CHE) and eluted from G-25 Sephadex columns (Amersham, Piscataway, N.J.) according to manufacturer instructions. Ligase Detection reactions were performed as above, using the extracted probe. Five microliters stop solution, consisting of 0.0001% xylene cyanole, 0.0001% bromophenol blue in formamide, was added to each 12 µl LDR and heated to 95° C. for 5 minutes and left at room temperature until gel loading. A solution containing 10% polyacrylamide and 5 M urea in 1×TBE (0.1 M Tris-HCl, 0.1 M boric acid (pH 8.3) and 2 mM EDTA) was polymerized with 0.1% ammonium persulfate and 0.02% N—N—N'—N' tetramethyl-ethylene-diamine (TEMED) at room temperature for 30 minutes in a 30 cm×30 cm Bio-Rad Sequi-gen apparatus with a 49-well comb. Prior to sample loading, the gel was pre-run at 1800 V for 1 hour in 1×TBE. 2.5 µl each sample was loaded and run into the gel at 2200 V for 3 minutes. Reactions were separated by PAGE for 1.5 hours at 1600 V. After the run, the apparatus was disassembled and the gel, mounted on filter paper, was dried under vacuum for 2 hours and analyzed on a phosphorimager.

Bead and SAPE Hybridization and Flow Fluorimetry

Approximately 500 of appropriate Luminex® xMAP beads and 25 pmol of appropriate competimer oligonucleotides were added to each LDR in 1×TMAC buffer (2.5 M tetramethyl ammonium chloride (TMAC), 0.1 M Tris-HCl (pH 8.0), 3 mM EDTA and 0.1% SDS) in a volume of 60 µl. Reactions were subjected to 95° C. for 5 minutes followed by 37° C. for 45 minutes. One hundred nanograms strepta-vidin-phycoerythrin conjugate (SAPE; Invitrogen #S-866) was then added to each reaction in a solution of 1×TMAC in a volume of 6 ul. Reactions were subjected to 37° C. for 45 minutes. Seventy-five beads per region were measured on a Luminex 200 instrument at the highest RP1 PMT setting (typically 700-750 V).

Results

Oligonucleotide Design

Polymorphisms in HIV-1 sequences are frequently silent mutations or an intermediate codon in a mutational pathway. Zidovudine resistance mutation T215Y/F is one example. In our reference alignment, the most frequent wild-type codon 215 is ACC (threonine) but two sequences (0.8%) were found with each of the threonine synonyms ACA and ACT. Codon 215 also requires more than one base change to confer resistance to zidovudine. Tyrosine 215 and phenylalanine 215 are most frequently encoded by TAC and TCC, respectively, both requiring two base changes from the wild-type codon ACC (Thr). If the mutational pathway from $ACC_{Thr}$ to the mutant codon $TTC_{Phe}$ occurs through methionine codon ATC ($ACC_{Thr} \rightarrow ATC_{Met} \rightarrow TTC_{Phe}$), then identification of only the T→C nucleotide change in the second base of the codon might predict the drug resistant codon $TTC_{Phe}$ in error for a sequence harboring non-drug resistant $ATC_{Met}$. If the mutational pathway from $ACC_{Thr}$ to $TTC_{Phe}$ occurs through serine codon TCC ($ACC_{Thr} \rightarrow TCC_{Ser} \rightarrow TTC_{Phe}$), identification of only the A→T nucleotide change in the first base of the codon would also predict drug resistance in error. The defined and approximately codon-sized fidelity window of template-dependent DNA ligases then makes OLA an attractive methodology to identify drug resistance polymorphisms in HIV-1 sequences. However, any one of four juxtapositions can be chosen for design of oligonucleotides for querying a codon.

If all RCOs are present in the same reaction (those specifying A, C, G and T at the last base of the codon), that base would remain ambiguous since the flow fluorimeter cannot discern which RCO ligated. To work around this problem, different RCOs for the same site are used separately. Although ligase fidelity is roughly symmetric at the ligation-competent site, we have observed lower fidelity toward mismatches in the reporter capture oligonucleotide. Of the four possible ligation site juxtapositions, only one eclipses the ligase fidelity window with all three bases of the codon (see FIG. 4C). With this arrangement, only four reactions must be performed for complete and unambiguous codon assignment with a maximum of 16 possible interrogator oligonucleotides.

In FIG. 4, the HIV-1 reverse transcriptase sequence at codon 70 is used as an example for ligation site positioning relative to the codon of interest. (A) If the interrogator-RCO single strand break is positioned 5' to first base of the codon, we would require 64 separate reactions for full codon coverage (testing for all 64 codons at that site). Although the fidelity window is not absolute, as depicted here, ligase promiscuity would be higher for mismatches at bases 2 and 3 of the codon. (B) If the ligation site is positioned 3' to the first base of the codon, the fidelity window would not include the last base of the codon and would require 16 separate wells for full codon characterization. (C) This seems to be the best juxtaposition since the entire codon is inside the fidelity window and requires only 4 reactions. (D) While requiring only one detection, the fidelity window does not cover the most determinant base (the first base) of the codon.

Oligonucleotide Optimization

Single-stranded oligonucleotides bind to their complement on beads in direct proportion to their relative concentrations in a mixture. Specifically, during the bead hybridization step, the population of interrogator oligonucleotide that binds any one bead consists of 1) those which have been ligated to the reporter oligonucleotide and 2) those which have not been ligated to the reporter oligonucleotide (see FIG. 1). Thus, the proportion of ligated interrogator to unligated interrogator at the reaction endpoint is consequential to the value of the assay. It was possible that some optimal concentration of oligonucleotides for the suspension array methodology might be different than that concentration we found to be optimal in a radioactive assay and that this optimal concentration should be a function of both the endpoint reaction efficiency and the absolute quantity of product made. Either excessive or limiting OLA probe concentration could result in low suspension array signal amplitude. Excess quantities of the interrogator oligonucleotide cannot be consumed by the reaction endpoint. The excess interrogator oligonucleotide then competes with the ligated product for bead binding sites. On the other hand, limited quantities of oligonucleotide probes may be fully consumed by the endpoint of the reaction, but the ligated product cannot fully populate the bead. Both conditions, either too much probe or too little probe, result in a signal which is less than the signal which the bead can support.

Using a 5'-radiolabeled interrogator oligonucleotide, OLA was performed on a mixture of two templates, one with the wild-type $AAA_{Lys}$ and the other with the mutant $AAC_{Asn}$ reverse transcriptase codon 103. A series of template mixtures was constructed in which the correct template was serially diluted with the incorrect template. Ten nanograms of each template DNA mixture was detected using interrogator oligonucleotides 103VM1, 103VM2, 103VW1, 103VW2, 181VM2, 181VM3, 181VW2, and 181VW3 (SEQ. ID. NOS. 5-12, respectively) and RCOs 103C1, and 181C3 (SEQ. ID. NOS. 70 and 72, respectively), all at the indicated concentrations in 12 microliter (μl) reaction volumes. Only oligonucleotide 103VW1, matching the correct template, was radiolabeled. Cold 103 interrogators (103VM1, 103VM2, 103VW1, and 103VW2) and the codon 181 oligonucleotide set (181VM2, 181VM3, 181VW2, and 181VW3) were included to simulate multiplex reaction conditions. Reactions were separated by 10% denaturing PAGE and visualized with a phosphorimager (FIG. 5A) or quantified as follows. Efficiency was calculated at the end of 60 cycles as (100× (ligated)÷(ligated+unligated)). Both ligated and unligated values were corrected for lane background prior to calculation. (FIG. 5B).

Figure 5:
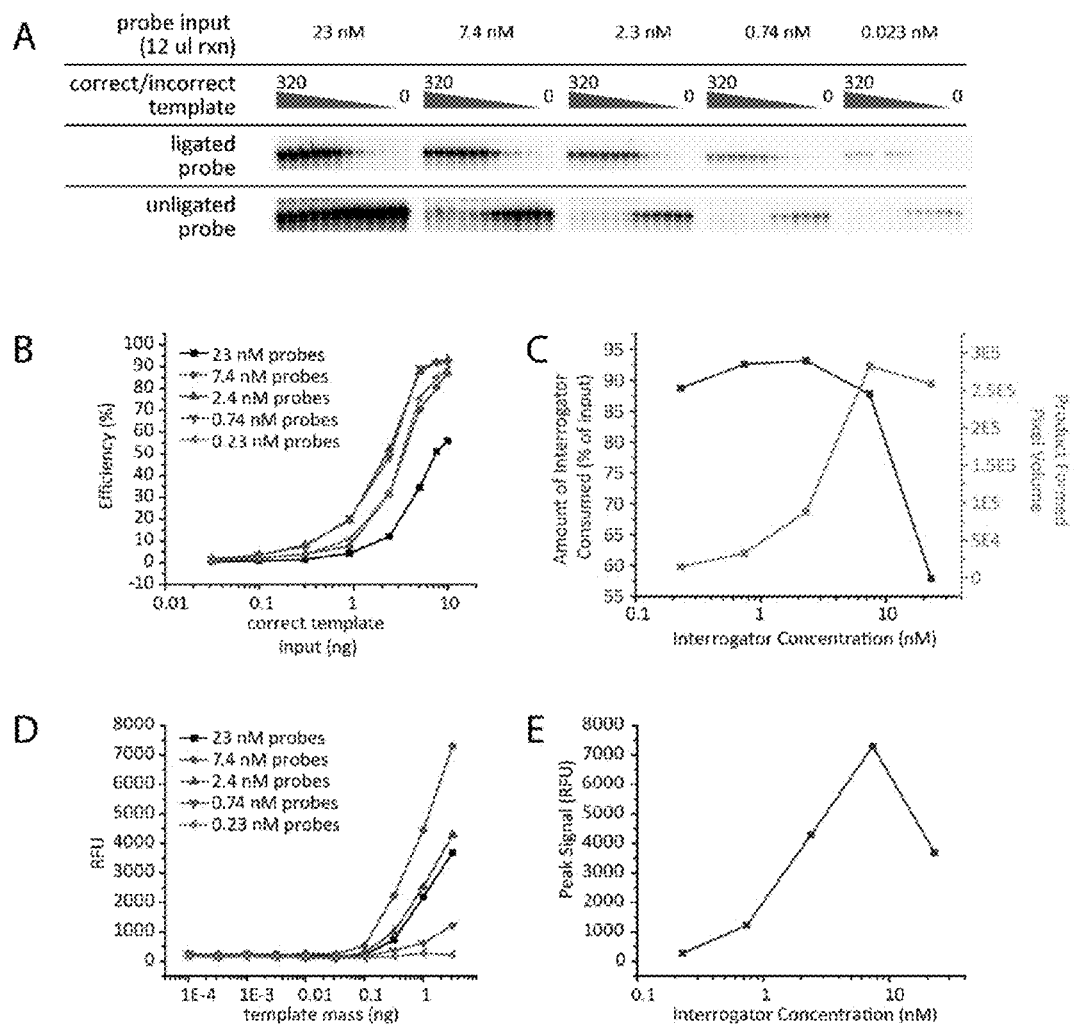
FIG. 5 is a series of images and graphs showing the results of oligonucleotide optimization studies. Panel A provides the results of radioactive banding from LDR probe depletion experiments. Panel B provides a graph plotting efficiency versus template input at various probe concentrations. Panel C is a graph showing the percentage of interrogator oligonucleotide consumed and amount of product formed versus interrogator concentration. Panel D is a graph showing signal intensity versus template input at various probe concentrations. Panel E is a graph plotting signal intensity versus interrogator oligonucleotide concentration.
Figure 6:
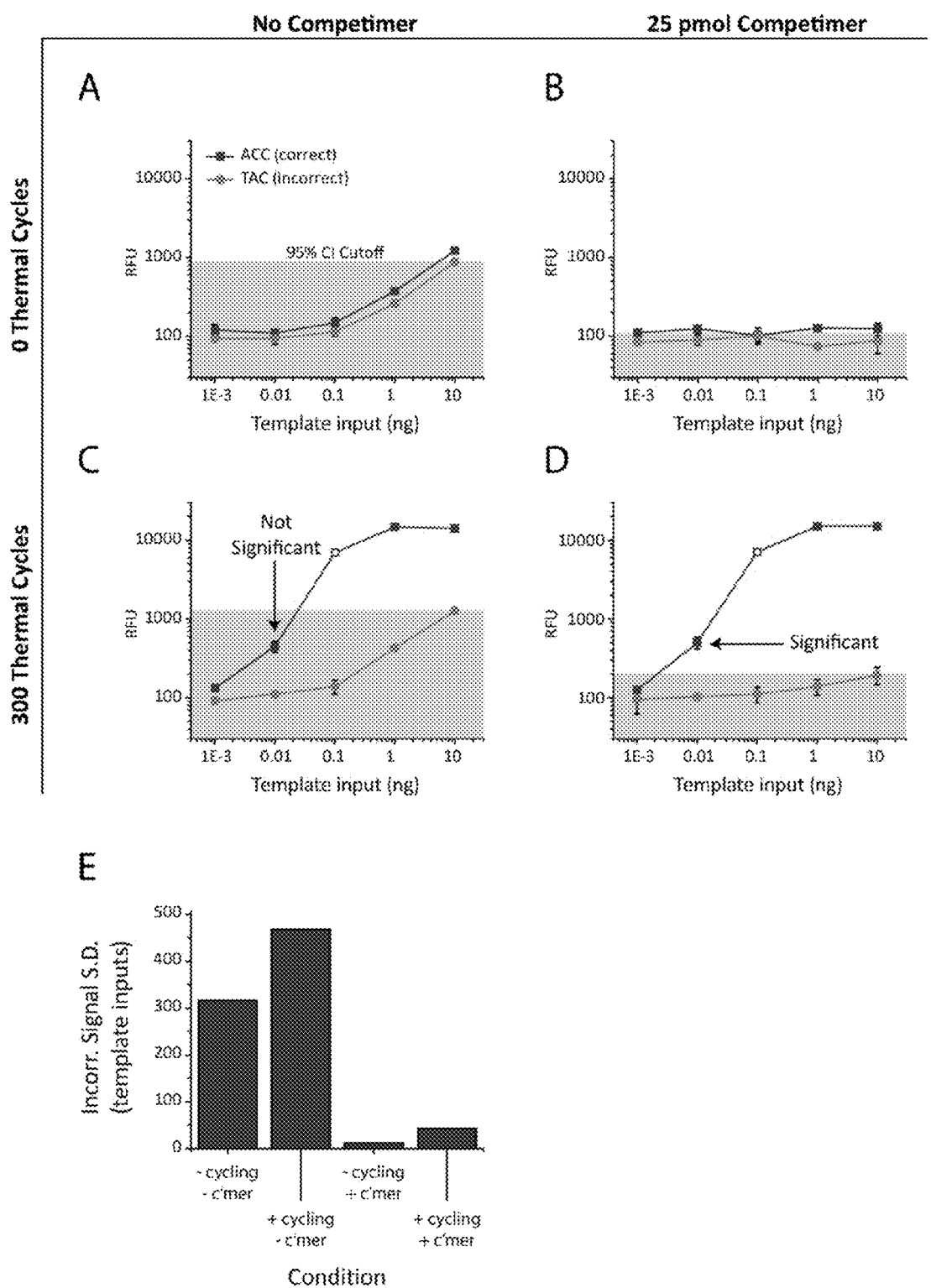
FIG. 6 is a series of graphs plotting signal intensity versus template input with and without the presence of a competimer oligonucleotide. OLAs were assembled and (A) frozen until bead hybridization omitting competimer oligonucleotide, (B) frozen until bead hybridization including 25 pmol/rxn competimer oligonucleotide, (C) subjected to 300 thermal cycles and bead hybridization omitting competimer oligonucleotide or (D) subjected to 300 thermal cycles and bead hybridization including 25 pmol/reaction competimer oligonucleotide. Grey fill indicates data points which are not significant in the 95% confidence interval. (E) Standard deviations across all template inputs from four separate detections were averaged and plotted as a function of reaction conditions presented in panels A-D.

As expected, higher concentrations of interrogator oligonucleotide yielded more ligated product (FIG. 5C). We then calculated the relative quantity of interrogator oligonucleotide consumed (endpoint reaction efficiency) for each oligonucleotide probe concentration. The darker trace in FIG. 5C represents the percent of interrogator oligonucleotide consumed with 10 ng template input. The lighter trace represents pixel volumes from ligated product bands (corrected for lane background). Endpoint reaction efficiency decreased sharply when the probe concentration exceeded 7.4 nM. Although the absolute quantity of product made increases with interrogator oligonucleotide concentration, the presence of excess unligated interrogator may skew the bead-bound oligonucleotide population toward unligated species.

Conversely, the lower interrogator concentrations needed to improve reaction efficiency might be inadequate to fully populate bead binding sites. We reasoned that the optimal concentration of interrogator oligonucleotides for the suspension array are such that both efficiency and ligation product are maximal, i.e. 7.4 nM as implicated in the previous radioactive experiment. An experiment was performed with the same oligonucleotides as in the previous experiment and analyzed by flow fluorimetry without radiolabeling (FIG. 5D). Median fluorescence intensity was corrected for the signal from no template input and plotted as a function of template input.

In FIG. 5E, corrected signal from 10 ng template input is shown as a function of LDR probe concentration. Results indicated that the optimal interrogator concentration for OLA analyzed by suspension array clearly occurs at the intersection of peak ligation efficiency and the amount of ligated product produced, i.e. around 7.4 nM (compare FIGS. 5C and E).

Figure 7:
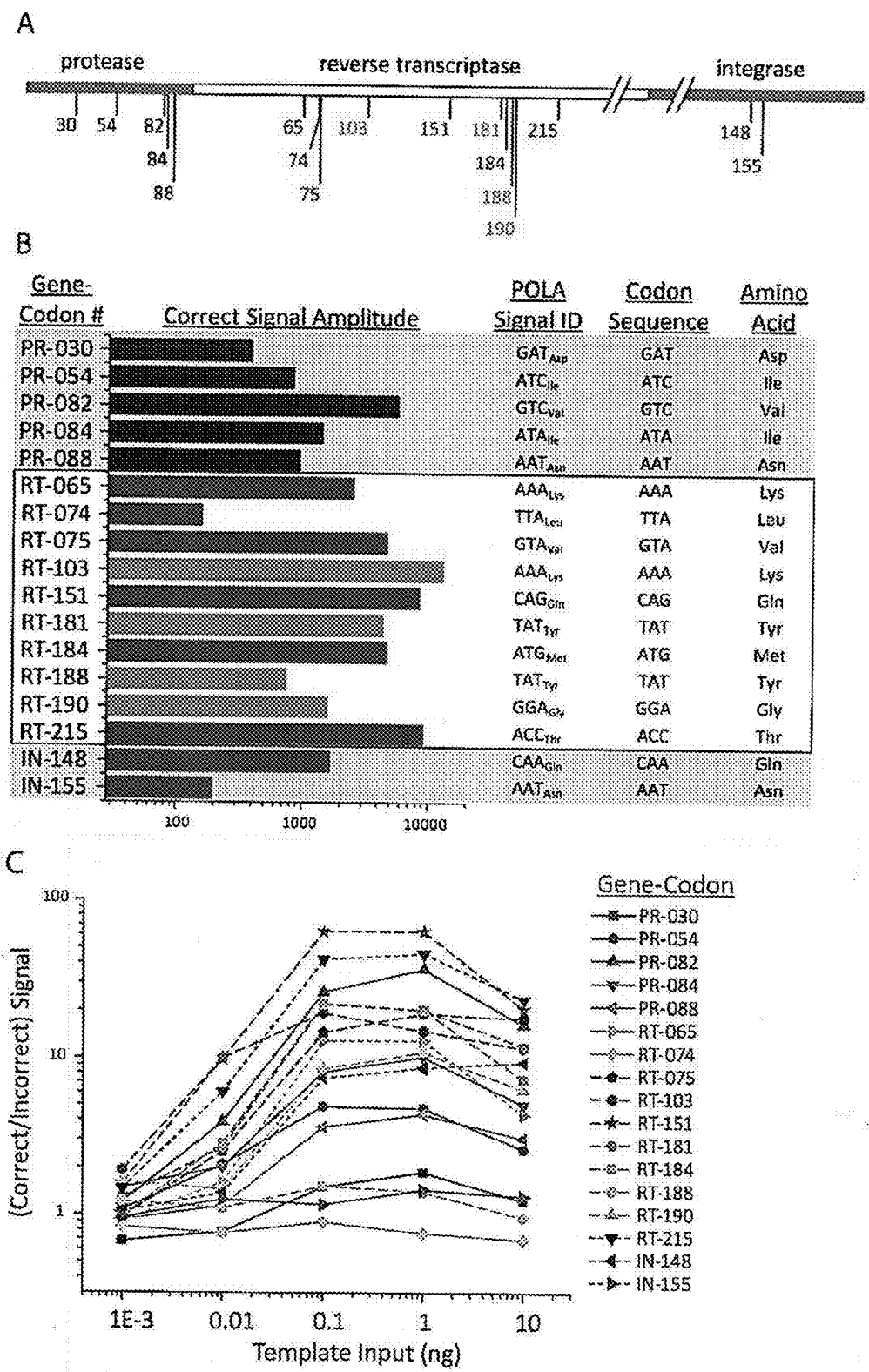
FIG. 7 is a schematic representation of a HIV-1 Pol OLA assay (POLA). Panel A is a representation of the portion of the HIV genome being tested. The locations indicated confer resistance to various antiretroviral drugs. Panel B is a bar graph showing peak intensity for each site tested. Panel C is a graph of the ratio of correct to incorrect signal versus template input for the various locations tested.

In early runs with the suspension array platform, we noticed template dose-dependent incorrect signal (FIG. 7C). Since high incorrect signal must be accounted for in the assay cutoff, this incorrect signal lowered the functional assay sensitivity. A similar phenomenon was not observed with the radioactive protocol (data not shown), so it was tentatively concluded that ligase error was not the cause. A hybridization species in which the template DNA tether reporter capture oligonucleotides to the bead-bound interrogator oligonucleotides ("template tethering" hereon), as shown in FIG. 2, was a more plausible explanation.

To examine the possibility that template tethering is the cause of this non-specific signal, sense-stranded oligonucleotides with the same sequence as the putative ligation product (competimers) were designed with extended complementarity on both the 5' and 3' such that they denature at a temperature approximately 10° C. above that of the interrogator or RCO sequence (Table 3). Degenerate bases were incorporated into competimer oligonucleotides to accommodate polymorphisms in the template DNA. Competimer oligonucleotides added during bead hybridization (after ligase discrimination) should sequester template DNA carried over from the legations as shown in FIG. 2. The increased homology at the 5'- and 3'-ends of the competimers should compete with both the ligated and unligated products for binding template DNA.

A dilution series of subtype B Pol PCR product (codon-sequence) was detected by flow fluorimetry as described in materials and methods using oligonucleotides STBRT-215-ACX$_{Thr}$ (SEQ. ID. NO. 43), STBRT-215-TAX$_{Tyr/STOP}$ (SEQ. ID. NO. 44), STBRT-215-XXC (SEQ. ID. NO. 60) and competimer RT-215-Cmer (SEQ. ID. NO. 80). OLAs were assembled and (A) frozen until bead hybridization omitting competimer oligonucleotide, (B) frozen until bead hybridization including 25 pmol/rxn competimer oligonucleotide, (C) subjected to 300 thermal cycles and bead hybridization omitting competimer oligonucleotide or (D) subjected to 300 thermal cycles and bead hybridization including 25 pmol/reaction competimer oligonucleotide. Grey fill indicates data points which are not significant in the 95% confidence interval. (E) Standard deviations across all template inputs from four separate detections were averaged and plotted as a function of reaction conditions presented in panels A-D.

As shown in FIGS. 7A-D, incorrect signal was template-dependent, reaching over 1000 RFU regardless of cycling conditions (FIGS. 7A and 7C). When competimers were added to bead hybridizations, the incorrect template-dependent signal disappeared (FIGS. 7B and 7D) with no significant change in correct signal (compare FIGS. 7C and D, open squares). We concluded that the source of incorrect template-dependent signal is a hybridization species in which the template DNA tethers unligated reporter capture oligonucleotide to the bead by forming a duplex with the unligated interrogator oligonucleotide (FIG. 2). This species should be quite stable since assay oligonucleotides form duplexes at more than 70° C. Further stabilization by the high concentration of tetramethyl ammonium chloride (TMAC) necessary for tat-anti-tag hybridization had most likely exacerbated this problem.

As an index of assay improvement, we calculated the 95% confidence interval (a typical assay cutoff) across all template inputs for all four conditions (FIGS. 7E and A-D, grey fill). Without competimer (FIG. 7B), assay sensitivity was limited to template inputs greater than 0.1 nanogram (ng) whereas competimer suppression of incorrect signal allowed detection of 0.01 ng template DNA. Thus, the 10-fold reduction in standard deviations across template inputs (FIG. 7E, compare 300 cycles with and without competimer) by yields an approximate 10-fold increase in sensitivity.

The negative template strand can tether the unligated interrogator to the unligated RCO in the absence of ligation. Correct signal replicates from 0.1 ng template input depicted in panels C and D (open squares) do not satisfy the Mann-Whitney nonparametric test for differences in median values within an acceptable confidence interval (p=0.47, W=15.0), indicating that no detectable change in correct signal amplitude was induced by the competimer oligonucleotide.

Multiplex Analysis of Drug Resistance Mutations in HIV Pol

Interrogator, reporter and competimer oligonucleotides were designed for 17 sites in HIV-1 subtype B Pol ORF which are known to independently confer resistance to one or more antiretroviral drugs (FIG. 7A) for an assay intended to detect minority drug resistance in the HIV-1 Pol ORF by OLA (POLA). Five codons in PR, ten in RT and two in IN were chosen based both on the magnitude of drug resistance they confer and on their relative prevalence among untreated patients (Stanford HIV Drug Resistance Database; http://hivdb.stanford.edu). Although multiple codons have been observed at most of these sites, we designed each oligonucleotide based on the most prevalent wild-type and mutant codons.

The 2752 bp amplicon from nt 2047 to 4799 (HXB2 numbering) was amplified from plasmid pNL4-3, purified, quantified (described above) and used as a positive control to assess assay performance. This amplicon contains the entire HIV-1 protease and reverse transcriptase coding region as well as the first 600 bases of integrase (FIG. 7A). Oligonucleotide sets are indicated by [open reading frame]-[codon]. Open reading frame IN refers to HIV integrase, PR to protease and RT to reverse transcriptase. Oligonucleotides were designed for 17 codons in subtype B HIV-1 Pol which confer resistance to most antiretroviral drugs. Oligonucleotide sets refer to two interrogators and one RCO. For example, PR-030 comprises the three oligonucleotides STBPR-030-GAX$_{Asp/Glu}$ (SEQ. ID. NO. 14), STBPR-030-AAX$_{Lys/Asn}$ (SEQ. ID. NO. 13) and STBPR-030-XXT (SEQ. ID. NO. 64). HIV-1 integrase codon 148 is the sole exception. The composition of each of the oligonucleotide sets used for each gene-codon is listed in Table 4.

TABLE 4

| Gene-Codon # | Interrogator Oligonucleotides (SEQ. ID. NOS.) | Reporter Capture Oligonucleotide (SEQ. ID. NO.) |
| --- | --- | --- |
| PR-030 | 13, 14 | 64 |
| PR-054 | 15, 16 | 58 |
| PR-082 | 17, 18 | 59 |
| PR-084 | 19, 20 | 53 |
| PR-088 | 21, 22 | 66 |
| RT-065 | 23, 24 | 55 |
| RT-074 | 25, 26 | 50 |
| RT-075 | 27, 28 | 56 |
| RT-103 | 29, 30 | 68 |
| RT-103b | 31, 32 | 68 |
| RT-151 | 33, 34 | 61 |
| RT-181 | 35, 36 | 67 |
| RT-184 | 37, 38 | 51 |
| RT-188 | 39, 40 | 69 |
| RT-190 | 41, 42 | 54 |
| RT-215 | 43, 44 | 60 |
| IN-148 | 45, 46, 47 | 52 |
| IN-155 | 48, 49 | 63 |

The resistance profile for this drug was not yet fully characterized. Thus, we allowed for the predominant wild type integrase codons 148 (glutamine codon CAA) and many resistance-associated codons (histidine codons CAT and CAC, lysine codon AAA and arginine codons CGA, CGC, CGT and CGG) at this site by using three interrogator oligonucleotides (STBIN-148-AAX$_{Lys/Asn}$ (SEQ. ID. NO. 45), STBIN-148-CAX$_{His/Gln}$ (SEQ. ID. NO. 46), and STBIN-148-CGX$_{Arg}$ (SEQ. ID. NO. 47)) in conjunction with three RCOs (STBIN-148-XXA, STBIN-148-XXT and STBIN-148-XXC (SEQ. ID. NOS. 52, 62 and 57, respectively). OLA was performed on serial dilutions of this amplicon to assess the performance of the prototype assay. Positions associated with resistance to protease inhibitors, nucleoside reverse transcriptase inhibitors, non-nucleoside reverse transcriptase inhibitors and integrase strand transfer inhibitors are shown. In FIG. 7B, bars reflect data from the interrogator-RCO pair which is specific to the codon shown in the first column to the right of the graph. The second and third columns on the right show the actual amplicon sequence for each codon tested. In general, most sites exhibited high correct signal. Exceptions included oligonucleotide sets for reverse transcriptase codons 74 (RT-074-TTA$_{Leu}$/RT-074-GTA$_{Val}$ (SEQ. ID. NOS. 25, 26 and 50), 188 (RT-188-TAT$_{Tyr}$/RT-188-TTA$_{Leu}$ (SEQ. ID. NOS. 39, 40 and 69) as well as those for integrase codon 155 (IN-155-AAT$_{Asn}$/IN-155-CAT$_{His}$ (SEQ. ID. NOS. 48, 49 and 63) and protease codon 30 (PR-030-GAT$_{Asp}$/PR-030-AAT$_{Asn}$ (SEQ. ID. NOS. 13, 14 and 64). Although the RT-074 oligonucleotide set (SEQ. ID. NOS. 25, 26 and 50) significantly overlaps set RT-075 (RT-075-ACA$_{Thr}$/RT-075-GTA$_{Val}$) (SEQ. ID. NOS. 27, 28 and 56), the latter gave a high correct signal, as did the oligonucleotide set RT-065 (RT-065-AAA$_{Lys}$/RT-065-AGA$_{Arg}$) (SEQ. ID. NOS. 23, 24 and 55). It is therefore unlikely that probe overlap caused the decreased performance of RT-074 oligonucleotides. Oligonucleotide sets were designed using positional base frequencies from a reference alignment, so it was possible that mismatches between the oligonucleotides and the clonal template sequence diminished reaction efficiency. Upon inspection of the control sequence, no mismatch was found in the IN-155 binding regions, but a single mismatch in the RT-074 probe binding region occurred 37 nucleotides downstream from the ligation site (in the RCO). It is unlikely that this mismatch was responsible for decreased ligation efficiency, based on previous results where mismatches closer to the ligation site had marginal impact on product formation.

FIG. 7C provides a graph that depicts an index of specificity (correct signal/incorrect signal) for each probe set as a function of clonal template input. The metric correct signal÷incorrect signal (y-axis) is used as an index of assay performance to obviate poor assay performance as a result of both low correct signal (apparent in panel B) and high incorrect signal (not apparent in panel B). Y-axis scaling for panels B and C are presented on a log$_{10}$ scale to show the range of signal amplitudes and assay specificity for each probe set.

Functional Secondary Structure Characterization

The clonal NL4-3 DNA sequence was inspected for mismatches to the remainder of our probes. Assay performance did not correspond to either the number of mismatches (few were actually found) or proximity of those mismatches to the ligation-competent site. We then analyzed problematic interrogators for secondary structure. A hairpin (ΔG≈−2.1 kcal/mol) is predicted to form at the discriminating 3'-ends of RT-188 (RT-188-TAT$_{Tyr}$/RT-188-TTA$_{Leu}$) interrogator oligonucleotides (SEQ. ID. NOS. 39 and 40), possibly accounting for the decreased ligation with oligonucleotides for reverse transcriptase codons 188 and 190 (the sequence is contained in both). A weak hairpin is predicted to form at the 3'-end of the RT-074 (RT-074-GXX$_{Val/Ala/Asp/Glu/Gly}$/RT-074-TXX$_{Phe/Leu/Ser/Tyr/STOP/Cys/Trp}$) interrogator oligonucleotides (SEQ. ID. NOS. 25 and 26) (ΔG≈−0.7 kcal/mol) and at the 3'-end of the RCO (SEQ. ID. NO. 50; ΔG≈−1.7 kcal/mol). In contrast, the IN-155-AAX$_{Lys/Asn}$ interrogator (SEQ. ID. NO. 48) is predicted to form a complex hairpin at the 5'-end with ΔG≈−1.3 kcal/mol. This hairpin, involving both the full tag sequence and some HIV sequence in the correct interrogator oligonucleotide, probably hampers bead hybridization. As we are not aware of a folding algorithm which both allows inosine residues to base pair and accounts for the 2.5 M TMAC we use in hybridizations, the negative effect of the allele-specific sequence on tag-anti-tag annealing is not yet predictable. Fortunately, we have devised a means to evaluate specific interrogator oligonucleotides using 3'-biotinylated oligonucleotides with identical sequences to the interrogators.

As a diagnostic for secondary structure, interrogator oligonucleotides PR-30-GAX$_{Asp/Glu}$, RT-74-TXX$_{Phe/Leu/Ser/Tyr/STOP/Cys/Trp}$, IN-155-AAX$_{Lys/Asn}$ and RT-188-TAT (SEQ. ID. NOS. 14, 26, 48, and 39, respectively) were synthesized with a 3'-biotin (interrogator mimic). These oligonucleotides mimic a product of an OLA in which 100% of the interrogator oligonucleotides reacted with some RCO. Interrogator mimics then allowed us to characterize how the allele-specific sequences affect bead binding without confounding factors due to incomplete ligation and RCO secondary structure in the ligated product. We also synthesized oligonucleotides (SEQ. ID. NOS. 130-133) which complement the allele-specific portion of each interrogator mimic to both determine the contribution of secondary structure and as a possible assay reagent (duplex nucleator).

Figure 8:
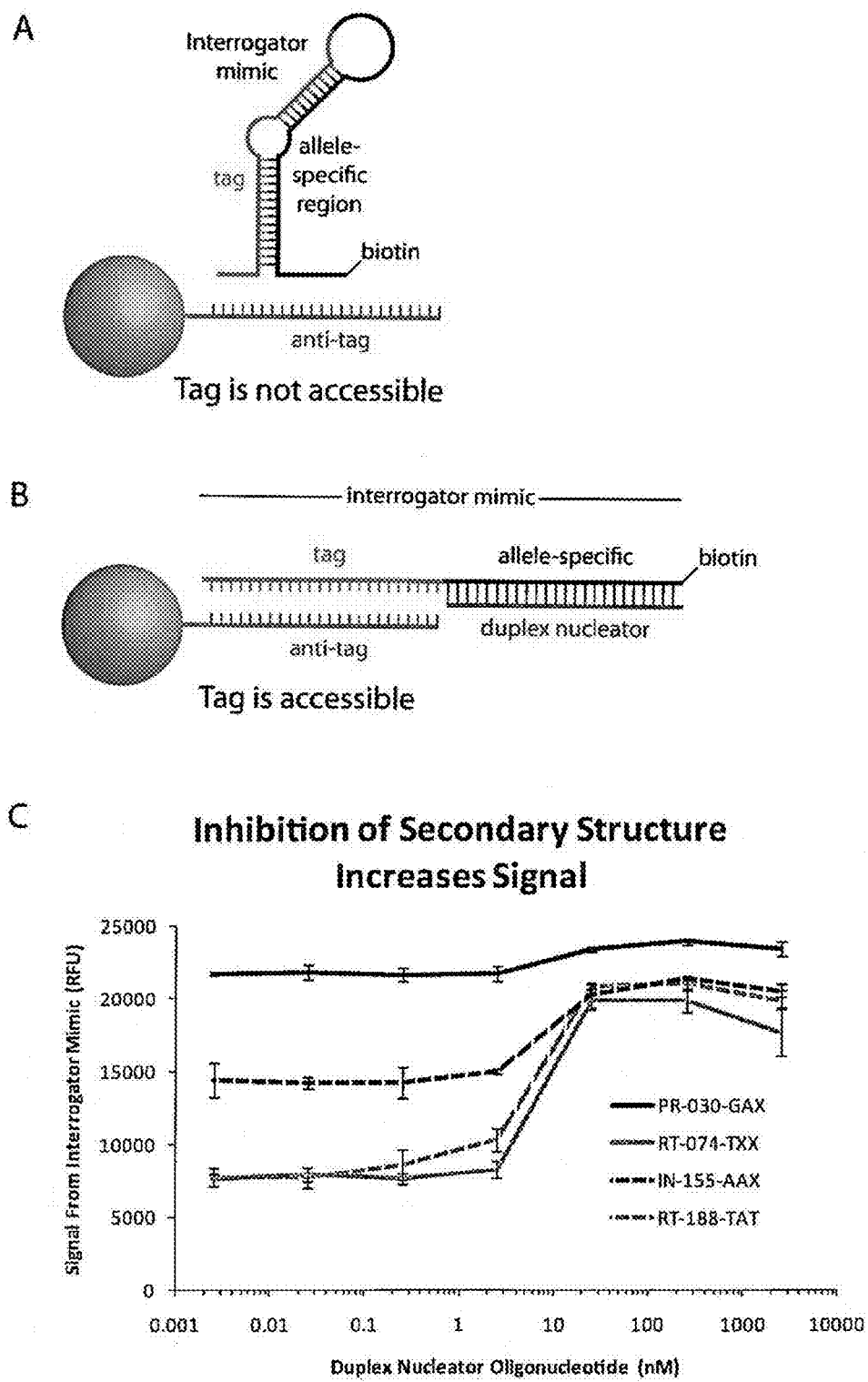
FIG. 8 shows the action of a duplex nucleator oligonucleotide. Panel A is a schematic representation of the interaction of an interrogator mimic oligonucleotide with an anti-tag sequence in the absence of a duplex nucleator oligonucleotide. Panel B is a schematic representation of the interaction of an interrogator mimic oligonucleotide with an anti-tag sequence in the presence of a duplex nucleator oligonucleotide. Panel C is a graph showing the increase in signal provided with increasing concentrations of duplex nucleator oligonucleotides.

2.5 nM each interrogator mimic and the indicated concentration of each duplex nucleator oligonucleotide (SEQ. ID. NOS. 130-133) was subjected to bead hybridization as described above (omitting competimers) and SAPE hybridization prior to detection on a flow fluorimeter. In each case, inclusion of duplex nucleator oligonucleotides in the bead hybridization step increased signal from interrogator mimics, ranging from a slight improvement (RT-030-GAX$_{Asp/Glu}$ mimic; SEQ. ID. NO. 130) to near 3-fold (RT-188-TAT$_{Tyr}$ mimic; SEQ. ID. NO. 132) as shown in FIG. 8. The effect was half-maximal at 7 nM and maximal at 100 nM (both approximate) in all cases. These results clearly indicate that secondary structure confounds suspension array detection of OLA ligation products. The presence of duplex nucleator oligonucleotides into the hybridization step of assays for minority SNPs provides an increased signal strength.

In developing suspension array assays, oligonucleotide concentration is an important factor. We have provided evidence that suspension array signal is proportional to both the absolute quantity of product formed and the fraction of reagent consumed. The optimal probe concentration for our application was approximately 7.4 nM in a 12 µl reaction volume. Template tethering was found to be a confounding factor and prevented accurate detection of minority SNPs with our assay. The confounding effects of template carryover may be the reason that no minority SNP assays are available for this platform. We have resolved this issue by including excess sense-stranded oligonucleotides in the hybridization step to compete with unligated oligonucleotides for template binding. Competimers have no effect on the specific assay signal but decrease the non-specific signal by as much as 80%. By lowering the assay background signal and standard deviation, we are able to demonstrate at least 10-fold increased sensitivity using competimer oligonucleotides. Optimized oligonucleotide concentrations and competimer oligonucleotides provided the base protocol for building an prototype assay detecting at least 13 drug resistance mutations in the HIV pol gene. We used interrogator mimics corresponding to four problematic interrogator oligonucleotides to investigate the possibility that their allele-specific sequences hamper anti-tag recognition. Allele-specific sequences in oligonucleotides do indeed interfere with bead binding, as shown using oligonucleotides which are complementary to the allele-specific sequence.

Our prototype assay demonstrates the utility of suspension array methodology for determining sequences of proximal codons in a PCR product. This is a promising methodology for determination of virus coreceptor tropism. Prior to approval of the first coreceptor antagonist, viral tropism was used to monitor HIV disease progression, but it has now become standard of care whenever a health care provider considers coreceptor antagonist rescue therapy for antiretroviral-experienced HIV+ individuals.

Example 2

The claimed invention may be demonstrated further by analyzing a sequence of HIV-1. As mentioned above, the variable subdomain 3 (V3) of glycoprotein 120 (gp120) is the main determinant of co receptor usage in HIV-1 infection of CD4+ cells. Within V3, amino acids 11 and 25 are thought to be the main determinants of HIV-1 co-receptor usage.

Similar to the assay presented above for screening drug resistance mutations in HIV-1 pol sequences, this work was initiated as a tool for evaluating a cohort of HIV+ patient isolates from the Cleveland AIDS Clinical Trials Unit (ACTU) for coreceptor tropism. Some patient isolates were chosen from the larger cohort and used for assay development.

Amino acids 11 and 25 in the HIV-1 surface glycoprotein gp120 V3 subdomain are the primary determinants of HIV-1 coreceptor usage. Clinical viral tropism is understandably a large concern for health care providers patients considering maraviroc rescue therapy for patients failing a front-line medication. Available assays for functional tropism assessment using tissue culture methods are available, but they are slow and expensive. Commercially available genetic tests are either insensitive or unreliable. Here we provide a coreceptor prediction assay based on the 11/25 rule and codon sequencing by oligonucleotide ligation, analyzed by suspension array. The causes of low performance from problematic oligonucleotides and assay bias are also discussed and minimized by the current method.

Among bioinformatic tools for tropism analysis, the 11/25 rule is one of the simplest predictors of HIV-1 coreceptor usage. This predictor is based on findings that, within the V3 sequence, amino acids 11 and 25 are highly associated with coreceptor usage. Specifically, if the identity of amino acid 11 or 25 is lysine, histidine or arginine, dual tropism is almost certain. If 11 and 25 are some amino acid other than K, H or R, it is 93%-96% probable that the isolate uses CCR5. In those recent comparative studies the predictive value of the 11/25 rule was similar to other bioinformatic predictors.

Unfortunately, 11/25 rule sensitivity estimates have been confounded by the shortcomings of Sanger sequencing. The 11/25 rule was then an attractive basis for developing a genotypic assay using ligase discrimination. Instead of considering the entire V3 sequence, implementation of the 11/25 rule only requires identification of two amino acids in V3. By using the present flow fluorimetry OLA technique, we provide a method to identify these two codons in major and minor variants without reliance on bulk DNA sequencing or cloning. Polymorphisms in V3 have been a significant challenge in development of the assay and is presumably the reason that other genotypic testing by enzymatic discrimination have not been reported. The dataset presented here demonstrates assay utility and describes principles we have used in tropism OLA (TropOLA) design and development.

Materials and Methods

Patient Samples

Seventy samples were obtained were obtained from the AIDS Clinical Trials Unit in Cleveland, Ohio in December 2007. Of these, we were able to obtain PCR product from 55. PCR-amplifiable samples had a median viral load of 11 100 and ranged from 525 to 750 000 copies HIV-1 RNA/ml patient plasma. The median CD4+T-lymphocyte count was 91 cells/ul plasma with a range of 1 to 640. Four of the PCR amplifiable samples were derived from one patient at different times during the infection. Three timepoints from each of 9 patients accounted for another 27 samples. We were able to obtain two timepoints from 8 and a single timepoint from another 8 patients. In all, the patient set represented samples from 26 patients. This study was approved by the Institutional Boards of Review at Case Western Reserve University and University Hospitals.

Template Preparation

Viral RNA was isolated from 140 µl patient plasma using the Qiagen Viral RNA mini kit according to manufacturer instructions. cDNA is generated using 5 µl of RNA extract and 5 U of SuperScript III Reverse Transcriptase following the manufacturers protocol with primer Tat13Rev (SEQ. ID. NO. 134). Five microliters patient-derived cDNA is then amplified by 5 U of Platinum Taq DNA polymerase (Invitrogen) in a 50 µl reaction volume with the buffer supplied by the manufacturer. Primers envB (SEQ. ID. NO. 136) and ED14 (SEQ. ID. NO. 135) were used for first round PCR (1.7 kb product). First round amplicons were PCR amplified in a second round using primers E80 (SEQ. ID. NO. 137) and E125 ((SEQ. ID. NO. 138); all 0.5 µM final), yielding a 480 bp product. Both PCR amplifications were performed by thermal cycling using the following conditions: 95° C. for 2 minutes followed by 35 cycles of 95° C. for 30 seconds, 45° C. for 30 seconds and 72° C. for 1 minute. The final PCR products are separated on 1% agarose to verify a single, distinct band migrating between 400 and 500 nt. Positive reactions (by visual inspection of gel banding) were purified using Qiagen PCR cleanup kit and quantified by the Quant-It PicoGreen assay (Invitrogen) according to manufacturer instructions on a Perkin-Elmer Victor3 fluorescent plate reader. PCR products were diluted to a concentration of 2 ng/ul prior to OLA.

Frequency Analysis

Oligonucleotides were designed based on a curated collection of subtype B HIV-1 sequences maintained at Los Alamos National Laboratory trimmed to the V3 region accessed on 24 Apr. 2008. Although an effort was made to include as many sequences as possible from this collection, some problematic sequences were omitted from the analysis. In particular, V3 sequences containing premature stop codons were assumed to represent defective viruses (with truncated envelope glycoproteins) and discarded. Additional details are provided below (Results).

Interrogator and Reporter Capture Oligonucleotide Design

Non-standard sequences calculated with 5-50% cutoffs were aligned in BioEdit, giving us a group of sequences from which the primer sequence was chosen. Interrogator oligonucleotides were designed from this alignment such that each oligonucleotide contained a "reasonable" number of non-standard bases. In most cases, the 15% cutoff was used. These oligonucleotides terminated at the 3' with the first two bases of either codon 11 or codon 25. Unrelated tag sequences were then amended to interrogator oligonucleotides such that each codon specificity was associated with an unique tag sequence. All reporter capture oligonucleotides terminate at the 5' with the last base of either codon 11 or codon 25. For both interrogator and reporter capture oligonucleotides, length was determined by an arbitrary goal annealing temperature of 74° C. such that multiple mismatches not accounted for by non-standard bases might be tolerated. Competimer oligonucleotides were designed using the degenerate sequence output from the frequency analysis with a 10% cutoff. Competitors V3-11-COMP (SEQ. ID. NO. 84) and V3-25-COMP (SEQ. ID. NO. 85) anneal to the same region as the codon 11 and codon 25 RCOs, respectively, with homology extended by approximately 10 bases relative to RCOs (Table 3). Table 5 provides the sequences of the interrogator oligonucleotides used in the following reactions. Table 6 provides the reporter capture oligonucleotides (all 5'-phosphate and 3'-biotin) used in the following reactions. Table 7 provides various the sequences of various sample amplification, site directed mutagensis and duplex nucleator oligonucleotides.

TABLE 5

Interrogator Oligonucleotides

| Seq. ID No. | Oligonucleotide Name | Oligonucleotide Sequence | Bead Association |
|---|---|---|---|
| 86 | V3-11b-AAX | CTTTATCAATACATACTACAATCAGAAUGAAUCT GTAIUAATTAATTGTACAAGACCCAICAACAATA CAAGAAAAAA | LUA-002 |
| 87 | V3-11b-AGX | CTTTAATCTCAATCAATACAAATCGAAUGAAUCT GTAIUAATTAATTGTACAAGACCCAICAACAATA CAAGAAAAAG | LUA-001 |
| 88 | V3-11b-CAX | AATCCTTTTACATTCATTACTTACGAAUGAAUCT GTAIUAATTAATTGTACAAGACCCAICAACAATA CAAGAAAACA | LUA-008 |
| 89 | V3-11b-CGX | TACATTACCAATAATCTTCAAATCGAAUGAAUCT GTAIUAATTAATTGTACAAGACCCAICAACAATA CAAGAAAACG | LUA-004 |
| 90 | V3-11b-GAX | CAATTCAAATCACAATAATCAATCGAAUGAAUCTG AIUAATTAATTGTACAAGACCCAICAACAATACAA AAAAGA | LUA-005 |
| 91 | V3-11b-GGX | TACACTTTATCAAATCTTACAATCGAAUGAAUCT GTAIUAATTAATTGTACAAGACCCAICAACAATA CAAGAAAAGG | LUA-003 |
| 92 | V-25a-AAX | CAATTCATTTACCAATTTACCAATACAATACAAG AAAAAGTATAUUTATIGGACCAGGGAGAGCATTT TUTICAACAGGAAA | LUA-007 |
| 93 | V3-25a-ACX | CTTTCTATCTTTCTACTCAATAATACAATACAAGA AAGTATAUUTATIGGACCAGGGAGAGCATTTTUT CAACAGGAAC | LUA-094 |
| 94 | V3-25a-AGX | TCAACAATCTTTTACAATCAAATCACAATACAAG AAAAGTATAUUTATIGGACCAGGGAGAGCATTT TUTICAACAGGAAG | LUA-006 |
| 95 | V3-25a-CCX | ATACTAACTCAACTAACTTTAAACACAATACAAG AAAAGTATAUUTATIGGACCAGGGAGAGCATTTT TICAACAGGACC | LUA-096 |
| 96 | V3-25a-CGX | AATCTCATAATCTACATACACTATACAATACAAG AAAAGTATAUUTATIGGACCAGGGAGAGCATTT TUTICAACAGGACG | LUA-097 |
| 97 | V3-25a-GAX | AATCATACTCAACTAATCATTCAAACAATACAAG AAAAGTATAUUTATIGGACCAGGGAGAGCATTT TUTICAACAGGAGA | LUA-098 |
| 98 | V3-25a-GCX | AATCTACACTAACAATTTCATAACACAATACAAG AAAAGTATAUUTATIGGACCAGGGAGAGCATTT TUTICAACAGGAGC | LUA-099 |
| 99 | V3-25a-GGX | CTATCTTTAAACTACAAATCTAACACAATACAAG AAAAGTATAUUTATIGGACCAGGGAGAGCATTT TUTICAACAGGAGG | LUA-100 |

TABLE 5-continued

Interrogator Oligonucleotides

| Seq. ID No. | Oligonucleotide Name | Oligonucleotide Sequence | Bead Association |
|---|---|---|---|
| 100 | V3-25a-CAX | TACACTTTAAACTTACTACACTAAACAATACAA GAAAAAGTATAUUTATIGGACCAGGGAGAGCAT TTTUTICAACAGGACA | LUA-095 |

TABLE 6

Reporter Capture Oligonucleotides (RCOs)

| Seq. ID No. | Oligonucleotide Name | Oligonucleotide Sequence |
|---|---|---|
| 101 | V3-11c-XXA | ADTAHHTATRGGACCAGGGAGARCATTTTATVCAACAG GAGAVATAATAGGAGATATAAGAMAAGC |
| 102 | V3-11c-XXC | CDTAHHTATRGGACCAGGGAGARCATTTTATVCAACAG GAGAVATAATAGGAGATATAAGAMAAGC |
| 103 | V3-11c-XXG | GDTAHHTATRGGACCAGGGAGARCATTTTATVCAACAG GAGAVATAATAGGAGATATAAGAMAAGC |
| 104 | V3-11c-XXT | TDTAHHTATRGGACCAGGGAGARCATTTTATVCAACAG GAGAVATAATAGGAGATATAAGAMAAGC |
| 105 | V3-11d-XXA | ADTAHHTATRGGACCAGGGAGARCATTTTATACAGGAG AVATAATAGGAGATATAAGAMAAGC |
| 106 | V3-11d-XXC | CDTAHHTATRGGACCAGGAGGARCATTTTATACAGGAG AVATAATAGGAGATATAAGAMAAGC |
| 107 | V3-11d-XXG | GDTAHHTATRGGACCAGGGAGARCATTTTATACAGGAG AVATAATAGGAGATATAAGAMAAGC |
| 108 | V3-11d-XXT | TDTAHHTATRGGACCAGGGAGARCATTTTATACAGGAG AVATAATAGGAGATATAAGAMAAGC |
| 109 | V3-11e-XXA | ADTAHHTATRGGACCAGGGAGARCATTTTATVCAACAG AVATAATAGGAGATATAAGAMAAGC |
| 110 | V3-11e-XXC | CDTAHHTATRGGACCAGGGAGARCATTTTATVCAACAG AVATAATAGGAGATATAAGAMAAGC |
| 111 | V3-11e-XXG | GDTAHHTATRGGACCAGGGAGARCATTTTATVCAACAG AVATAATAGGAGATATAAGAMAAGC |
| 112 | V3-11e-XXT | TDTAHHTATRGGACCAGGGAGARCATTTTATVCAACAG AVATAATAGGAGATATAAGAMAAGC |
| 113 | V3-25b-XXA | ARBAATAGGARATATAAGAMAAGCAYATTGTAAYMTTA RTRRARCAVANTGGRATRACACT |
| 114 | V3-25b-XXC | CRBAATAGGARATATAAGAMAAGCAYATTGTAAYMTTA RTRRARCAVANTGGRATRACACT |
| 115 | V3-25b-XXG | GRBAATAGGARATATAAGAMAAGCAYATTGTAAYMTTA RTRRARCAVANTGGRATRACACT |
| 116 | V3-25b-XXT | TRBAATAGGARATATAAGAMAAGCAYATTGTAAYMTTA RTRRARCAVANTGGRATRACACT |
| 117 | V3-25c-XXA | ARBAATAGGARATATAAGAGCAYATTGTAAYMTTARTR RARCAVANTGGRATRACACT |
| 118 | V3-25c-XXC | CRBAATAGGARATATAAGAGCAYATTGTAAYMTTARTRR ARCAVANTGGRATRACACT |
| 119 | V3-25c-XXG | GRBAATAGGARATATAAGAGCAYATTGTAAYMTTARTR RARCAVANTGGRATRACACT |
| 120 | V3-25c-XXT | TRBAATAGGARATATAAGAGCAYATTGTAAYMTTARTR RARCAVANTGGRATRACACT |

TABLE 7

Other Oligonucleotides

| Seq. ID No. | Oligonucleotide Name | Oligonucleotide Sequence | Purpose† |
|---|---|---|---|
| 121 | RTS1 | TAAACAATGGCCATTGACAGAAGA | PCR |
| 122 | RTS2 | TCAAAAATTGGGCCTGAAAATCCAT | PCR |
| 123 | RTA8 | GCTATTAAGTCTTTTGATGGGTCAT | PCR |
| 124 | RTA9 | TAAATTTAGGAGTCTTTCCCCATA | PCR |
| 125 | Mut103stC | TTAGGAATACCACACCCTGCAGGGTTAAAAAGAANAAATCAGT | SDM |
| 126 | Mut181stC1 | GTTAGAGCCCTTTAGAACAAAAAATCCAGAAATAGTCATCTRCCA | SDM |
| 127 | Mut181stC2 | GTTAGAGCCCTTTAGAACAAAAAATCCAGAAATAGTCATCTRTC | SDM |
| 128 | ML-gag-F3 | GGACAYCAAATGAAAGATTGYACTGARAGACAGGC | PCR |
| 129 | ML-int-R2 | CCCCCCTTTTCTTTTAAAATTGTGRATGAATACTGCC | PCR |
| 130 | PR-030-DN1 | NATCTGCTCCTGTATCTAATAGAGCTTCCTTTAGCTGCCC | DN |
| 131 | RT-074-DN1 | NTTTTCTCCATTTAGTACTGTCTTTTTTCTTTATGGCAAATAC | DN |
| 132 | RT-188-DN1 | NCAAATCATCCATGTATTGATAGATAACTATATCTGGATTTTG | DN |
| 133 | IN-155-DN1 | NCATAGATTCTACTACTCCTTGACTTTGGGGATTGTAGGGAAT | DN |
| 134 | Tat13Rev | GAGGGCTTCCCACCCCCTGCGT | RT |
| 135 | ED14 | TCTTGCCTGGAGCTGTTTGATGCCCCAGAC | PCR |
| 136 | ENVB | AGAAAGAGCAGAAGACAGTGGCAATGA | PCR |
| 137 | E80 | CCAATTCCCATACATTATTGTG | PCR |
| 138 | E125 | CAATTTCTGGGTCCCCTCCTGAGG | PCR |

†SDM = site-directed mutagenesis
RT = cDNA synthesis (reverse transcription)
DN = duplex nucleator oligonucleotide
PCR = polymerase chain reaction primer Ligase Detection Reactions Each LDR contains 15 mM Tris-HCl (pH 8.3), 0.06% Triton X-100, 1.0 mM dithiothreitol, 40 mM KCl, 7.5 mM MgCl$_2$, 0.3 mM NADH, 0.08% PEG 6000, 5 units Ampligase (Epicentre Biotechnologies), 2.5 fmol each up-stream oligonucleotide (Table 5) and 25 fmol of the appropriate down-stream oligonucleotides (Table 6) in a 12 µl reaction. In other words, each of SEQ. ID. NOS. 86-91 was reacted individually with each of SEQ. ID. NOS. 101-112 for V3 codon 11, and each of SEQ. ID. NOS. 92-100 was reacted individually with each of SEQ. ID. NOS. 113-120. Reactions were subjected to 300 cycles of 95° C. for 10 seconds and 37° C. for 40 seconds.

Hybridization And Detection

After thermal cycling is complete, 12 µl LDR is combined with 60 µl hybridization buffer containing 750 beads (of each appropriate region), 50 pmol of the appropriate competimer in 2 M tetramethyl ammonium chloride (TMAC), 0.01% SDS, 50 mM Tris-HCl (pH 8.0) and 3 mM EDTA. The bead hybridization reactions are subjected to 95° C. for 5 minutes followed by 37° for 60 minutes. One hundred nanograms streptavidin-phycoerythrin conjugate (SAPE; Invitrogen) is then added to the reactions, which are subjected to another 60 minutes at 37° C. Reactions are analyzed on a Luminex 200 flow fluorimeter.

Results

Reference Alignment Frequency Analysis and Probe Design

The 2007 curated alignment of 1696 HIV-1 sequences was obtained from the Los Alamos National Laboratory HIV sequence database. Curated web alignments from this source are a collection of sequences assembled to represent the sequence diversity in the much larger database. All subtype B sequences were extracted from the curated alignment and trimmed to nucleotides 7079-7244 (HXB2 numbering), a fragment which includes the coding sequence for the envelope V3 subdomain flanked by the last ten codons for constant subdomain 2 and the first ten codons for constant subdomain 3. Sequences containing premature stop codons were discarded, leaving 243 subtype B sequences. All gaps were removed and translated sequences (to preserve codon base adjacency) were re-aligned using ClustalW 2.0 (http://www.clustal.org). Some sequences then required manual alignment, where gaps occurred between or adjacent to two similar amino acids, according to nucleotide sequence homology. The resulting diversity is summarized in FIG. 9.

Figure 9:
FIG. 9 provides WebLogo (http://weblogo.berkeley.edu) output representing the diversity in the reference alignment. Codons for the initial and final V3 cysteine codons (1 and 35, respectively) are circumscribed and labeled. Nucleotides are numbered according to the HIV-1 reference strain HXB2 numbering system) Text below nucleotide numbers represent the TropOLA probe sequences. Codon specificities conferred by the 3'-terminal dinucleotide and 5'-terminal nucleotide of the interrogator and RCO, respectively, have been omitted to show only the universal sequences which are common among interrogators and RCOs. (A) Universal V3 codon 11 interrogator (nt 7088-7139, SEQ ID NOS: 86-91) and RCO (nt 7143-7207, SEQ ID NOS: 101-112) sequences. (B) Universal V3 codon 25 interrogator (nt 7126-7182, SEQ ID NOS: 92-100) and RCO (nt 7186-7144, SEQ ID NOS: 113-120) sequences.

In FIG. 9, WebLogo (http://weblogo.berkeley.edu) output representing the diversity in the reference alignment is provided. Codons for the initial and final V3 cysteine codons (1 and 35, respectively) are circumscribed and labeled. Nucleotides are numbered according to the HIV-1 reference strain HXB2 numbering system) Text below nucleotide numbers represent the TropOLA probe sequences. Codon specificities conferred by the 3'-terminal dinucleotide and 5'-terminal nucleotide of the interrogator and RCO, respectively, have been omitted to show only the universal sequences which are common among interrogators and RCOs. Panel A provides universal V3 codon 11 interrogator (nt 7088-7139, SEQ ID NOS: 86-91) and RCO (nt 7143-7207, SEQ ID NOS: 101-112) sequences. Panel B provides universal V3 codon 25 interrogator (nt 7126-7182, SEQ ID NOS: 92-100) and RCO (nt 7186-7144, SEQ ID NOS: 113-120) sequences.

A consensus sequence for the entire alignment was generated with each of four threshold values: 10% 15%, 20% and 25%. For reporter capture oligonucleotide sequences, the 20% threshold degenerate sequence was trimmed at the 5'-end to either nt 7145 (the last base of V3 codon 11) or nt 7187 (the last base of V3 codon 25) and at the 3'-end such that the resulting sequence had an average annealing temperature of 74° C. in 40 mM Na$^+$ and 7.5 mM Mg$^{2+}$. Reporter capture oligonucleotides were synthesized with 5'-phosphate, 3'-biotin moieties and either Y (T and C) or R (A and G) substituted at the 5'-most base to complement the last base of any V3 codon 11 or codon 25 sequence. For competimer oligonucleotides, information from the 10% threshold sequence was trimmed to either the codon 11 or codon 25 RCO sequence, but with extended complementarity at both ends to give an average annealing temperature of approximately 84° C.

Interrogator oligonucleotides were based on the 10%, 15% and 20% threshold sequences, in which deoxyinosine was substituted for every instance of R (A and G). All other degenerate positions were replaced by deoxyuracil. Multiple thresholds were used to limit the number of non-standard bases in any sequence to five. Sequences were trimmed at the 3'-end to nt 7414 (the second base of V3 codon 11) or nt 7186 (the second base of V3 codon 25) and at the 5'-end for an annealing temperature of 74° C. The interrogator oligonucleotide penultimate and 3'-terminal base identities were determined by the codon base inventory (below). Tag sequences were selected from a list of those available for capture by the bead manufacturer and appended to the 5'-end of each interrogator oligonucleotide.

Codon Base Inventory

All interrogator oligonucleotides specify the first two bases of either codon 11 or 25. Thus, 16 interrogator oligonucleotides would be required to probe for the 64 possible codons. We took an inventory of every base which occurred in the frequency analysis. Ten different codons and 22 different codons were discovered at the 11 and 25 positions, respectively, of the envelope V3 subdomain in our reference alignment (N=243 sequences). Codon frequencies for V3 codon 11 are provided in Table 8 and codon frequencies for V3 codon 25 are provided in Table 9, below. To eliminate those codons with low representation, we imposed a cutoff of 0.5%, functionally ignoring codon bases which are unique in the alignment. All four bases were represented in the first position of V3 codon 11 with no cutoff, but T was present in only one (0.4%) of the 243 sequences used for frequency calculation. G, A and C occurred at the second base of codon 11 but C was represented in a single sequence and omitted. Six of a possible 16 interrogator oligonucleotides were necessary for detection of codon 11 (see Table 5, SEQ. ID. NOS. 86-91). In codon 25, we discovered the absence of thymidine at the first two base positions, justifying omission of seven interrogator oligonucleotides out of the 16 possible; those with T as either the penultimate or 3'-terminal bases. Although we also imposed a 0.5% cutoff on codon 25 representation, we accounted for all codons occurring at this site because infrequent codons were not unique in the first two bases.

TABLE 8

Codon Frequency - V3 Codon 11

| Codon | Frequency (percent) |
|---|---|
| AGT | 67.1 |
| GGT | 20.3 |
| AGG | 4.9 |
| AGC | 3.7 |
| CGT | 2.4 |
| GGC | 0.4 |
| GGG | 0.4 |
| GCT | 0.4 |
| TGG | 0.4 |

TABLE 9

Codon Frequency - V3 Codon 25

| Codon | Frequency (percent) |
|---|---|
| GAA | 30.2 |
| GAC | 20.3 |
| GAT | 10.9 |
| CAA | 9.7 |
| AAA | 4.4 |
| GGA | 3.2 |
| AGA | 3.2 |
| GGC | 2.8 |
| GCA | 2.0 |
| GCC | 2.0 |
| AAT | 1.6 |
| AGC | 1.6 |
| GCT | 0.8 |
| AAC | 0.8 |
| ACA | 0.8 |
| GAG | 0.4 |
| CAG | 0.4 |
| GGG | 0.4 |
| GCG | 0.4 |
| AGG | 0.4 |
| ACC | 0.4 |
| CGA | 0.4 |

Since the interrogator oligonucleotide specifies the first two bases of each codon, the third base must be specified by the reporter capture oligonucleotide. All four bases were represented at the third position in both codons 11 and 25, so reporter capture oligonucleotides specify all four possible bases. Briefly, we designed oligonucleotides such that they abut between the second and third base of the codon. This allows for both ligase fidelity for the entire codon and assay simplicity.

OLA for V3 Codons 11 and 25 Analyzed by Flow Fluorimetry

Individual codons were identified with two-fold degeneracy by combining RCOs specifying T and C in the last base of each codon into the same reaction. A second reaction was performed by combining RCOs specifying A and G at the last base of the codon under otherwise identical conditions. Each interrogator oligonucleotide was then used twice, once for ligation to RCOs specifying a purine base and once for ligation to RCOs specifying a pyrimidine in the last codon base. For example, a first reaction contains both the interrogator V3-25-AGX (specifying A and G at the first and second codon 25 bases, respectively) and the reporter capture oligonucleotide V3-25-XXY (specifying T or C in the last base). A second reaction contains the same interrogator V3-25-AGX and RCO V3-25-XXR (specifying A or G at the last base of the codon). A template harboring codon $AGA_{Arg}$ will be identified in the second reaction, but not the first. In this case, results will not indicate whether the template harbors $AGA_{Arg}$ or $AGG_{Arg}$. However, this is not a problem because both AGA and AGG code for arginine. For most codons, transition mutations in the last nucleotide are silent. The sole exceptions are ATR ($ATA_{Ile}/ATG_{Met}$) and TGR ($TGG_{Trp}/TGA_{STOP}$) but neither involves ambiguity for positive charge assignment, so they are inconsequential for our purposes. Furthermore, $TGG_{Trp}$ may be assumed if TGR ($TGG_{Trp}/TGA_{STOP}$) is identified since this would otherwise represent a premature stop codon in the middle of the envelope ORF. In any case, we discovered no sequence which harbored any of those codons ($ATA_{Ile}$, $ATG_{Met}$, $TGG_{Trp}$ or $TGA_{STOP}$) in our reference alignment at either site.

Figure 12:
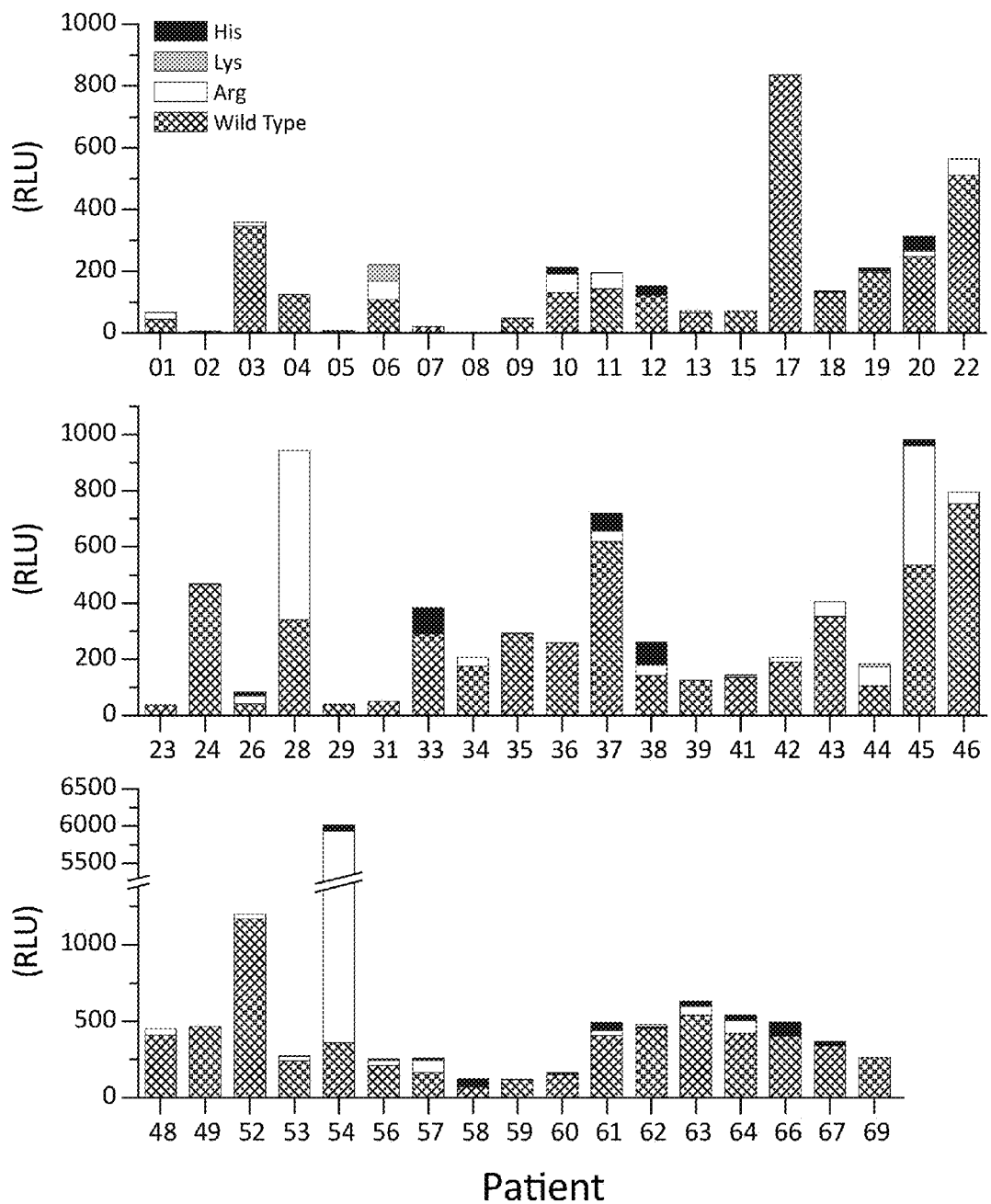
FIG. 12 is a series of bar graphs showing the distribution of codons at V3 position 11 for each patient in the study. For each patient, codon 11 was detected by TropOLA. Synonymous codons for arginine were summed. Codons for amino acids other than Arg, His and Lys are summed and reported as "wild-type". All data shown is greater than the negative control within the 95% confidence interval.

FIG. 12 shows codon 11 results from analysis of TropOLA on the 55 samples from the clinical control set. The claimed method was able to detect 11/25 rule X4 genotype in 42 of 55 samples at this site. Only sample 8 failed to give signal for any codon 11 detection and approximately half of the samples gave values lower than 250 RFU (after background correction). While this signal is low, all data shown is significant ($p<0.05$).

Figure 13:
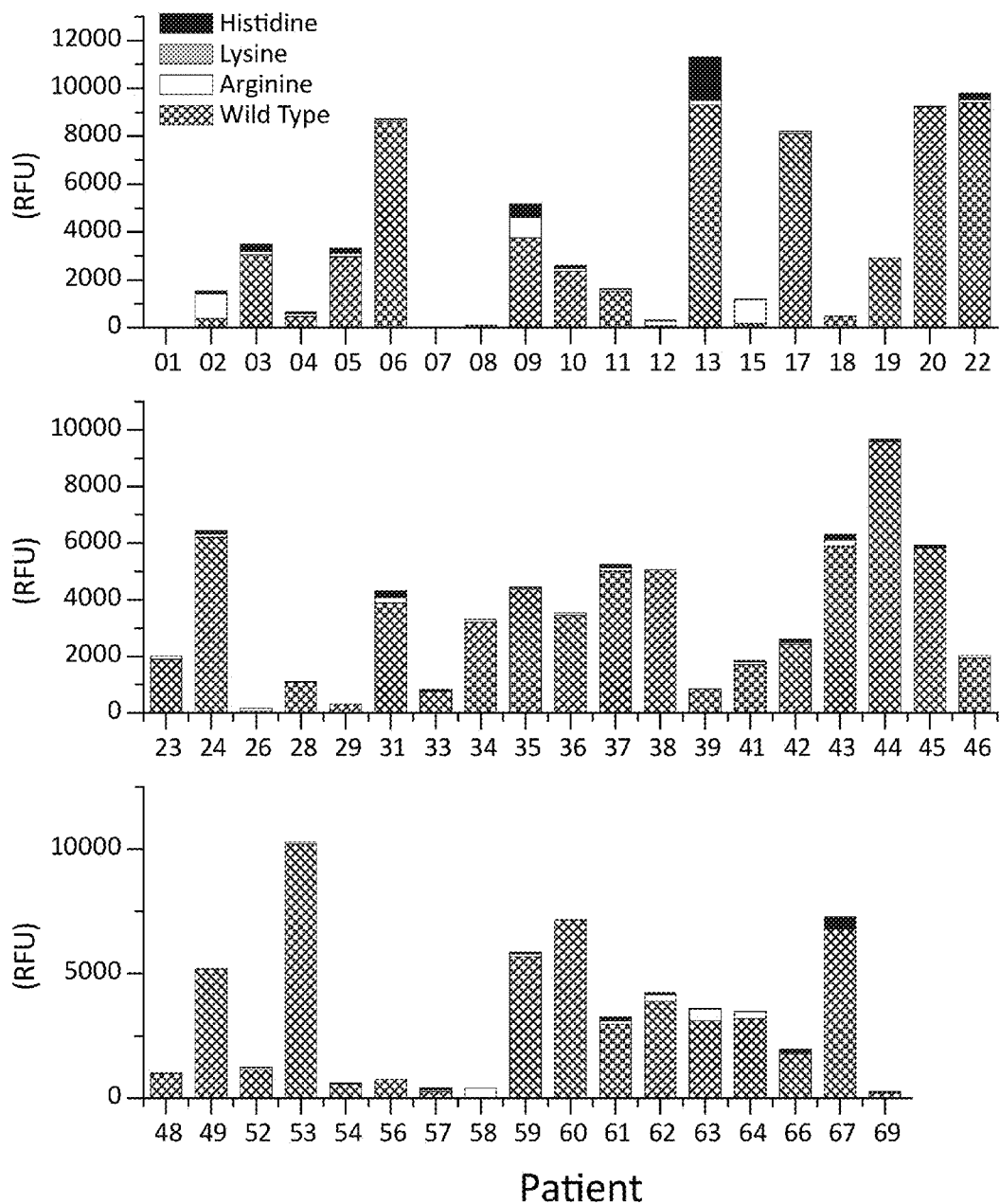
FIG. 13 is a series of bar graphs showing the distribution of codons at V3 position 25 for each patient in the study. Detections for codon 25 are in parallel to those shown in FIG. 11. Codon 25 is reported as either Lys, His or the sum of all Arg synonyms. Signal from all other codons are summed and reported as "wild-type". All data are statistically significant ($p<0.05$).

TropOLA results for codon 25 yielded much higher signal than codon 11 (FIG. 13). No actual assay failures occurred for codon 25 detections. Forty-five out of 55 samples had detectable X4-associated codons by the 11/25 rule at this site. Interesting results were obtained from sample 54 in that the signal amplitude was much higher at codon 11 than at codon 25. Sample 43 is derived from the same patient at an earlier point during infection (approximately 3 years prior), but yielded similar signal amplitude for both codons. The 35 amino acid V3 region from these two timepoints differ by nine amino acids in addition to several synonymous mutations, exemplifying the polymorphic nature of this sequence. In all, only samples 29, 39 and 49 lacked any X4-associated codon sequence by TropOLA (all different patients).

Codon 11 TropOLA Results Compared with the Dominant Sequence

Table 10 shows TropOLA results for 46 samples from which we were also able to obtain dominant DNA sequences. Amplicons from nine patients did not yield intelligible DNA sequences so, although TropOLA yielded positive results for all nine, they were omitted from the analysis since the assay data could not be compared to the dominant sequence. Table 10 column 3 shows the signal from correct interrogator oligonucleotide (i.e. the interrogator corresponding to the dominant sequence) with the correct RCO (that which also corresponded to the dominant sequence). Interrogator oligonucleotide V3-11b-$AGX_{Ser/Arg}$ (specifying A and G in the first and second codon 11 base, respectively) identified the dominant codon in 34 of 38 samples. Interrogator V3-11b-$GAX_{Asp/Glu}$ (specifying G and A in the first and second codon 11 base, respectively) was unable to identify codon $GAT_{Asp}$ in samples 4 and 8. Interrogator V3-11b-$GGX_{Gly}$ (specifying G in the first and second codon 11 bases) identified dominant codons in four of the six samples in which some codon beginning with a GG dinucleotide was dominant.

Table 10 column 4 shows the codon 11 TropOLA signal corresponding to the dominant sequence as a percentage of the signal sum from all interrogator oligonucleotides at this site. In four samples, the correct codon sequence (i.e. that which corresponded to the dominant sequence) was not identified and the dominant sequence comprised less than 50% of the total signal for an additional 10 samples. This may indicate secondary structure in the tag region of the oligonucleotide corresponding to the dominant codon. Secondary structure in any interrogator oligonucleotide would be expected to cause systematic failure with all samples in which the corresponding codon is dominant. However, these results do not indicate a systematic problem since both interrogators V3-11b-$AGX_{Ser/Arg}$ and V3-11b-$GGX_{Gly}$ correctly identified that codon in other samples. Interrogator V3-11b-$GAX_{Asp/Glu}$ seems be an exception, as it failed to identify $GAT_{Asp}$ in both samples attempted.

TABLE 10

| | | TropOLA | |
|---|---|---|---|
| Sample | Dominant Codon | Correct Signal | % of Total |
| 29 | AGA | 0.0 | 0.0 |
| 6 | AGC | 90.0 | 40.7 |
| 17 | AGC | 801.0 | 95.8 |
| 46 | AGC | 709.0 | 89.0 |
| 48 | AGC | 314.0 | 69.8 |
| 49 | AGC | 467.0 | 100.0 |
| 52 | AGC | 1061.0 | 88.4 |
| 11 | AGG | 0.0 | 0.0 |
| 28 | AGG | 602.5 | 63.9 |
| 54 | AGG | 5512.5 | 91.7 |
| 61 | AGG | 22.5 | 4.6 |
| 3 | AGT | 303.0 | 84.5 |
| 5 | AGT | 0.0 | 0.0 |
| 7 | AGT | 1.0 | 52.6 |
| 9 | AGT | 32.0 | 64.8 |
| 10 | AGT | 77.0 | 36.3 |
| 20 | AGT | 95.0 | 30.3 |
| 22 | AGT | 453.0 | 80.3 |
| 23 | AGT | 30.0 | 81.6 |
| 24 | AGT | 427.0 | 90.9 |
| 26 | AGT | 14.5 | 17.4 |
| 31 | AGT | 51.0 | 100.0 |
| 34 | AGT | 104.0 | 50.3 |
| 36 | AGT | 178.0 | 68.7 |
| 37 | AGT | 530.0 | 73.6 |
| 38 | AGT | 61.0 | 23.4 |
| 39 | AGT | 96.5 | 77.1 |
| 41 | AGT | 110.0 | 76.5 |
| 42 | AGT | 49.0 | 23.7 |
| 43 | AGT | 327.0 | 80.8 |
| 53 | AGT | 152.0 | 55.8 |
| 56 | AGT | 30.0 | 11.8 |
| 58 | AGT | 37.0 | 30.0 |
| 59 | AGT | 116.0 | 100.0 |
| 60 | AGT | 129.0 | 78.3 |
| 69 | AGT | 194.0 | 74.1 |
| 35 | AGY | 0.0 | 0.0 |
| 45 | AGY | 401.0 | 40.8 |
| 4 | GAT | 0.0 | 0.0 |
| 8 | GAT | 0.0 | 0.0 |
| 2 | GGT | 0.0 | 0.0 |

TABLE 10-continued

| | | TropOLA | |
|---|---|---|---|
| Sample | Dominant Codon | Correct Signal | % of Total |
| 13 | GGT | 42.0 | 58.6 |
| 15 | GGT | 0.0 | 0.0 |
| 18 | GGT | 132.5 | 97.8 |
| 44 | GGT | 68.5 | 37.4 |
| 63 | GGT | 53.5 | 8.5 |

Samples are demarked according to interrogator associated with dominant codon.

Codon 25 TropOLA Results Compared with the Dominant Sequence

Interrogator V3-25-AAX$_{Lys/Asn}$ (specifying A in the first two codon 25 bases) was unable to identify the correct dominant codon for any sample in the set (Table 11). Oligonucleotide V3-25-AGX$_{Ser/Arg}$ correctly identified five of six dominant codons correctly but two of these were also not identified as dominant. Interrogator V3-25-CAX$_{His/Gln}$ performed adequately in the limited number of samples available, correctly identifying the dominant codon as both present and dominant in both samples harboring CAA$_{Gln}$ at this site by bulk sequencing. Interrogator V3-25-GAX$_{Asp/Glu}$ identified the correct codon in all 25 sequences, failing to identify dominance in only three. Only sample 3 harbored GCC$_{Ala}$ at codon 25, but it was correctly identified as dominant by V3-25-GCX$_{Ala}$. Interrogator V3-25-GGX$_{Gly}$ had similar results in identifying GGA$_{Gly}$ and GGG$_{Gly}$ as dominant in one and two samples, respectively.

Figure 14:
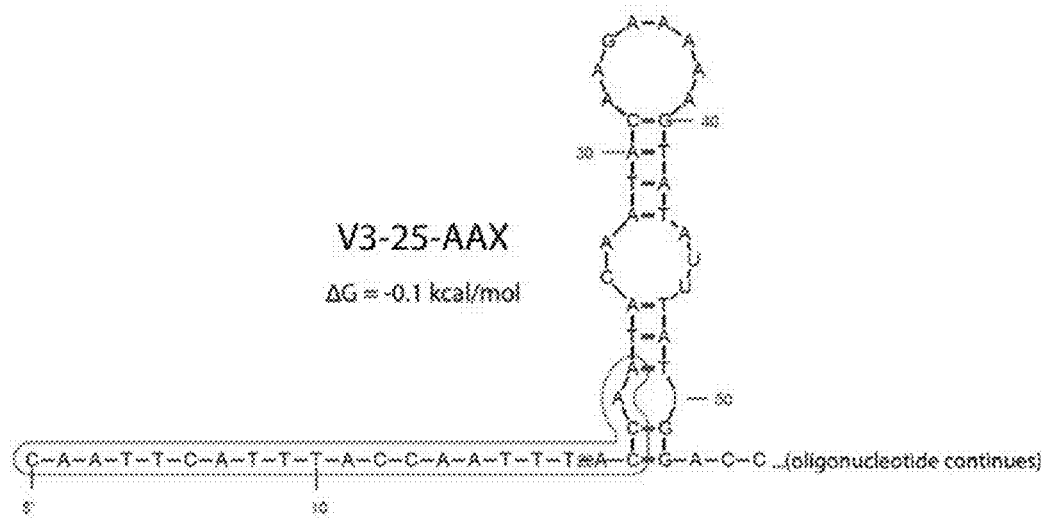
FIG. 14 provides representations of predicted hairpin structures for Interrogator Oligonucleotides V3-25-AAX$_{Lys/Asn}$ (SEQ ID NO: 92), V3-25-AGX$_{ser/Arg}$ (SEQ ID NO: 94) and V3-11b-GAX$_{Asp/Glu}$ (SEQ ID NO: 90). These were analyzed for secondary structure by the DINAMelt server (http://www.bioinfo.rpi.edu) using parameters: 40 mM Na$^+$, 7.5 mM 2+Mg$^{2+}$, 37° C. Tag sequences are circumscribed. (A) V3-25-AAX$_{Lys/Asn}$ (SEW ID NO: 90). The actual oligonucleotide sequence has been trimmed at the 3'-end. (B) V3-25-AGX$_{ser/Arg}$ (SEQ ID NO: 94). The actual oligonucleotide sequence has been trimmed at both the 5'- and 3'-end. (C) V3-11b-GAX$_{Asp/Glu}$ (SEQ ID NO: 90). Oligonucleotide sequence has been trimmed at the 3'-end.
Figure 14:
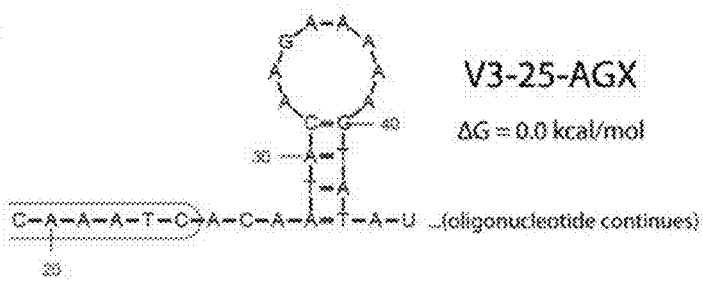
Figure 14:
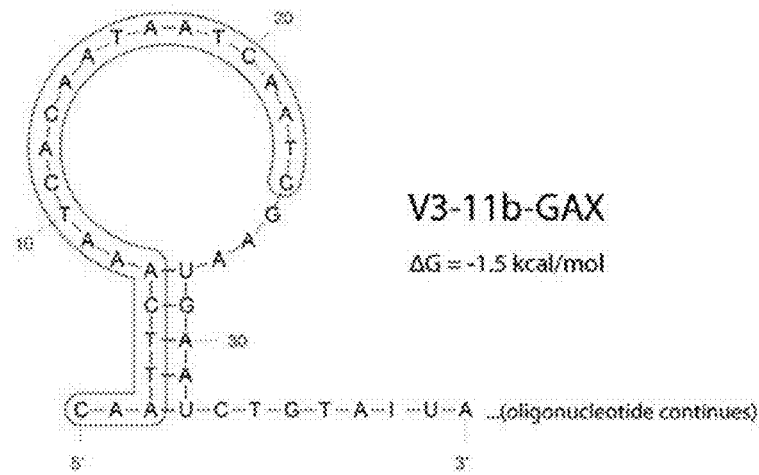

TropOLA discordance with dominant sequencing results might indicate secondary structure in oligonucleotides responsible for discordance. We have already determined that folding algorithms underestimate secondary structure in our system. Interrogators V3-25-AAX$_{Lys/Asn}$, V3-25-AGX$_{Ser/Arg}$ and V3-11b-GAX$_{Asp/Glu}$ were analyzed for secondary structure by the DINAMelt server (http://www.bioinfo.rpi.edu) using parameters: 40 mM Na$^+$, 7.5 mM Mg$^{2+}$, 37° C. FIG. 14A shows folding results for oligonucleotide V3-25-AAX$_{Lys/Asn}$. Four 3'-terminal bases in the tag sequence are involved in a stable hairpin which might inhibit the interrogator from binding to the anti-tag sequence on the bead. V3-25-AGX$_{Ser/Arg}$ has limited secondary structure involving non-tag sequence (FIG. 14B). Low signal from this interrogator cannot be directly attributed to this secondary structure because an equivalent hairpin exists in all other V3-25 interrogators. In contrast to the above V3-25 interrogators, V3-11b-GAX$_{Asp/Glu}$ was found to have extensive secondary structure involving all but the two 5' terminal bases in the tag sequence (FIG. 14C). As discussed above, DNA folding algorithms are poor predictors for secondary structure for this system. It is therefore quite probable that unpredicted secondary structure is responsible for the low signal from these problematic oligonucleotides.

TABLE 11

Comparison of TropOLA vs. Bulk sequencing for Dominant Codon

| | | TropOLA | |
|---|---|---|---|
| Sample | Dominant Codon | Correct Signal | % of Total |
| 4 | AAA | 0.0 | 0.0 |
| 7 | AAA | 0.0 | 0.0 |
| 8 | AAA | 0.0 | 0.0 |
| 26 | AAA | 0.0 | 0.0 |
| 45 | AAA | 0.0 | 0.0 |
| 61 | AAA | 0.0 | 0.0 |
| 29 | AAC | 0.0 | 0.0 |
| 54 | AAC | 0.0 | 0.0 |
| 28 | AAM* | 0.0 | 0.0 |
| 6 | GAA | 7757.3 | 88.9 |
| 10 | GAA | 2019.8 | 77.8 |
| 17 | GAA | 7704.8 | 93.7 |
| 24 | GAA | 5619.3 | 87.3 |
| 31 | GAA | 2018.8 | 46.8 |
| 34 | GAA | 2855.8 | 86.2 |
| 36 | GAA | 3123.8 | 88.5 |
| 41 | GAA | 1369.3 | 73.3 |
| 42 | GAA | 2135.8 | 82.3 |
| 44 | GAA | 5779.8 | 59.8 |
| 46 | GAA | 1558.8 | 77.1 |
| 49 | GAA | 4937.8 | 95.1 |
| 60 | GAA | 6974.3 | 97.4 |
| 5 | GAC | 2352.5 | 70.5 |
| 9 | GAC | 1026.0 | 19.8 |
| 23 | GAC | 1530 | 76.3 |
| 35 | GAC | 3935.5 | 88.5 |
| 37 | GAC | 3570.5 | 67.9 |
| 39 | GAC | 696.5 | 82.2 |
| 43 | GAC | 5235.5 | 83.0 |
| 48 | GAC | 843.5 | 83.7 |
| 52 | GAC | 882.5 | 70.3 |
| 59 | GAC | 5305.0 | 90.5 |
| 69 | GAC | 49.0 | 17.4 |
| 56 | GAG | 749.8 | 100.0 |
| 2 | AGA | 918.9 | 60.1 |
| 11 | AGA | 0.0 | 0.0 |
| 15 | AGA | 846.9 | 70.2 |
| 58 | AGA | 380.9 | 96.5 |
| 63 | AGA | 465.4 | 12.9 |
| 18 | AGC | 179.6 | 37.8 |
| 13 | CAA | 7217.9 | 63.8 |
| 22 | CAA | 7167.9 | 73.2 |
| 3 | GCC | 2020.1 | 58.1 |
| 53 | GGA | 8917.8 | 86.7 |
| 20 | GGG | 8826.8 | 95.4 |
| 38 | GGG | 2010.8 | 99.2 |

Samples are demarked according to interrogator associated with dominant codon.
*Sample 28 harbored a mixture of AAA and AAC at codon 25.

Mismatches Responsible for Low Total Signal

As indicated above, some samples were associated with lower assay performance. Tag-V3 sequence complementarity may cause decreased performance with specific interrogator oligonucleotides but probe-template mismatches may cause lower ligation efficiency in the overall set. Since probe sequences are based on positional base frequencies from a reference alignment (i.e. not our sample set), they might have less complementarity to some templates in our sample set.

To find mismatches responsible for diminished assay performance, signal amplitudes from codon 11 detections were summed for each sample and assigned to a quartile. The first quartile represents the sample subset for which overall assay performance was the lowest whereas the fourth quartile represents the sample subset for which assay performance was high. Samples in the first quartile were analyzed for mismatches within 5 codons 3' and 5' to codon 11 and compared to the same analysis for sequences comprising the fourth quartile (FIG. 15).

Three upstream mismatches (5' to the ligation site) and two downstream mismatches (3' to the ligation site) were coincident with codon 11 quartile 1 and 4. Mismatches 6, 16 and 17 bases upstream (−6, −16 and −17) as well as 7, 8, 10, 13 and 15 downstream (+7, +8, +10, +13 and +15) of the ligation site were unique to codon 11 quartile 1. Although many mismatches are associated with low assay performance, mismatches more proximal to the codon 11 ligation site (−6, +7 and +8) are more likely than others to be causative.

A similar analysis was performed for codon 25 as shown in FIG. 15B. Only two mismatches (+6 and +7) in the RCO were unique to the quartile 1 set. Codon 25 quartile 1 contained five unique upstream mismatches (−3, −4, −10, −11, −17). Two additional upstream mismatches were coincident with both quartiles and three mismatches were unique to quartile 4. Mismatches at the −3 and −5 positions were more frequent in the first quartile than with the fourth. We noticed that 3 quartile 1 samples harbored a deletion of codon 24 (Δ24) and two samples were deleted in codon 22 (Δ22; FIG. 15B). Both deletions had probably caused ligation failure. Interestingly, four of the five samples containing a deletion in this region have dominant X4-associated codon $AAA_{Lys}$ (FIG. 15C). This might account for our failure to detect some of the dominant $AAA_{Lys}$ codons at this site (Table 10).

Based upon the foregoing disclosure, it should now be apparent that the invention will carry out the aspects set forth hereinabove. It is, therefore, to be understood that any variations evident fall within the scope of the claimed invention and thus, the selection of specific component elements can be determined without departing from the spirit of the invention herein disclosed and described. While the invention has been described with reference to identification of V3 amino acids 11 and 25 involving template-dependent ligation of two oligonucleotides within V3 codon 11 and codon 25 using a thermostable ligase, the invention should not be considered to be limited thereto.

What is claimed is:

1. A method of detecting at least one single nucleotide polymorphism in a first polynucleotide sequence of a predetermined species, the method comprising:

providing a first polynucleotide to be analyzed for the presence of at least one single nucleotide polymorphism (SNP);

providing a second polynucleotide consisting of a first sequence, a second sequence adjacent to the first sequence, and a single nucleotide polymorphism interrogating position that is adjacent the second sequence distal to the first sequence, wherein the second sequence is essentially complementary to a first portion of the first polynucleotide and wherein the first sequence is not completely complementary to the first polynucleotide adjacent to the first portion of the first polynucleotide, and wherein the second polynucleotide is at least 50 nucleotides long;

providing a third polynucleotide comprising a sequence that is essentially complementary to a second portion of the first polynucleotide immediately adjacent the first portion of the first polynucleotide at a junction;

subjecting the first, second and third polynucleotides to conditions under which complementary regions of the first, second and third polynucleotides will anneal;

ligating the second and third polynucleotides at a junction between the second and third polynucleotides when no mismatches occur between the first polynucleotide and either of: the single nucleotide polymorphism interrogating position and the position in the second sequence adjacent to the single nucleotide polymorphism interrogating position; and the nucleotide of the third polynucleotide at the junction;

optionally denaturing the annealed polynucleotides and repeating the steps of subjecting the polynucleotides to conditions under which complementary regions of the polynucleotides will anneal and treating the annealed polynucleotides with a ligase a predetermined number of times;

providing a fourth polynucleotide coupled to a first detectable label, wherein the fourth polynucleotide contains a sequence that is essentially complementary to at least a portion of the first sequence of the second polynucleotide;

providing at least one of a fifth and a sixth polynucleotide, wherein the fifth polynucleotide consists of a sequence that is essentially complementary to at least a portion of the third polynucleotide sufficient to cause the fifth polynucleotide to hybridize to the third polynucleotide sequence that is essentially complementary to a second portion of the first polynucleotide but wherein the fifth polynucleotide is devoid of a sequence of about 15 or more nucleotides that are complementary to the second sequence of the second polynucleotide, and wherein the sixth polynucleotide consists of a sequence that is essentially complementary to at least a portion of the second sequence of the second polynucleotide and the single nucleotide polymorphism interrogating position sufficient to cause the sixth polynucleotide to hybridize to the second sequence of the second polynucleotide and the single nucleotide polymorphism interrogating position, but wherein the sixth polynucleotide is devoid of a sequence of about 15 or more nucleotides that are complementary to the third polynucleotide, wherein at least one of the third polynucleotide and the fifth polynucleotide is coupled to a second detectable label, and the sixth polynucleotide is not coupled to the second detectable label; and wherein each of the second, third, fourth, and fifth and sixth polynucleotides is a single-stranded polynucleotide;

subjecting the polynucleotides to conditions under which complementary regions of the polynucleotides will anneal; and detecting the presence of the first and second detectable labels.

2. The method of claim 1, wherein both a fifth polynucleotide and a sixth polynucleotide are provided.

3. The method of claim 1, wherein the first detectable label is a polymer bead having a diameter of less than 10 micrometers and containing at least one fluorophore.

4. The method of claim 3, wherein the polymer bead is a polystyrene bead.

5. The method of claim 1, wherein the first polynucleotide is a polymerase chain reaction product of a viral polynucleotide sequence.

6. The method of claim 5, wherein the viral polynucleotide sequence is from the genome of human immunodeficiency virus 1 (HIV-1).

7. The method of claim 6, wherein the viral polynucleotide sequence encodes at least a portion of the envelope glycoprotein 120 (gp120) coding region.

8. The method of claim 7, wherein the viral polynucleotide sequence includes at least one of amino acid 11 and amino acid 25 of variable subdomain 3 (V3).

9. A kit for detecting at least one single nucleotide polymorphism in a first polynucleotide sequence of a predetermined species, the kit comprising:

a second polynucleotide consisting of a first sequence, a second sequence adjacent to the first sequence, and a single nucleotide polymorphism interrogating position that is adjacent the second sequence distal to the first sequence, wherein the second sequence is essentially complementary to a first portion of the first polynucleotide and wherein the first sequence is not completely complementary to the first polynucleotide adjacent to the first portion of the first polynucleotide, and wherein the second polynucleotide is at least 50 nucleotides long;

a third polynucleotide comprising a sequence that is essentially complementary to a second portion of the first polynucleotide immediately adjacent the first portion of the first polynucleotide at a junction;

a fourth polynucleotide coupled to a first detectable label, wherein the fourth polynucleotide is essentially complementary to the first sequence of the second polynucleotide; and at least one of a fifth and a sixth polynucleotide, wherein the fifth polynucleotide consists of a sequence that is essentially complementary to at least a portion of the third polynucleotide sufficient to cause the fifth polynucleotide to hybridize to the third polynucleotide sequence that is essentially complementary to a second portion of the first polynucleotide but wherein the fifth polynucleotide is devoid of a sequence of about 15 or more nucleotides that are complementary to the second sequence of the second polynucleotide, and wherein the sixth polynucleotide consists of a sequence that is essentially complementary to at least a portion of the second sequence of the second polynucleotide and the single nucleotide polymorphism interrogating position sufficient to cause the sixth polynucleotide to hybridize to the second sequence of the second polynucleotide and the single nucleotide polymorphism interrogating position, but wherein the sixth polynucleotide is devoid of a sequence of about 15 or more nucleotides that are complementary to the third polynucleotide;

wherein at least one of the third polynucleotide and the fifth polynucleotide—is coupled to a second detectable label, and the sixth polynucleotide is not coupled to the second detectable label; and wherein each of the second, third, fourth, and fifth and sixth polynucleotides is a single-stranded polynucleotide.

10. The kit according to claim 9, wherein both a fifth and a sixth polynucleotide are provided.

11. The kit according to claim 10, wherein the second detectable label is a biotin molecule.

12. The kit according to claim 10, wherein the first detectable label is a polymer bead having a diameter of less than 10 micrometers and containing at least one fluorophore.

13. The kit according to claim 12, wherein the polymer bead is a polystyrene bead.

14. The kit according to claim 9, wherein the second sequence of the second polynucleotide is essentially complementary to a first portion of a viral polynucleotide sequence and the third polynucleotide is essentially complementary to a second portion of the viral polynucleotide sequence immediately adjacent the first portion of the viral polynucleotide sequence.

15. The kit according to claim 14, wherein the viral polynucleotide sequence is a polynucleotide sequence of human immunodeficiency virus 1 (HIV-1).

16. The kit according to claim 15, wherein the viral polynucleotide sequence encodes at least a portion of the envelope glycoprotein 120 (gp 120) coding region.

17. The kit according to claim 16, wherein the viral polynucleotide sequence encodes at least one of amino acid 11 and amino acid 25 of variable subdomain 3 (V3).

18. The kit according to claim 17, additionally comprising a ligase.

19. The kit according to claim 13, additionally comprising a ligase.

20. The kit according to claim 9, wherein the first and second detectable labels are each selected from the group consisting of a polymer bead, a biotin molecule, a fluorescent molecule and a magnetic bead.

21. The kit according to claim 9, wherein the second polynucleotide is selected from the group consisting of SEQ ID NOS: 1-49.

22. The kit according to claim 21, wherein the third polynucleotide is selected from the group consisting of SEQ ID NOS: 50-72.

* * * * *

SEQUENCE LISTING

<160> NUMBER OF SEQ ID NOS: 138

<210> SEQ ID NO 1
<211> LENGTH: 60
<212> TYPE: DNA
<213> ORGANISM: Artificial
<220> FEATURE:
<223> OTHER INFORMATION: Tag sequence + HIV-1 sequence

<400> SEQUENCE: 1
tatactatca actcaacaac atatttagga ataccacacc ctgcagggtt aaaaaagaat     60

<210> SEQ ID NO 2
<211> LENGTH: 60
<212> TYPE: DNA
<213> ORGANISM: Artificial
<220> FEATURE:
<223> OTHER INFORMATION: Tag sequence + HIV-1 sequence

<400> SEQUENCE: 2
ctacaaacaa acaaacatta tcaattagga ataccacacc ctgcagggtt aaaaaagaac     60

<210> SEQ ID NO 3
<211> LENGTH: 60
<212> TYPE: DNA
<213> ORGANISM: Artificial
<220> FEATURE:
<223> OTHER INFORMATION: Tag sequence + HIV-1 sequence

<400> SEQUENCE: 3
atactacatc ataatcaaac atcattagga ataccacacc ctgcagggtt aaaaaagaaa     60

<210> SEQ ID NO 4
<211> LENGTH: 60
<212> TYPE: DNA
<213> ORGANISM: Artificial
<220> FEATURE:
<223> OTHER INFORMATION: Tag sequence + HIV-1 sequence

<400> SEQUENCE: 4
caattcaaat cacaataatc aatcttagga ataccacacc ctgcagggtt aaaaaagaag     60

<210> SEQ ID NO 5
<211> LENGTH: 60
<212> TYPE: DNA
<213> ORGANISM: Artificial
<220> FEATURE:

<223> OTHER INFORMATION: Tag sequence + HIV-1 sequence
<220> FEATURE:
<221> NAME/KEY: misc_feature
<222> LOCATION: (39)..(42)
<223> OTHER INFORMATION: n is deoxyuracil
<220> FEATURE:
<221> NAME/KEY: misc_feature
<222> LOCATION: (48)..(48)
<223> OTHER INFORMATION: n is deoxyinosine
<220> FEATURE:
<221> NAME/KEY: misc_feature
<222> LOCATION: (55)..(55)
<223> OTHER INFORMATION: n is deoxyuracil

<400> SEQUENCE: 5
tatactatca actcaacaac atatttagga ataccacanc cngcaggntt aaaanagaat    60

<210> SEQ ID NO 6
<211> LENGTH: 60
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (39)..(42)
<223> OTHER INFORMATION: n is deoxyuracil
<220> FEATURE:
<221> NAME/KEY: misc_feature
<222> LOCATION: (48)..(48)
<223> OTHER INFORMATION: n is deoxyinosine
<220> FEATURE:
<221> NAME/KEY: misc_feature
<222> LOCATION: (55)..(55)
<223> OTHER INFORMATION: n is deoxyuracil

<400> SEQUENCE: 6
ctacaaacaa acaaacatta tcaattagga ataccacanc cngcaggntt aaaanagaac    60

<210> SEQ ID NO 7
<211> LENGTH: 60
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (39)..(42)
<223> OTHER INFORMATION: n is deoxyuracil
<220> FEATURE:
<221> NAME/KEY: misc_feature
<222> LOCATION: (48)..(48)
<223> OTHER INFORMATION: n is deoxyinosine
<220> FEATURE:
<221> NAME/KEY: misc_feature
<222> LOCATION: (55)..(55)
<223> OTHER INFORMATION: n is deoxyuracil

<400> SEQUENCE: 7 atactcatc ataatcaaac atcattagga ataccacanc cngcaggntt aaaanagaaa    60

<210> SEQ ID NO 8
<211> LENGTH: 60
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (39)..(42)
<223> OTHER INFORMATION: n is deoxyuracil
<220> FEATURE:
<221> NAME/KEY: misc_feature
<222> LOCATION: (48)..(48)
<223> OTHER INFORMATION: n is deoxyinosine
<220> FEATURE:
<221> NAME/KEY: misc_feature
<222> LOCATION: (55)..(55)
<223> OTHER INFORMATION: n is deoxyuracil

<400> SEQUENCE: 8
caattcaaat cacaataatc aatcttagga ataccacanc cngcaggntt aaaanagaag    60

<210> SEQ ID NO 9
<211> LENGTH: 76
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (35)..(43)
<223> OTHER INFORMATION: n is deoxyuracil
<220> FEATURE:
<221> NAME/KEY: misc_feature
<222> LOCATION: (49)..(50)
<223> OTHER INFORMATION: n is deoxyinosine
<220> FEATURE:
<221> NAME/KEY: misc_feature
<222> LOCATION: (51)..(70)
<223> OTHER INFORMATION: n is deoxyuracil

<400> SEQUENCE: 9 aatccttta cattcattac ttacgacaaa aatcntagag ccntttagnn nanaaaancc     60
aganatagtn atctgt                                                   76

<210> SEQ ID NO 10
<211> LENGTH: 76
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (35)..(43)
<223> OTHER INFORMATION: n is deoxyuracil
<220> FEATURE:
<221> NAME/KEY: misc_feature
<222> LOCATION: (49)..(50)
<223> OTHER INFORMATION: n is deoxyinosine
<220> FEATURE:
<221> NAME/KEY: misc_feature
<222> LOCATION: (51)..(70)
<223> OTHER INFORMATION: n is deoxyuracil

<400> SEQUENCE: 10
aaacaaactt cacatctcaa taatgacaaa aatcntagag ccntttagnn nanaaaancc    60
aganatagtn atctgc                                                   76

<210> SEQ ID NO 11
<211> LENGTH: 76
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (35)..(43)
<223> OTHER INFORMATION: n is deoxyuracil
<220> FEATURE:
<221> NAME/KEY: misc_feature
<222> LOCATION: (49)..(50)
<223> OTHER INFORMATION: n is deoxyinosine
<220> FEATURE:

<220> FEATURE:
<221> NAME/KEY: misc_feature
<222> LOCATION: (51)..(70)
<223> OTHER INFORMATION: n is deoxyuracil

<400> SEQUENCE: 11
aatcaatctt cattcaaatc atcagacaaa aatcntagag ccntttagnn nanaaaancc    60
aganatagtn atctat    76

<210> SEQ ID NO 12
<211> LENGTH: 76
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (35)..(43)
<223> OTHER INFORMATION: n is deoxyuracil
<220> FEATURE:
<221> NAME/KEY: misc_feature
<222> LOCATION: (49)..(50)
<223> OTHER INFORMATION: n is deoxyinosine
<220> FEATURE:
<221> NAME/KEY: misc_feature
<222> LOCATION: (51)..(70)
<223> OTHER INFORMATION: n is deoxyuracil

<400> SEQUENCE: 12
attattcact tcaaactaat ctacgacaaa aatcntagag ccntttagnn nanaaaancc    60
aganatagtn atctac    76

<210> SEQ ID NO 13
<211> LENGTH: 65
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (30)..(30)
<223> OTHER INFORMATION: n is deoxyinosine

<400> SEQUENCE: 13
tacactttat caaatcttac aatcgggcan ctaaaggaag ctctattaga tacaggagca    60
gataa    65

<210> SEQ ID NO 14
<211> LENGTH: 65
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (30)..(30)
<223> OTHER INFORMATION: n is deoxyinosine

<400> SEQUENCE: 14
ctttatcaat acatactaca atcagggcan ctaaaggaag ctctattaga tacaggagca    60
gatga    65

<210> SEQ ID NO 15
<211> LENGTH: 67
<212> TYPE: DNA
<213> ORGANISM: Artificial
<220> FEATURE:
<223> OTHER INFORMATION: Tag sequence + HIV-1 sequence

```
<220> FEATURE:
<221> NAME/KEY: misc_feature
<222> LOCATION: (28)..(28)
<223> OTHER INFORMATION: n is deoxyinosine

<400> SEQUENCE: 15
caattcaaat cacaataatc aatcgaanat ggaaaccaaa aatgataggg ggaattggag    60
gttttat                                                              67

<210> SEQ ID NO 16
<211> LENGTH: 67
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(28)
<223> OTHER INFORMATION: n is deoxyinosine

<400> SEQUENCE: 16
tcaacaatct tttacaatca aatcgaanat ggaaaccaaa aatgataggg ggaattggag    60
gttttgt                                                              67

<210> SEQ ID NO 17
<211> LENGTH: 77
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (30)..(39)
<223> OTHER INFORMATION: n is deoxyuracil
<220> FEATURE:
<221> NAME/KEY: misc_feature
<222> LOCATION: (57)..(61)
<223> OTHER INFORMATION: n is deoxyinosine

<400> SEQUENCE: 17
taatcttcta tatcaacatc ttacgaaatn tgnggacana aagctatagg tacagtntta    60
ntaggaccta cacctgc                                                   77

<210> SEQ ID NO 18
<211> LENGTH: 77
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (30)..(39)
<223> OTHER INFORMATION: n is deoxyuracil
<220> FEATURE:
<221> NAME/KEY: misc_feature
<222> LOCATION: (57)..(61)
<223> OTHER INFORMATION: n is deoxyinosine

<400> SEQUENCE: 18
aatcctttta cattcattac ttacgaaatn tgnggacana aagctatagg tacagtntta    60
ntaggaccta cacctgt                                                   77

<210> SEQ ID NO 19
<211> LENGTH: 73
<212> TYPE: DNA
<213> ORGANISM: Artificial
<220> FEATURE:
```

<223> OTHER INFORMATION: Tag sequence + HIV-1 sequence
<220> FEATURE:
<221> NAME/KEY: misc_feature
<222> LOCATION: (51)..(51)
<223> OTHER INFORMATION: n is deoxyinosine

<400> SEQUENCE: 19
tacaaatcat caatcacttt aatcgacata aagctatagg tacagtatta ntaggaccta    60
cacctgtcaa cat                                                       73

<210> SEQ ID NO 20
<211> LENGTH: 73
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (51)..(51)
<223> OTHER INFORMATION: n is deoxyinosine

<400> SEQUENCE: 20
tacactttct ttctttcttt ctttgacata aagctatagg tacagtatta ntaggaccta    60
cacctgtcaa ctg                                                       73

<210> SEQ ID NO 21
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (40)..(44)
<223> OTHER INFORMATION: n is deoxyinosine

<400> SEQUENCE: 21
ctactataca tcttactata ctttagctat aggtacagtn ttantaggac ctacacctgt    60
caacataatt ggaagaaa                                                  78

<210> SEQ ID NO 22
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (40)..(44)
<223> OTHER INFORMATION: n is deoxyinosine

<400> SEQUENCE: 22
atacttcatt cattcatcaa ttcaagctat aggtacagtn ttantaggac ctacacctgt    60
caacataatt ggaagaag                                                  78

<210> SEQ ID NO 23
<211> LENGTH: 67
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (41)..(59)
<223> OTHER INFORMATION: n is deoxyuracil

<400> SEQUENCE: 23
ctttaatctc aatcaataca aatcggcctg aaaatccata naatactcca gtatttgcna    60
taaagaa                                                              67

<210> SEQ ID NO 24
<211> LENGTH: 67
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (41)..(59)
<223> OTHER INFORMATION: n is deoxyuracil

<400> SEQUENCE: 24
tacattacca ataatcttca aatcggcctg aaaatccata naatactcca gtatttgcna    60
taaagag                                                              67

<210> SEQ ID NO 25
<211> LENGTH: 69
<212> TYPE: DNA
<213> ORGANISM: Artificial
<220> FEATURE:
<223> OTHER INFORMATION: Tag sequence + HIV-1 sequence

<400> SEQUENCE: 25
atcatacata catacaaatc tacacagtat ttgccataaa gaaaaaagac agtactaaat    60
ggagaaaag                                                            69

<210> SEQ ID NO 26
<211> LENGTH: 69
<212> TYPE: DNA
<213> ORGANISM: Artificial
<220> FEATURE:
<223> OTHER INFORMATION: Tag sequence + HIV-1 sequence

<400> SEQUENCE: 26
caattcattt accaatttac caatcagtat ttgccataaa gaaaaaagac agtactaaat    60
ggagaaaat                                                            69

<210> SEQ ID NO 27
<211> LENGTH: 72
<212> TYPE: DNA
<213> ORGANISM: Artificial
<220> FEATURE:
<223> OTHER INFORMATION: Tag sequence + HIV-1 sequence

<400> SEQUENCE: 27
aatcaatctt cattcaaatc atcaagtatt tgccataaag aaaaaagaca gtactaaatg    60
gagaaaatta ac                                                        72

<210> SEQ ID NO 28
<211> LENGTH: 72
<212> TYPE: DNA
<213> ORGANISM: Artificial
<220> FEATURE:
<223> OTHER INFORMATION: Tag sequence + HIV-1 sequence

<400> SEQUENCE: 28
caataaacta tacttcttca ctaaagtatt tgccataaag aaaaaagaca gtactaaatg    60
gagaaaatta gt                                                        72

<210> SEQ ID NO 29
<211> LENGTH: 57
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (39)..(39)
<223> OTHER INFORMATION: n is deoxyuracil

<400> SEQUENCE: 29
tcaatcaatt acttactcaa atacggaata ccacatccng cagggttaaa aagaaa      57

<210> SEQ ID NO 30
<211> LENGTH: 57
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (39)..(39)
<223> OTHER INFORMATION: n is deoxyuracil

<400> SEQUENCE: 30
aatccttttt actcaattca atcaggaata ccacatccng cagggttaaa aagaac      57

<210> SEQ ID NO 31
<211> LENGTH: 50
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (32)..(32)
<223> OTHER INFORMATION: n is deoxyuracil

<400> SEQUENCE: 31
tcaatcaatt acttactcaa ataccacatc cngcagggtt aaaaagaaa             50

<210> SEQ ID NO 32
<211> LENGTH: 50
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (32)..(32)
<223> OTHER INFORMATION: n is deoxyuracil

<400> SEQUENCE: 32
aatccttttt actcaattca atcacacatc cngcagggtt aaaaagaac             50

<210> SEQ ID NO 33
<211> LENGTH: 65
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (36)..(36)
<223> OTHER INFORMATION: n is deoxyinosine

<400> SEQUENCE: 33
ctacaaacaa acaaacatta tcaagagaca ccaggnatta gatatcagta caatgtgctt      60
ccaat 65

<210> SEQ ID NO 34
<211> LENGTH: 65
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (36)..(36)
<223> OTHER INFORMATION: n is deoxyinosine

<400> SEQUENCE: 34
cttttcaatt acttcaaatc ttcagagaca ccaggnatta gatatcagta caatgtgctt      60
ccaca      65

<210> SEQ ID NO 35
<211> LENGTH: 75
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (64)..(64)
<223> OTHER INFORMATION: n is deoxyuracil

<400> SEQUENCE: 35 ttcactttc aatcaacttt aatcgacaaa aatcttagag cctttagaa aacaaaatcc      60 aganatagtt atcta      75

<210> SEQ ID NO 36
<211> LENGTH: 75
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (64)..(64)
<223> OTHER INFORMATION: n is deoxyuracil

<400> SEQUENCE: 36
tcattcatat acataccaat tcatgacaaa aatcttagag cctttagaa aacaaaatcc      60 aganatagtt atctg      75

<210> SEQ ID NO 37
<211> LENGTH: 71
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (52)..(52)
<223> OTHER INFORMATION: n is deoxyuracil

<400> SEQUENCE: 37
cttttcatct tttcatcttt caatagagcc ttttagaaaa caaatccag anatagttat      60 ctatcaatac a      71

<210> SEQ ID NO 38
<211> LENGTH: 71
<212> TYPE: DNA

<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (52)..(52)
<223> OTHER INFORMATION: n is deoxyuracil

<400> SEQUENCE: 38
ctttctacat tattcacaac attaagagcc ttttagaaaa caaaatccag anatagttat    60
ctatcaatac g    71

<210> SEQ ID NO 39
<211> LENGTH: 80
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (47)..(47)
<223> OTHER INFORMATION: n is deoxyuracil

<400> SEQUENCE: 39
tacatcaaca attcattcaa tacacttttg gaaaacaaaa tccaganata gttatctatc    60
aatacatgga tgatttgtat    80

<210> SEQ ID NO 40
<211> LENGTH: 80
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (47)..(47)
<223> OTHER INFORMATION: n is deoxyuracil

<400> SEQUENCE: 40
ctttcaatta caatactcat tacacttttg gaaaacaaaa tccaganata gttatctatc    60
aatacatgga tgatttgtta    80

<210> SEQ ID NO 41
<211> LENGTH: 72
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (34)..(61)
<223> OTHER INFORMATION: n is deoxyuracil

<400> SEQUENCE: 41
tcaatcatct ttatacttca caataaatcc aganatagtt atctatcaat acatggatga    60
nttgtatgta gc    72

<210> SEQ ID NO 42
<211> LENGTH: 72
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (34)..(61)
<223> OTHER INFORMATION: n is deoxyuracil

<400> SEQUENCE: 42
tcatcaatct ttcaatttac ttacaaatcc aganatagtt atctatcaat acatggatga    60
nttgtatgta gg                                                       72

<210> SEQ ID NO 43
<211> LENGTH: 77
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (65)..(72)
<223> OTHER INFORMATION: n is deoxyinosine

<400> SEQUENCE: 43
tatatacact tctcaataac taaccataga acaaaaatag aggaactgag acaacatctg    60
ttgangtggg gntttac                                                  77

<210> SEQ ID NO 44
<211> LENGTH: 77
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (65)..(72)
<223> OTHER INFORMATION: n is deoxyinosine

<400> SEQUENCE: 44
ctactaattc attaacatta ctaccataga acaaaaatag aggaactgag acaacatctg    60
ttgangtggg gntttta                                                  77

<210> SEQ ID NO 45
<211> LENGTH: 50
<212> TYPE: DNA
<213> ORGANISM: Artificial
<220> FEATURE:
<223> OTHER INFORMATION: Tag sequence + HIV-1 sequence

<400> SEQUENCE: 45
ttcaatcatt caaatctcaa ctttggcatt ccctacaatc cccaaagtaa               50

<210> SEQ ID NO 46
<211> LENGTH: 50
<212> TYPE: DNA
<213> ORGANISM: Artificial
<220> FEATURE:
<223> OTHER INFORMATION: Tag sequence + HIV-1 sequence

<400> SEQUENCE: 46
cttttacaat acttcaatac aatcggcatt ccctacaatc cccaaagtca               50

<210> SEQ ID NO 47
<211> LENGTH: 50
<212> TYPE: DNA
<213> ORGANISM: Artificial
<220> FEATURE:
<223> OTHER INFORMATION: Tag sequence + HIV-1 sequence

<400> SEQUENCE: 47
aatcctttct ttaatctcaa atcaggcatt ccctacaatc cccaaagtcg               50

```
<210> SEQ ID NO 48
<211> LENGTH: 68
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (55)..(55)
<223> OTHER INFORMATION: n is deoxyinosine

<400> SEQUENCE: 48
ctttaatcct ttatcacttt atcaattccc tacaatcccc aaagtcaagg agtantagaa      60
tctatgaa                                                              68

<210> SEQ ID NO 49
<211> LENGTH: 68
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (55)..(55)
<223> OTHER INFORMATION: n is deoxyinosine

<400> SEQUENCE: 49 tcaaatctc aaatactcaa atcaattccc tacaatcccc aaagtcaagg agtantagaa       60
tctatgca                                                              68

<210> SEQ ID NO 50
<211> LENGTH: 51
<212> TYPE: DNA
<213> ORGANISM: Human immunodeficiency virus type 1
<220> FEATURE:
<221> NAME/KEY: misc_feature
<222> LOCATION: (26)..(26)
<223> OTHER INFORMATION: n is deoxyinosine

<400> SEQUENCE: 50
tagtagattt cagagaactt aataanagaa ctcaagactt ctgggaagtt c               51

<210> SEQ ID NO 51
<211> LENGTH: 47
<212> TYPE: DNA
<213> ORGANISM: Human immunodeficiency virus type 1
<220> FEATURE:
<221> NAME/KEY: misc_feature
<222> LOCATION: (38)..(38)
<223> OTHER INFORMATION: n is deoxyinosine

<400> SEQUENCE: 51
tggatgattt gtatgtagga tctgacttag aaataggnca gcataga                   47

<210> SEQ ID NO 52
<211> LENGTH: 62
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is deoxyinosine

<400> SEQUENCE: 52
aggagtagta gaatctatga ataaagaatt aagaaaatt ataggacang taagagatca      60
gg                                                                    62
```

<210> SEQ ID NO 53
<211> LENGTH: 36
<212> TYPE: DNA
<213> ORGANISM: Human immunodeficiency virus type 1
<220> FEATURE:
<221> NAME/KEY: misc_feature
<222> LOCATION: (26)..(34)
<223> OTHER INFORMATION: n is deoxyuracil

<400> SEQUENCE: 53
aattggaaga aatctgttga ctcagnttgg ntgnac                             36

<210> SEQ ID NO 54
<211> LENGTH: 50
<212> TYPE: DNA
<213> ORGANISM: Human immunodeficiency virus type 1
<220> FEATURE:
<221> NAME/KEY: misc_feature
<222> LOCATION: (19)..(19)
<223> OTHER INFORMATION: n is deoxyinosine

<400> SEQUENCE: 54
atctgactta gaaataggnc agcatagaac aaaaatagag gaactgagac               50

<210> SEQ ID NO 55
<211> LENGTH: 62
<212> TYPE: DNA
<213> ORGANISM: Human immunodeficiency virus type 1
<220> FEATURE:
<221> NAME/KEY: misc_feature
<222> LOCATION: (52)..(52)
<223> OTHER INFORMATION: n is deoxyinosine

<400> SEQUENCE: 55
aaaagacagt actaaatgga gaaaattagt agatttcaga gaacttaata anagaactca   60
ag                                                                  62

<210> SEQ ID NO 56
<211> LENGTH: 53
<212> TYPE: DNA
<213> ORGANISM: Human immunodeficiency virus type 1
<220> FEATURE:
<221> NAME/KEY: misc_feature
<222> LOCATION: (22)..(22)
<223> OTHER INFORMATION: n is deoxyinosine

<400> SEQUENCE: 56
agatttcaga gaacttaata anagaactca agacttctgg gaagttcaat tag          53

<210> SEQ ID NO 57
<211> LENGTH: 62
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is deoxyinosine

<400> SEQUENCE: 57
cggagtagta gaatctatga ataaagaatt aagagaaatt ataggacang taagagatca   60
gg                                                                  62

<210> SEQ ID NO 58
<211> LENGTH: 51
<212> TYPE: DNA

```
<213> ORGANISM: Human immunodeficiency virus type 1
<220> FEATURE:
<221> NAME/KEY: misc_feature
<222> LOCATION: (27)..(28)
<223> OTHER INFORMATION: n is deoxyuracil
<220> FEATURE:
<221> NAME/KEY: misc_feature
<222> LOCATION: (29)..(29)
<223> OTHER INFORMATION: n is deoxyinosine
<220> FEATURE:
<221> NAME/KEY: misc_feature
<222> LOCATION: (37)..(37)
<223> OTHER INFORMATION: n is deoxyuracil

<400> SEQUENCE: 58
caaagtaaga cagtatgatc agatacnnnt agaaatntgt ggacataaag c          51

<210> SEQ ID NO 59
<211> LENGTH: 36
<212> TYPE: DNA
<213> ORGANISM: Human immunodeficiency virus type 1
<220> FEATURE:
<221> NAME/KEY: misc_feature
<222> LOCATION: (32)..(32)
<223> OTHER INFORMATION: n is deoxyuracil

<400> SEQUENCE: 59
caacataatt ggaagaaatc tgttgactca gnttgg                           36

<210> SEQ ID NO 60
<211> LENGTH: 36
<212> TYPE: DNA
<213> ORGANISM: Human immunodeficiency virus type 1
<220> FEATURE:
<221> NAME/KEY: misc_feature
<222> LOCATION: (10)..(31)
<223> OTHER INFORMATION: n is deoxyuracil

<400> SEQUENCE: 60
cacaccagan aaaaacatc agaaagaacc nccatt                            36

<210> SEQ ID NO 61
<211> LENGTH: 29
<212> TYPE: DNA
<213> ORGANISM: Human immunodeficiency virus type 1

<400> SEQUENCE: 61
gggatggaaa ggatcaccag caatattcc                                   29

<210> SEQ ID NO 62
<211> LENGTH: 62
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is deoxyinosine

<400> SEQUENCE: 62
tggagtagta gaatctatga ataaagaatt aaagaaaatt ataggacang taagagatca  60
gg                                                                62

<210> SEQ ID NO 63
<211> LENGTH: 62
<212> TYPE: DNA
<213> ORGANISM: Human immunodeficiency virus type 1
<220> FEATURE:
<221> NAME/KEY: misc_feature
```

<222> LOCATION: (28)..(55)
<223> OTHER INFORMATION: n is deoxyinosine

<400> SEQUENCE: 63
taaagaatta agaaaatta taggacangt aagagatcag gctgaacatc ttaanacagc        60
ag                                                                     62

<210> SEQ ID NO 64
<211> LENGTH: 53
<212> TYPE: DNA
<213> ORGANISM: Human immunodeficiency virus type 1
<220> FEATURE:
<221> NAME/KEY: misc_feature
<222> LOCATION: (16)..(16)
<223> OTHER INFORMATION: n is deoxyuracil
<220> FEATURE:
<221> NAME/KEY: misc_feature
<222> LOCATION: (33)..(33)
<223> OTHER INFORMATION: n is deoxyinosine

<400> SEQUENCE: 64
tacagtatta gaaganatga atttgccagg aanatggaaa ccaaaaatga tag              53

<210> SEQ ID NO 65
<211> LENGTH: 36
<212> TYPE: DNA
<213> ORGANISM: Human immunodeficiency virus type 1
<220> FEATURE:
<221> NAME/KEY: misc_feature
<222> LOCATION: (26)..(34)
<223> OTHER INFORMATION: n is deoxyuracil

<400> SEQUENCE: 65
tattggaaga aatctgttga ctcagnttgg ntgnac                                 36

<210> SEQ ID NO 66
<211> LENGTH: 34
<212> TYPE: DNA
<213> ORGANISM: Human immunodeficiency virus type 1
<220> FEATURE:
<221> NAME/KEY: misc_feature
<222> LOCATION: (14)..(19)
<223> OTHER INFORMATION: n is deoxyuracil

<400> SEQUENCE: 66
tctgttgact cagnttggnt gcactttaaa tttt                                   34

<210> SEQ ID NO 67
<211> LENGTH: 44
<212> TYPE: DNA
<213> ORGANISM: Human immunodeficiency virus type 1
<220> FEATURE:
<221> NAME/KEY: misc_feature
<222> LOCATION: (16)..(16)
<223> OTHER INFORMATION: n is deoxyuracil

<400> SEQUENCE: 67
tcaatacatg gatganttgt atgtaggatc tgacttagaa atag                        44

<210> SEQ ID NO 68
<211> LENGTH: 31
<212> TYPE: DNA
<213> ORGANISM: Human immunodeficiency virus type 1

<400> SEQUENCE: 68
aaatcagtaa cagtactgga tgtgggtgat g                                      31

```
<210> SEQ ID NO 69
<211> LENGTH: 49
<212> TYPE: DNA
<213> ORGANISM: Human immunodeficiency virus type 1
<220> FEATURE:
<221> NAME/KEY: misc_feature
<222> LOCATION: (24)..(24)
<223> OTHER INFORMATION: n is deoxyinosine

<400> SEQUENCE: 69
gtaggatctg acttagaaat aggncagcat agaacaaaaa tagaggaac            49

<210> SEQ ID NO 70
<211> LENGTH: 26
<212> TYPE: DNA
<213> ORGANISM: Human immunodeficiency virus type 1
<220> FEATURE:
<221> NAME/KEY: misc_feature
<222> LOCATION: (9)..(15)
<223> OTHER INFORMATION: n is deoxyinosine
<220> FEATURE:
<221> NAME/KEY: misc_feature
<222> LOCATION: (16)..(16)
<223> OTHER INFORMATION: n is deoxyuracil
<220> FEATURE:
<221> NAME/KEY: misc_feature
<222> LOCATION: (18)..(18)
<223> OTHER INFORMATION: n is deoxyinosine

<400> SEQUENCE: 70
aaatcagtna cagtnntnga tgtggg                                    26

<210> SEQ ID NO 71
<211> LENGTH: 26
<212> TYPE: DNA
<213> ORGANISM: Human immunodeficiency virus type 1
<220> FEATURE:
<221> NAME/KEY: misc_feature
<222> LOCATION: (7)..(16)
<223> OTHER INFORMATION: n is deoxyuracil

<400> SEQUENCE: 71
tcaatanatg gatganttgt atgtag                                    26

<210> SEQ ID NO 72
<211> LENGTH: 44
<212> TYPE: DNA
<213> ORGANISM: Human immunodeficiency virus type 1
<220> FEATURE:
<221> NAME/KEY: misc_feature
<222> LOCATION: (6)..(30)
<223> OTHER INFORMATION: n is deoxyuracil

<400> SEQUENCE: 72
caatanatgg atganttgta tgtaggatcn gacttagaga tagg                44

<210> SEQ ID NO 73
<211> LENGTH: 94
<212> TYPE: DNA
<213> ORGANISM: Human immunodeficiency virus type 1

<400> SEQUENCE: 73
ccccaaagtc aaggagtart agaatctatg aataaagaat taagaaaat tataggacar  60 gtaagagatc aggctgaaca tcttaaraca gcag                            94

<210> SEQ ID NO 74
<211> LENGTH: 74
```

```
<212> TYPE: DNA
<213> ORGANISM: Human immunodeficiency virus type 1

<400> SEQUENCE: 74
ggagcagatg atacagtatt agaagamatr rrttttrccag gaaratggaa accaaaaatg    60 ataggggaa ttgg                                                        74

<210> SEQ ID NO 75
<211> LENGTH: 72
<212> TYPE: DNA
<213> ORGANISM: Human immunodeficiency virus type 1

<400> SEQUENCE: 75
ggaggtttta tcaaagtaag acagtatgat cagrtacyyr tagaaatytg yggacayaaa     60
gctataggta ca                                                        72

<210> SEQ ID NO 76
<211> LENGTH: 63
<212> TYPE: DNA
<213> ORGANISM: Human immunodeficiency virus type 1

<400> SEQUENCE: 76
cctacacctg tcaacataat tggaagaaat ctgttgactc agmttggytg yactttaaat     60
ttt                                                                  63

<210> SEQ ID NO 77
<211> LENGTH: 63
<212> TYPE: DNA
<213> ORGANISM: Human immunodeficiency virus type 1

<400> SEQUENCE: 77
gggttaaaaa agaaaaaatc agtaacagta ctggatgtgg gtgatgcata yttytcagtt     60
ccc                                                                  63

<210> SEQ ID NO 78
<211> LENGTH: 56
<212> TYPE: DNA
<213> ORGANISM: Human immunodeficiency virus type 1

<400> SEQUENCE: 78
ggatggaaag gatcaccagc aatattccaa wgtagcatga caaaaatctt agagcc         56

<210> SEQ ID NO 79
<211> LENGTH: 76
<212> TYPE: DNA
<213> ORGANISM: Human immunodeficiency virus type 1

<400> SEQUENCE: 79
gttatctatc aatacatgga tgayttgtat gtaggatctg acttagaaat agrrcagcat     60
agaryaaaaa tagagg                                                    76

<210> SEQ ID NO 80
<211> LENGTH: 61
<212> TYPE: DNA
<213> ORGANISM: Human immunodeficiency virus type 1

<400> SEQUENCE: 80
gtggggrttt accacaccag ayaaaaaaca tcagaaagaa ccyccattyc tttggatggg     60
t                                                                    61
```

<210> SEQ ID NO 81
<211> LENGTH: 82
<212> TYPE: DNA
<213> ORGANISM: Human immunodeficiency virus type 1

<400> SEQUENCE: 81
cyataaagaa aaargacagt actaaatgga gaaaattagt agatttyaga gaacttaata       60
araraactca agacttytgg ga                                                82

<210> SEQ ID NO 82
<211> LENGTH: 71
<212> TYPE: DNA
<213> ORGANISM: Human immunodeficiency virus type 1

<400> SEQUENCE: 82
tggagaaaat tagtagattt yagagaactt aataararaa ctcaagactt ytgggaagtt       60
caattaggaa t                                                            71

<210> SEQ ID NO 83
<211> LENGTH: 82
<212> TYPE: DNA
<213> ORGANISM: Human immunodeficiency virus type 1
<220> FEATURE:
<221> NAME/KEY: misc_feature
<222> LOCATION: (46)..(46)
<223> OTHER INFORMATION: n is a, c, g, t or u

<400> SEQUENCE: 83
ggargttcaa ttaggaatac cacayccwgc aggrttaaaa magaanaaat cagtracagt       60
rytrgatgtg ggsgatgcat at                                                82

<210> SEQ ID NO 84
<211> LENGTH: 81
<212> TYPE: DNA
<213> ORGANISM: Human immunodeficiency virus type 1

<400> SEQUENCE: 84
vhaattaatt gtayaagacc carcaacaat acaagaarar gtatammtat rggaccaggg       60
aragcaktwt wtdcwacars a                                                 81

<210> SEQ ID NO 85
<211> LENGTH: 81
<212> TYPE: DNA
<213> ORGANISM: Human immunodeficiency virus type 1

<400> SEQUENCE: 85
tammtatrgg accagggara gcaktwtwtd cwacarsavr hataatagga ratataagam       60
aagcayattg taaymttart r                                                 81

<210> SEQ ID NO 86
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine -continued

```
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 86
ctttatcaat acatactaca atcagaanga anctgtanna attaattgta caagacccan        60
caacaataca agaaaaaa                                                     78

<210> SEQ ID NO 87
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 87
ctttaatctc aatcaataca aatcgaanga anctgtanna attaattgta caagacccan        60
caacaataca agaaaaag                                                     78

<210> SEQ ID NO 88
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 88 aatccttta cattcattac ttacgaanga anctgtanna attaattgta caagacccan         60
caacaataca agaaaaca                                                     78

<210> SEQ ID NO 89
<211> LENGTH: 78
<212> TYPE: DNA
```

<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 89
tacattacca ataatcttca aatcgaanga anctgtanna attaattgta caagacccan    60
caacaataca agaaaacg                                                 78

<210> SEQ ID NO 90
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 90
caattcaaat cacaataatc aatcgaanga anctgtanna attaattgta caagacccan    60
caacaataca agaaaaga                                                 78

<210> SEQ ID NO 91
<211> LENGTH: 78
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (28)..(32)
<223> OTHER INFORMATION: n is deoxyuracil
<220> FEATURE:
<221> NAME/KEY: misc_feature
<222> LOCATION: (38)..(38)
<223> OTHER INFORMATION: n is deoxyinosine
<220> FEATURE:
<221> NAME/KEY: misc_feature
<222> LOCATION: (39)..(39)
<223> OTHER INFORMATION: n is deoxyuracil
<220> FEATURE:
<221> NAME/KEY: misc_feature
<222> LOCATION: (60)..(60)
<223> OTHER INFORMATION: n is deoxyinosine

<400> SEQUENCE: 91
tacactttat caaatcttac aatcgaanga anctgtanna attaattgta caagacccan    60
caacaataca agaaaagg    78

<210> SEQ ID NO 92
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is a, c, g, t or u
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is a, c, g, t or u

<400> SEQUENCE: 92
caattcattt accaatttac caatacaata caagaaaaag tatanntatn ggaccaggga    60
gagcattttn tncaacagga aa    82

<210> SEQ ID NO 93
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 93
ctttctatct ttctactcaa taatacaata caagaaaaag tatanntatn ggaccaggga    60
gagcattttn tncaacagga ac    82

<210> SEQ ID NO 94
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:

<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 94
tcaacaatct tttacaatca aatcacaata caagaaaaag tatanntatn ggaccaggga      60
gagcattttn tncaacagga ag                                              82

<210> SEQ ID NO 95
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 95
atactaactc aactaacttt aaacacaata caagaaaaag tatanntatn ggaccaggga      60
gagcattttn tncaacagga cc                                              82

<210> SEQ ID NO 96
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 96
aatctcataa tctacataca ctatacaata caagaaaaag tatanntatn ggaccaggga      60
gagcattttu tncaacagga cg                                              82

```
<210> SEQ ID NO 97
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 97
aatcatactc aactaatcat tcaaacaata caagaaaaag tatanntatn ggaccaggga      60
gagcattttn tncaacagga ga                                              82

<210> SEQ ID NO 98
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 98
aatctacact aacaatttca taacacaata caagaaaaag tatanntatn ggaccaggga      60
gagcattttn tncaacagga gc                                              82

<210> SEQ ID NO 99
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
```

```
<221> NAME/KEY: misc_feature
<222> LOCATION: (72)..(72)
<223> OTHER INFORMATION: n is deoxyinosine

<400> SEQUENCE: 99
ctatctttaa actacaaatc taacacaata caagaaaaag tatanntatn ggaccaggga      60
gagcattttn tncaacagga gg                                              82

<210> SEQ ID NO 100
<211> LENGTH: 82
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (45)..(46)
<223> OTHER INFORMATION: n is deoxyuracil
<220> FEATURE:
<221> NAME/KEY: misc_feature
<222> LOCATION: (50)..(50)
<223> OTHER INFORMATION: n is deoxyinosine
<220> FEATURE:
<221> NAME/KEY: misc_feature
<222> LOCATION: (70)..(70)
<223> OTHER INFORMATION: n is deoxyuracil
<220> FEATURE:
<221> NAME/KEY: misc_feature
<222> LOCATION: (72)..(72)
<223> OTHER INFORMATION: n is deoxyinosine

<400> SEQUENCE: 100
tacactttaa acttactaca ctaaacaata caagaaaaag tatanntatn ggaccaggga      60
gagcattttn tncaacagga ca                                              82

<210> SEQ ID NO 101
<211> LENGTH: 66
<212> TYPE: DNA
<213> ORGANISM: Human immunodeficiency virus type 1

<400> SEQUENCE: 101
adtahhtatr ggaccaggga garcatttta tvcaacagga gavataatag gagatataag      60 amaagc                                                                66

<210> SEQ ID NO 102
<211> LENGTH: 66
<212> TYPE: DNA
<213> ORGANISM: Human immunodeficiency virus type 1

<400> SEQUENCE: 102
cdtahhtatr ggaccaggga garcatttta tvcaacagga gavataatag gagatataag      60 amaagc                                                                66

<210> SEQ ID NO 103
<211> LENGTH: 66
<212> TYPE: DNA
<213> ORGANISM: Human immunodeficiency virus type 1

<400> SEQUENCE: 103
gdtahhtatr ggaccaggga garcatttta tvcaacagga gavataatag gagatataag      60 amaagc                                                                66

<210> SEQ ID NO 104
<211> LENGTH: 66
```

<212> TYPE: DNA
<213> ORGANISM: Human immunodeficiency virus type 1

<400> SEQUENCE: 104
tdtahhtatr ggaccaggga garcatttta tvcaacagga gavataatag gagatataag    60 amaagc                                                               66

<210> SEQ ID NO 105
<211> LENGTH: 63
<212> TYPE: DNA
<213> ORGANISM: Human immunodeficiency virus type 1

<400> SEQUENCE: 105
adtahhtatr ggaccaggga garcatttta tacaggagav ataataggag atataagama    60
agc                                                                  63

<210> SEQ ID NO 106
<211> LENGTH: 63
<212> TYPE: DNA
<213> ORGANISM: Human immunodeficiency virus type 1

<400> SEQUENCE: 106
cdtahhtatr ggaccaggga garcatttta tacaggagav ataataggag atataagama    60
agc                                                                  63

<210> SEQ ID NO 107
<211> LENGTH: 63
<212> TYPE: DNA
<213> ORGANISM: Human immunodeficiency virus type 1

<400> SEQUENCE: 107
gdtahhtatr ggaccaggga garcatttta tacaggagav ataataggag atataagama    60
agc                                                                  63

<210> SEQ ID NO 108
<211> LENGTH: 63
<212> TYPE: DNA
<213> ORGANISM: Human immunodeficiency virus type 1

<400> SEQUENCE: 108
tdtahhtatr ggaccaggga garcatttta tacaggagav ataataggag atataagama    60
agc                                                                  63

<210> SEQ ID NO 109
<211> LENGTH: 63
<212> TYPE: DNA
<213> ORGANISM: Human immunodeficiency virus type 1

<400> SEQUENCE: 109
adtahhtatr ggaccaggga garcatttta tvcaacagav ataataggag atataagama    60
agc                                                                  63

<210> SEQ ID NO 110
<211> LENGTH: 63
<212> TYPE: DNA
<213> ORGANISM: Human immunodeficiency virus type 1

<400> SEQUENCE: 110
cdtahhtatr ggaccaggga garcatttta tvcaacagav ataataggag atataagama    60

```
agc                                                              63

<210> SEQ ID NO 111
<211> LENGTH: 63
<212> TYPE: DNA
<213> ORGANISM: Human immunodeficiency virus type 1

<400> SEQUENCE: 111
gdtahhtatr ggaccaggga garcatttta tvcaacagav ataataggag atataagama    60
agc                                                              63

<210> SEQ ID NO 112
<211> LENGTH: 63
<212> TYPE: DNA
<213> ORGANISM: Human immunodeficiency virus type 1

<400> SEQUENCE: 112
tdtahhtatr ggaccaggga garcatttta tvcaacagav ataataggag atataagama    60
agc                                                              63

<210> SEQ ID NO 113
<211> LENGTH: 61
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is a, c, g, t or u

<400> SEQUENCE: 113
arbaatagga ratataagam aagcayattg taaymttart rrarcavant ggratracac    60
t                                                                61

<210> SEQ ID NO 114
<211> LENGTH: 61
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is a, c, g, t or u

<400> SEQUENCE: 114
crbaatagga ratataagam aagcayattg taaymttart rrarcavant ggratracac    60
t                                                                61

<210> SEQ ID NO 115
<211> LENGTH: 61
<212> TYPE: DNA
<213> ORGANISM: Human immunodeficiency virus type 1
<220> FEATURE:
<221> NAME/KEY: misc_feature
<222> LOCATION: (49)..(49)
<223> OTHER INFORMATION: n is a, c, g, t or u

<400> SEQUENCE: 115
grbaatagga ratataagam aagcayattg taaymttart rrarcavant ggratracac    60
t                                                                61

<210> SEQ ID NO 116
<211> LENGTH: 61
<212> TYPE: DNA
<213> ORGANISM: Human immunodeficiency virus type 1
```

```
<220> FEATURE:
<221> NAME/KEY: misc_feature
<222> LOCATION: (49)..(49)
<223> OTHER INFORMATION: n is a, c, g, t or u

<400> SEQUENCE: 116
trbaatagga ratataagam aagcayattg taaymttart rrarcavant ggratracac    60
t                                                                   61

<210> SEQ ID NO 117
<211> LENGTH: 58
<212> TYPE: DNA
<213> ORGANISM: Human immunodeficiency virus type 1
<220> FEATURE:
<221> NAME/KEY: misc_feature
<222> LOCATION: (46)..(46)
<223> OTHER INFORMATION: n is a, c, g, t or u

<400> SEQUENCE: 117
arbaatagga ratataagag cayattgtaa ymttartrra rcavantggr atracact      58

<210> SEQ ID NO 118
<211> LENGTH: 58
<212> TYPE: DNA
<213> ORGANISM: Human immunodeficiency virus type 1
<220> FEATURE:
<221> NAME/KEY: misc_feature
<222> LOCATION: (46)..(46)
<223> OTHER INFORMATION: n is a, c, g, t or u

<400> SEQUENCE: 118
crbaatagga ratataagag cayattgtaa ymttartrra rcavantggr atracact      58

<210> SEQ ID NO 119
<211> LENGTH: 58
<212> TYPE: DNA
<213> ORGANISM: Human immunodeficiency virus type 1
<220> FEATURE:
<221> NAME/KEY: misc_feature
<222> LOCATION: (46)..(46)
<223> OTHER INFORMATION: n is a, c, g, t or u

<400> SEQUENCE: 119
grbaatagga ratataagag cayattgtaa ymttartrra rcavantggr atracact      58

<210> SEQ ID NO 120
<211> LENGTH: 58
<212> TYPE: DNA
<213> ORGANISM: Human immunodeficiency virus type 1
<220> FEATURE:
<221> NAME/KEY: misc_feature
<222> LOCATION: (46)..(46)
<223> OTHER INFORMATION: n is a, c, g, t or u

<400> SEQUENCE: 120
trbaatagga ratataagag cayattgtaa ymttartrra rcavantggr atracact      58

<210> SEQ ID NO 121
<211> LENGTH: 24
<212> TYPE: DNA
<213> ORGANISM: Human immunodeficiency virus type 1

<400> SEQUENCE: 121
taaacaatgg ccattgacag aaga                                           24

<210> SEQ ID NO 122
```

```
<211> LENGTH: 25
<212> TYPE: DNA
<213> ORGANISM: Human immunodeficiency virus type 1

<400> SEQUENCE: 122
tcaaaaattg ggcctgaaaa tccat                                      25

<210> SEQ ID NO 123
<211> LENGTH: 25
<212> TYPE: DNA
<213> ORGANISM: Human immunodeficiency virus type 1

<400> SEQUENCE: 123
gctattaagt cttttgatgg gtcat                                      25

<210> SEQ ID NO 124
<211> LENGTH: 24
<212> TYPE: DNA
<213> ORGANISM: Human immunodeficiency virus type 1

<400> SEQUENCE: 124
taaatttagg agtctttccc cata                                       24

<210> SEQ ID NO 125
<211> LENGTH: 62
<212> TYPE: DNA
<213> ORGANISM: Artificial
<220> FEATURE:
<223> OTHER INFORMATION: Tag sequence + HIV-1 sequence
<220> FEATURE:
<221> NAME/KEY: misc_feature
<222> LOCATION: (36)..(36)
<223> OTHER INFORMATION: n is a, c, g, t or u

<400> SEQUENCE: 125
ttaggaatac cacaccctgc agggttaaaa aagaanaaat cagtgacagt actggatgtg    60
gg                                                                  62

<210> SEQ ID NO 126
<211> LENGTH: 76
<212> TYPE: DNA
<213> ORGANISM: Human immunodeficiency virus type 1

<400> SEQUENCE: 126
gttagagccc tttagaacaa aaaatccaga aatagtcatc trccaatata tggatgactt    60
gtatgtagga tctgac                                                   76

<210> SEQ ID NO 127
<211> LENGTH: 76
<212> TYPE: DNA
<213> ORGANISM: Human immunodeficiency virus type 1

<400> SEQUENCE: 127
gttagagccc tttagaacaa aaaatccaga aatagtcatc trtcaatata tggatgactt    60
gtatgtagga tctgac                                                   76

<210> SEQ ID NO 128
<211> LENGTH: 35
<212> TYPE: DNA
<213> ORGANISM: Human immunodeficiency virus type 1

<400> SEQUENCE: 128
ggacaycaaa tgaaagattg yactgaraga caggc                              35
```

<210> SEQ ID NO 129
<211> LENGTH: 37
<212> TYPE: DNA
<213> ORGANISM: Human immunodeficiency virus type 1

<400> SEQUENCE: 129
cccccctttt cttttaaaat tgtgratgaa tactgcc                              37

<210> SEQ ID NO 130
<211> LENGTH: 40
<212> TYPE: DNA
<213> ORGANISM: Human immunodeficiency virus type 1
<220> FEATURE:
<221> NAME/KEY: misc_feature
<222> LOCATION: (1)..(1)
<223> OTHER INFORMATION: n is a, c, g, t or u

<400> SEQUENCE: 130
natctgctcc tgtatctaat agagcttcct ttagctgccc                           40

<210> SEQ ID NO 131
<211> LENGTH: 45
<212> TYPE: DNA
<213> ORGANISM: Human immunodeficiency virus type 1
<220> FEATURE:
<221> NAME/KEY: misc_feature
<222> LOCATION: (1)..(1)
<223> OTHER INFORMATION: n is a, c, g, t or u

<400> SEQUENCE: 131
nttttctcca tttagtactg tcttttttct ttatggcaaa tactg                     45

<210> SEQ ID NO 132
<211> LENGTH: 54
<212> TYPE: DNA
<213> ORGANISM: Human immunodeficiency virus type 1
<220> FEATURE:
<221> NAME/KEY: misc_feature
<222> LOCATION: (1)..(1)
<223> OTHER INFORMATION: n is a, c, g, t or u

<400> SEQUENCE: 132
ncaaatcatc catgtattga tagataacta tatctggatt ttgttttcta aaag           54

<210> SEQ ID NO 133
<211> LENGTH: 43
<212> TYPE: DNA
<213> ORGANISM: Human immunodeficiency virus type 1
<220> FEATURE:
<221> NAME/KEY: misc_feature
<222> LOCATION: (1)..(1)
<223> OTHER INFORMATION: n is a, c, g, t or u

<400> SEQUENCE: 133
ncatagattc tactactcct tgactttggg gattgtaggg aat                       43

<210> SEQ ID NO 134
<211> LENGTH: 22
<212> TYPE: DNA
<213> ORGANISM: Human immunodeficiency virus type 1

<400> SEQUENCE: 134
gagggcttcc caccccctgc gt                                              22

<210> SEQ ID NO 135

```
<211> LENGTH: 30
<212> TYPE: DNA
<213> ORGANISM: Human immunodeficiency virus type 1

<400> SEQUENCE: 135
tcttgcctgg agctgtttga tgccccagac                                        30

<210> SEQ ID NO 136
<211> LENGTH: 27
<212> TYPE: DNA
<213> ORGANISM: Human immunodeficiency virus type 1

<400> SEQUENCE: 136
agaaagagca gaagacagtg gcaatga                                           27

<210> SEQ ID NO 137
<211> LENGTH: 22
<212> TYPE: DNA
<213> ORGANISM: Human immunodeficiency virus type 1

<400> SEQUENCE: 137
ccaattccca tacattattg tg                                                22

<210> SEQ ID NO 138
<211> LENGTH: 24
<212> TYPE: DNA
<213> ORGANISM: Human immunodeficiency virus type 1

<400> SEQUENCE: 138
caatttctgg gtccctcct gagg                                               24
```